(12) United States Patent
Saeki et al.

(10) Patent No.: US 12,252,700 B2
(45) Date of Patent: Mar. 18, 2025

(54) PARAMYXOVIRUS VECTOR

(71) Applicant: ID Pharma Co., Ltd., Tokyo (JP)

(72) Inventors: Koichi Saeki, Tokyo (JP); Kohji Kusano, Tokyo (JP); Hiroto Hara, Tokyo (JP); Makoto Inoue, Tokyo (JP); Jitsutaro Kawaguchi, Tokyo (JP)

(73) Assignee: ID Pharma Co., Ltd., Tokyo (JP)

( * ) Notice: Subject to any disclaimer, the term of this patent is extended or adjusted under 35 U.S.C. 154(b) by 270 days.

(21) Appl. No.: 15/774,491

(22) PCT Filed: Nov. 4, 2016

(86) PCT No.: PCT/JP2016/082821
§ 371 (c)(1),
(2) Date: Jan. 8, 2019

(87) PCT Pub. No.: WO2017/082174
PCT Pub. Date: May 18, 2017

(65) Prior Publication Data
US 2020/0283797 A1    Sep. 10, 2020

(30) Foreign Application Priority Data
Nov. 13, 2015    (JP) ................................ 2015-223133

(51) Int. Cl.
C12N 15/86       (2006.01)
C12N 7/00        (2006.01)
C12N 15/113      (2010.01)

(52) U.S. Cl.
CPC ............... *C12N 15/86* (2013.01); *C12N 7/00* (2013.01); *C12N 15/1131* (2013.01); *C12N 2760/18043* (2013.01)

(58) Field of Classification Search
CPC ...... C12N 15/86; C12N 7/00; C12N 15/1131; C12N 2760/18043; C12N 2760/18821; C12N 2760/18822; C12N 2760/18843; C12N 2830/00
See application file for complete search history.

(56) References Cited

U.S. PATENT DOCUMENTS

| | | | |
|---|---|---|---|
| 2010/0311171 A1 | 12/2010 | Nakanishi et al. | |
| 2011/0287538 A1 | 11/2011 | Fusaki et al. | |
| 2012/0214240 A1 | 8/2012 | Nakanishi et al. | |
| 2013/0210150 A1 | 8/2013 | Ban et al. | |
| 2016/0215270 A1 | 7/2016 | Ban et al. | |
| 2018/0195085 A1* | 7/2018 | Saeki | C12N 7/04 |

FOREIGN PATENT DOCUMENTS

| | | | |
|---|---|---|---|
| CN | 102159710 A | 8/2011 | |
| EP | 2434012 A1 | 3/2012 | |
| EP | 2639297 A1 | 9/2013 | |
| EP | 2639297 B1 * | 1/2018 | ........... C12N 5/0696 |
| JP | WO2010/134526 A1 | 11/2010 | |
| JP | WO2012/063817 A1 | 5/2012 | |
| WO | WO-2008/007581 A1 | 1/2008 | |
| WO | WO-2008/133206 A1 | 11/2008 | |
| WO | WO-2010/008054 A1 | 1/2010 | |
| WO | WO-2010/134526 A1 | 11/2010 | |
| WO | WO-2012/029770 A1 | 3/2012 | |
| WO | WO-2012/063817 A1 | 5/2012 | |
| WO | WO-2015/046229 A1 | 4/2015 | |

OTHER PUBLICATIONS

Brunel et al. "Sequence of events in measles virus replication: role of phosphoprotein-nucleocapsid interactions." Journal of virology 88.18 (2014): 10851-10863 (Year: 2014).*
Dohmen et al. "Heat-inducible degron: a method for constructing temperature-sensitive mutants." Science 263.5151 (1994): 1273-1276 (Year: 1994).*
Extended European Search Report for European Patent Application No. 16864136.3 dated Mar. 22, 2019 (5 pages).
Nishimura et al., "Development of defective and persistent Sendai virus vector: a unique gene delivery/expression system ideal for cell reprogramming," J Biol Chem. 286(6):4760-71 (2011).
Nishimura et al., "Simple and effective generation of transgene-free induced pluripotent stem cells using an auto-erasable Sendai virus vector responding to microRNA-302," Stem Cell Res. 23:13-19 (2017).
Sano et al., "Novel Strategy to Control Transgene Expression Mediated by a Sendai Virus-Based Vector Using a Nonstructural C Protein and Endogenous MicroRNAs," PLoS One. 11(10):e0164720 (2016) (18 pages).
International Search Report for International Application No. PCT/JP2016/082821, mailed Feb. 7, 2017 (6 pages) (English language translation provided).
Written Opinion of the International Searching Authority for International Application No. PCT/JP2016/082821, mailed Feb. 7, 2017 (15 pages) (English language translation provided).

(Continued)

*Primary Examiner* — Jeremy C Flinders
*Assistant Examiner* — Alexander W Nicol
(74) *Attorney, Agent, or Firm* — Clark & Elbing LLP

(57) ABSTRACT

An objective of the present invention is to provide an improved negative-strand RNA viral vector and a use thereof, the negative-strand RNA viral vector exhibiting transient high expression of genes loaded in the vector and enabling the rapid removal of the vector after said expression. It was discovered that by adding a micro-RNA target sequence to the NP, P, or L gene of a negative-strand RNA viral vector, it is possible to control the expression of the vector depending on the micro-RNA expressed by the introduction cell. In particular, when a micro-RNA target sequence was added to the NP or P gene, the expression of the vector decreased depending on the micro-RNA, and the removal of the vector was promoted, while the effect was reversed when a micro-RNA target sequence was added to the L gene. The vector can be applied in cell therapy and regenerative medicine and can be used as a therapeutic vector that targets cancer.

2 Claims, 25 Drawing Sheets

Specification includes a Sequence Listing.

(56) References Cited

OTHER PUBLICATIONS

International Preliminary Report on Patentability for International Application No. PCT/JP2016/082821, issued May 15, 2018 (17 pages) (English language translation provided).

Abe et al., "Ex vivo expansion of human HSCs with Sendai virus vector expressing HoxB4 assessed by sheep in utero transplantation," Exp Hematol. 39(1):47-54 (2011).

Bitzer et al., "Sendai virus vectors as an emerging negative-strand RNA viral vector system," J Gene Med. 5(7):543-53 (2003).

Brunel et al., "Sequence of events in measles virus replication: role of phosphoprotein-nucleocapsid interactions," J Virol. 88(18):10851-63 (2014).

Griesenbach et al., "Sendai virus for gene therapy and vaccination," Curr Opin Mol Ther. 7(4):346-52 (2005).

* cited by examiner (A)

(B)

(A)

(B)

SEQUENCE LISTING

```
<160> NUMBER OF SEQ ID NOS: 118

<210> SEQ ID NO 1
<211> LENGTH: 10
<212> TYPE: RNA
<213> ORGANISM: Artificial Sequence
<220> FEATURE:
<223> OTHER INFORMATION: Synthetic Construct

<400> SEQUENCE: 1 cwuuvwcccu                                                          10

<210> SEQ ID NO 2
<211> LENGTH: 10
<212> TYPE: RNA
<213> ORGANISM: Artificial Sequence
<220> FEATURE:
<223> OTHER INFORMATION: Synthetic Construct

<400> SEQUENCE: 2
cuuugacccu                                                          10

<210> SEQ ID NO 3
<211> LENGTH: 10
<212> TYPE: RNA
<213> ORGANISM: Artificial Sequence
<220> FEATURE:
<223> OTHER INFORMATION: Synthetic Construct

<400> SEQUENCE: 3
cauucacccu                                                          10

<210> SEQ ID NO 4
<211> LENGTH: 10
<212> TYPE: RNA
<213> ORGANISM: Artificial Sequence
<220> FEATURE:
<223> OTHER INFORMATION: Synthetic Construct

<400> SEQUENCE: 4
cuuucacccu                                                          10

<210> SEQ ID NO 5
<211> LENGTH: 10
<212> TYPE: DNA
<213> ORGANISM: Artificial Sequence
<220> FEATURE:
<223> OTHER INFORMATION: Synthetic Construct
```

```
<400> SEQUENCE: 5
agggtcaaag                                                           10

<210> SEQ ID NO 6
<211> LENGTH: 10
<212> TYPE: DNA
<213> ORGANISM: Artificial Sequence
<220> FEATURE:
<223> OTHER INFORMATION: Synthetic Construct

<400> SEQUENCE: 6
agggtgaatg                                                           10

<210> SEQ ID NO 7
<211> LENGTH: 10
<212> TYPE: DNA
<213> ORGANISM: Artificial Sequence
<220> FEATURE:
<223> OTHER INFORMATION: Synthetic Construct

<400> SEQUENCE: 7
agggtgaaag                                                           10

<210> SEQ ID NO 8
<211> LENGTH: 30
<212> TYPE: DNA
<213> ORGANISM: Artificial Sequence
<220> FEATURE:
<223> OTHER INFORMATION: Synthetic Construct

<400> SEQUENCE: 8
atagcggccg cgacatgact gccctgaccg                                     30

<210> SEQ ID NO 9
<211> LENGTH: 69
<212> TYPE: DNA
<213> ORGANISM: Artificial Sequence
<220> FEATURE:
<223> OTHER INFORMATION: Synthetic Construct

<400> SEQUENCE: 9
tatgcggccg cgatgaactt tcaccctaag tttttcttac tacggttact gataggtatc    60
gagatcgac                                                            69

<210> SEQ ID NO 10
<211> LENGTH: 42
<212> TYPE: DNA
<213> ORGANISM: Artificial Sequence
<220> FEATURE:
<223> OTHER INFORMATION: Synthetic Construct

<400> SEQUENCE: 10
atatgaattc gcggccgctc gccaccatga ctgccctgac cg                       42

<210> SEQ ID NO 11
<211> LENGTH: 28
<212> TYPE: DNA
<213> ORGANISM: Artificial Sequence
<220> FEATURE:
<223> OTHER INFORMATION: Synthetic Construct

<400> SEQUENCE: 11
atataagctt ctattactga taggtatc                                       28
```

```
<210> SEQ ID NO 12
<211> LENGTH: 79
<212> TYPE: DNA
<213> ORGANISM: Artificial Sequence
<220> FEATURE:
<223> OTHER INFORMATION: Synthetic Construct

<400> SEQUENCE: 12
atataagctt ggtaccttat caccaaaaca tggaagcact tacgattcac caaaacatgg      60
aagcacttag agctcatat                                                  79

<210> SEQ ID NO 13
<211> LENGTH: 79
<212> TYPE: DNA
<213> ORGANISM: Artificial Sequence
<220> FEATURE:
<223> OTHER INFORMATION: Synthetic Construct

<400> SEQUENCE: 13
atatgagctc taagtgcttc catgttttgg tgaatcgtaa gtgcttccat gttttggtga      60
taaggtacca agcttatat                                                  79

<210> SEQ ID NO 14
<211> LENGTH: 81
<212> TYPE: DNA
<213> ORGANISM: Artificial Sequence
<220> FEATURE:
<223> OTHER INFORMATION: Synthetic Construct

<400> SEQUENCE: 14
atatgagctc tcaccaaaac atggaagcac ttacgattca ccaaaacatg gaagcactta      60
agtatggtac ctctagaata t                                               81

<210> SEQ ID NO 15
<211> LENGTH: 81
<212> TYPE: DNA
<213> ORGANISM: Artificial Sequence
<220> FEATURE:
<223> OTHER INFORMATION: Synthetic Construct

<400> SEQUENCE: 15
atattctaga ggtaccatac ttaagtgctt ccatgttttg gtgaatcgta agtgcttcca      60
tgttttggtg agagctcata t                                               81

<210> SEQ ID NO 16
<211> LENGTH: 54
<212> TYPE: DNA
<213> ORGANISM: Artificial Sequence
<220> FEATURE:
<223> OTHER INFORMATION: Synthetic Construct

<400> SEQUENCE: 16
atattctaga gtaagaaaaa cttagggtga aagttcgcgg ccgcggatcc atat            54

<210> SEQ ID NO 17
<211> LENGTH: 54
<212> TYPE: DNA
<213> ORGANISM: Artificial Sequence
<220> FEATURE:
<223> OTHER INFORMATION: Synthetic Construct

<400> SEQUENCE: 17
atatggatcc gcggccgcga actttcaccc taagtttttc ttactctaga atat            54
```

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct

<400> SEQUENCE: 18
ctgcaaccca tggagatgaa gg                                        22

<210> SEQ ID NO 19
<211> LENGTH: 29
<212> TYPE: DNA
<213> ORGANISM: Artificial Sequence
<220> FEATURE:
<223> OTHER INFORMATION: Synthetic Construct

<400> SEQUENCE: 19
ccaagcttct attatctagt tggtcagtg                                 29

<210> SEQ ID NO 20
<211> LENGTH: 29
<212> TYPE: DNA
<213> ORGANISM: Artificial Sequence
<220> FEATURE:
<223> OTHER INFORMATION: Synthetic Construct

<400> SEQUENCE: 20
cactgaccaa ctagataata gaagcttgg                                 29

<210> SEQ ID NO 21
<211> LENGTH: 29
<212> TYPE: DNA
<213> ORGANISM: Artificial Sequence
<220> FEATURE:
<223> OTHER INFORMATION: Synthetic Construct

<400> SEQUENCE: 21
tatacctgca ggctctagag gtaccatac                                 29

<210> SEQ ID NO 22
<211> LENGTH: 22
<212> TYPE: DNA
<213> ORGANISM: Artificial Sequence
<220> FEATURE:
<223> OTHER INFORMATION: Synthetic Construct

<400> SEQUENCE: 22
tcgtggaacc tgtgtatggg cc                                        22

<210> SEQ ID NO 23
<211> LENGTH: 30
<212> TYPE: DNA
<213> ORGANISM: Artificial Sequence
<220> FEATURE:
<223> OTHER INFORMATION: Synthetic Construct

<400> SEQUENCE: 23
ggtaccaagc ttctattatt acgagctgtc                                30

<210> SEQ ID NO 24
<211> LENGTH: 30
<212> TYPE: DNA
<213> ORGANISM: Artificial Sequence
<220> FEATURE:
<223> OTHER INFORMATION: Synthetic Construct

```
<400> SEQUENCE: 24
gacagctcgt aataatagaa gcttggtacc                                          30

<210> SEQ ID NO 25
<211> LENGTH: 60
<212> TYPE: DNA
<213> ORGANISM: Artificial Sequence
<220> FEATURE:
<223> OTHER INFORMATION: Synthetic Construct

<400> SEQUENCE: 25
atatccgcgg agcttcgatc gttctgcacg atagggacta attctctaga ggtaccatac         60

<210> SEQ ID NO 26
<211> LENGTH: 22
<212> TYPE: DNA
<213> ORGANISM: Artificial Sequence
<220> FEATURE:
<223> OTHER INFORMATION: Synthetic Construct

<400> SEQUENCE: 26
atctacaaca tagagaaaga cc                                                  22

<210> SEQ ID NO 27
<211> LENGTH: 30
<212> TYPE: DNA
<213> ORGANISM: Artificial Sequence
<220> FEATURE:
<223> OTHER INFORMATION: Synthetic Construct

<400> SEQUENCE: 27
agcttctatt atctagattc ctcctatccc                                          30

<210> SEQ ID NO 28
<211> LENGTH: 30
<212> TYPE: DNA
<213> ORGANISM: Artificial Sequence
<220> FEATURE:
<223> OTHER INFORMATION: Synthetic Construct

<400> SEQUENCE: 28
ggaggaatct agataataga agcttggtac                                          30

<210> SEQ ID NO 29
<211> LENGTH: 36
<212> TYPE: DNA
<213> ORGANISM: Artificial Sequence
<220> FEATURE:
<223> OTHER INFORMATION: Synthetic Construct

<400> SEQUENCE: 29
atatgcgcgc cgtatgatca tatctctaga ggtacc                                   36

<210> SEQ ID NO 30
<211> LENGTH: 30
<212> TYPE: DNA
<213> ORGANISM: Artificial Sequence
<220> FEATURE:
<223> OTHER INFORMATION: Synthetic Construct

<400> SEQUENCE: 30
gcttctatta atgttggtca gtgactctat                                          30

<210> SEQ ID NO 31
```

<211> LENGTH: 30
<212> TYPE: DNA
<213> ORGANISM: Artificial Sequence
<220> FEATURE:
<223> OTHER INFORMATION: Synthetic Construct

<400> SEQUENCE: 31
gaccaacatt aatagaagct tggtacctta    30

<210> SEQ ID NO 32
<211> LENGTH: 37
<212> TYPE: DNA
<213> ORGANISM: Artificial Sequence
<220> FEATURE:
<223> OTHER INFORMATION: Synthetic Construct

<400> SEQUENCE: 32
atatcctgca ggtattacta ctctagaggt accatac    37

<210> SEQ ID NO 33
<211> LENGTH: 71
<212> TYPE: DNA
<213> ORGANISM: Artificial Sequence
<220> FEATURE:
<223> OTHER INFORMATION: Synthetic Construct

<400> SEQUENCE: 33
gtaccatact taagtgcttc catgttttgg tgataaggta ccaagcttct attatctagt    60
tggtcagtga c    71

<210> SEQ ID NO 34
<211> LENGTH: 37
<212> TYPE: DNA
<213> ORGANISM: Artificial Sequence
<220> FEATURE:
<223> OTHER INFORMATION: Synthetic Construct

<400> SEQUENCE: 34
atatcctgca ggtatctcta gaggtaccat acttaag    37

<210> SEQ ID NO 35
<211> LENGTH: 80
<212> TYPE: DNA
<213> ORGANISM: Artificial Sequence
<220> FEATURE:
<223> OTHER INFORMATION: Synthetic Construct

<400> SEQUENCE: 35
catgttttgg tgaatcgtaa gtgcttccat gttttggtga taaggtacca agcttctatt    60
atctagttgg tcagtgactc    80

<210> SEQ ID NO 36
<211> LENGTH: 80
<212> TYPE: DNA
<213> ORGANISM: Artificial Sequence
<220> FEATURE:
<223> OTHER INFORMATION: Synthetic Construct

<400> SEQUENCE: 36
atatcctgca ggatctctag aggtaccata cttaagtgct tccatgtttt ggtgaatcgt    60
aagtgcttcc atgttttggt    80

<210> SEQ ID NO 37
<211> LENGTH: 55

```
<212> TYPE: DNA
<213> ORGANISM: Artificial Sequence
<220> FEATURE:
<223> OTHER INFORMATION: Synthetic Construct

<400> SEQUENCE: 37
ctttagcaat ggtgataatc caccaagctt ctattatcta gttggtcagt gactc      55

<210> SEQ ID NO 38
<211> LENGTH: 79
<212> TYPE: DNA
<213> ORGANISM: Artificial Sequence
<220> FEATURE:
<223> OTHER INFORMATION: Synthetic Construct

<400> SEQUENCE: 38
atatcctgca ggctctcgac tgaattgcac tttagcaatg gtgaatcgaa ttgcacttta    60
gcaatggtga taatccacc                                                79

<210> SEQ ID NO 39
<211> LENGTH: 53
<212> TYPE: DNA
<213> ORGANISM: Artificial Sequence
<220> FEATURE:
<223> OTHER INFORMATION: Synthetic Construct

<400> SEQUENCE: 39
gagtaataat gcgtaatcca ccaagcttct attatctagt tggtcagtga ctc           53

<210> SEQ ID NO 40
<211> LENGTH: 79
<212> TYPE: DNA
<213> ORGANISM: Artificial Sequence
<220> FEATURE:
<223> OTHER INFORMATION: Synthetic Construct

<400> SEQUENCE: 40
atatcctgca ggctctcgac tgtcgtaccg tgagtaataa tgcgatcgtc gtaccgtgag    60
taataatgcg taatccacc                                                79

<210> SEQ ID NO 41
<211> LENGTH: 26
<212> TYPE: DNA
<213> ORGANISM: Artificial Sequence
<220> FEATURE:
<223> OTHER INFORMATION: Synthetic Construct

<400> SEQUENCE: 41
atatggatcc agttcacgcg gccgca                                        26

<210> SEQ ID NO 42
<211> LENGTH: 26
<212> TYPE: DNA
<213> ORGANISM: Artificial Sequence
<220> FEATURE:
<223> OTHER INFORMATION: Synthetic Construct

<400> SEQUENCE: 42
atatctcgag tcggtgcagg ccttta                                        26

<210> SEQ ID NO 43
<211> LENGTH: 27
<212> TYPE: DNA
<213> ORGANISM: Artificial Sequence
<220> FEATURE:
```

<223> OTHER INFORMATION: Synthetic Construct

<400> SEQUENCE: 43
ggatcatacg gcgcgccaag gtacttg                                27

<210> SEQ ID NO 44
<211> LENGTH: 27
<212> TYPE: DNA
<213> ORGANISM: Artificial Sequence
<220> FEATURE:
<223> OTHER INFORMATION: Synthetic Construct

<400> SEQUENCE: 44
caagtacctt ggcgcgccgt atgatcc                                27

<210> SEQ ID NO 45
<211> LENGTH: 28
<212> TYPE: DNA
<213> ORGANISM: Artificial Sequence
<220> FEATURE:
<223> OTHER INFORMATION: Synthetic Construct

<400> SEQUENCE: 45
caactagatc ctgcaggagg catcctac                               28

<210> SEQ ID NO 46
<211> LENGTH: 28
<212> TYPE: DNA
<213> ORGANISM: Artificial Sequence
<220> FEATURE:
<223> OTHER INFORMATION: Synthetic Construct

<400> SEQUENCE: 46
gtaggatgcc tcctgcagga tctagttg                               28

<210> SEQ ID NO 47
<211> LENGTH: 30
<212> TYPE: DNA
<213> ORGANISM: Artificial Sequence
<220> FEATURE:
<223> OTHER INFORMATION: Synthetic Construct

<400> SEQUENCE: 47
atatggatcc gtacgatcgc agtccaccat                             30

<210> SEQ ID NO 48
<211> LENGTH: 26
<212> TYPE: DNA
<213> ORGANISM: Artificial Sequence
<220> FEATURE:
<223> OTHER INFORMATION: Synthetic Construct

<400> SEQUENCE: 48
atatctcgag cagctagctc aactga                                 26

<210> SEQ ID NO 49
<211> LENGTH: 25
<212> TYPE: DNA
<213> ORGANISM: Artificial Sequence
<220> FEATURE:
<223> OTHER INFORMATION: Synthetic Construct

<400> SEQUENCE: 49
gtgaatggga ggccggccat aggtc                                  25

```
<210> SEQ ID NO 50
<211> LENGTH: 25
<212> TYPE: DNA
<213> ORGANISM: Artificial Sequence
<220> FEATURE:
<223> OTHER INFORMATION: Synthetic Construct

<400> SEQUENCE: 50
gacctatggc cggcctccca ttcac                                    25

<210> SEQ ID NO 51
<211> LENGTH: 22
<212> TYPE: DNA
<213> ORGANISM: Artificial Sequence
<220> FEATURE:
<223> OTHER INFORMATION: Synthetic Construct

<400> SEQUENCE: 51
tcaccattgc taaagtgcaa tt                                       22

<210> SEQ ID NO 52
<211> LENGTH: 48
<212> TYPE: DNA
<213> ORGANISM: Artificial Sequence
<220> FEATURE:
<223> OTHER INFORMATION: Synthetic Construct

<400> SEQUENCE: 52
tcaccattgc taaagtgcaa ttcgattcac cattgctaaa gtgcaatt           48

<210> SEQ ID NO 53
<211> LENGTH: 48
<212> TYPE: DNA
<213> ORGANISM: Artificial Sequence
<220> FEATURE:
<223> OTHER INFORMATION: Synthetic Construct

<400> SEQUENCE: 53
tcaccattga taaagtgcaa ttcgattcac cattgataaa gtgcaatt           48

<210> SEQ ID NO 54
<211> LENGTH: 48
<212> TYPE: DNA
<213> ORGANISM: Artificial Sequence
<220> FEATURE:
<223> OTHER INFORMATION: Synthetic Construct

<400> SEQUENCE: 54
tcaccattaa taaagtgcaa ttcgattcac cattaataaa gtgcaatt           48

<210> SEQ ID NO 55
<211> LENGTH: 48
<212> TYPE: DNA
<213> ORGANISM: Artificial Sequence
<220> FEATURE:
<223> OTHER INFORMATION: Synthetic Construct

<400> SEQUENCE: 55
tcaccattaa gaaagtgcaa ttcgattcac cattaagaaa gtgcaatt           48

<210> SEQ ID NO 56
<211> LENGTH: 48
<212> TYPE: DNA
<213> ORGANISM: Artificial Sequence
<220> FEATURE:
<223> OTHER INFORMATION: Synthetic Construct
```

<400> SEQUENCE: 56
tcaccattaa gtaagtgcaa ttcgattcac cattaagtaa gtgcaatt    48

<210> SEQ ID NO 57
<211> LENGTH: 120
<212> TYPE: DNA
<213> ORGANISM: Artificial Sequence
<220> FEATURE:
<223> OTHER INFORMATION: Synthetic Construct

<400> SEQUENCE: 57
agccatggct tcccgccgga ggtggaggag caggatgatg gcacgctgcc catgtcttgt    60
gcccaggaga gcgggatgga ccgtcaccct gcagcctgtg cttctgctag gatcaatgtg    120

<210> SEQ ID NO 58
<211> LENGTH: 40
<212> TYPE: PRT
<213> ORGANISM: Artificial Sequence
<220> FEATURE:
<223> OTHER INFORMATION: Synthetic Construct

<400> SEQUENCE: 58

Ser His Gly Phe Pro Pro Glu Val Glu Glu Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40

<210> SEQ ID NO 59
<211> LENGTH: 40
<212> TYPE: PRT
<213> ORGANISM: Artificial Sequence
<220> FEATURE:
<223> OTHER INFORMATION: Synthetic Construct

<400> SEQUENCE: 59

Ser His Gly Phe Pro Pro Glu Val Glu Glu Gln Asp Asp Gly Ala Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40

<210> SEQ ID NO 60
<211> LENGTH: 40
<212> TYPE: PRT
<213> ORGANISM: Artificial Sequence
<220> FEATURE:
<223> OTHER INFORMATION: Synthetic Construct

<400> SEQUENCE: 60

Ser His Gly Phe Pro Pro Ala Val Ala Ala Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40

<210> SEQ ID NO 61
<211> LENGTH: 321
<212> TYPE: DNA

```
<213> ORGANISM: Artificial Sequence
<220> FEATURE:
<223> OTHER INFORMATION: Synthetic Construct

<400> SEQUENCE: 61
ggagtgcagg tggaaaccat ctccccagga gacgggcgca ccttccccaa gcgcggccag      60
acctgcgtgg tgcactacac cgggatgctt gaagatggaa agaaatttga ttcctcccgg     120
gacagaaaca agcccttaa gtttatgcta ggcaagcagg aggtgatccg aggctgggaa      180
gaaggggttg cccagatgag tgtgggtcag agagccaaac tgactatatc tccagattat    240
gcctatggtg ccactgggca cccaggcatc atcccaccac atgccactct cgtcttcgat    300
gtggagcttc taaaactgga a                                               321

<210> SEQ ID NO 62
<211> LENGTH: 107
<212> TYPE: PRT
<213> ORGANISM: Artificial Sequence
<220> FEATURE:
<223> OTHER INFORMATION: Synthetic Construct

<400> SEQUENCE: 62

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Pro Glu
            100                 105

<210> SEQ ID NO 63
<211> LENGTH: 107
<212> TYPE: PRT
<213> ORGANISM: Artificial Sequence
<220> FEATURE:
<223> OTHER INFORMATION: Synthetic Construct

<400> SEQUENCE: 63

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 64
<211> LENGTH: 497
<212> TYPE: DNA
<213> ORGANISM: Escherichia coli

<400> SEQUENCE: 64

```
gcggccgcgc caccatgatc agtctgattg cggcgttagc ggtagatctc gttatcggca    60
tggaaaacgc catgccgtgg aacctgcctg ccgatctcgc ctggtttaaa cgcaacacct   120
taaataaacc cgtgattatg ggccgccata cctgggaatc aatcggtcgt ccgttgccag   180
gacgcaagaa tattatcctc agcagtcaac gagtacgga cgatcgcgta acgtgggtga   240
agtcggtgga tgaagccatc gcggcgtgtg gtgacgtacc agaaatcatg gtgattggcg   300
gcggtcgcgt tattgaacag ttcttgccaa aagcgcagaa actgtatctg acgcatatcg   360
acgcagaagt ggaaggcgac actcatttcc cggattacga gccggatgac tgggaatcgg   420
tattcagcga gttccacgat gctgatgcgc agaactctca cagctattgc tttgagattc   480
tggagcggcg actcgag                                                 497
```

<210> SEQ ID NO 65
<211> LENGTH: 159
<212> TYPE: PRT
<213> ORGANISM: Escherichia coli

<400> SEQUENCE: 65

Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 66
<211> LENGTH: 159
<212> TYPE: PRT
<213> ORGANISM: Artificial Sequence
<220> FEATURE:
<223> OTHER INFORMATION: Synthetic Construct

<400> SEQUENCE: 66

Met Ile Ser Leu Ile Ala Ala Leu Ala Val Asp Leu Val Ile Gly Met
1               5                   10                  15

Glu Asn Ala Met Pro Trp Asn Leu Pro Ala Asp Leu Ala Trp Phe Lys 20                  25                  30
Arg Asn Thr Leu Asn Lys Pro Val Ile Met Gly Arg His Thr Trp Glu
                35                  40                  45

Ser Ile Gly Arg Pro Leu Pro Gly Arg Lys Asn Ile Ile Leu Ser Ser
     50                  55                  60

Gln Pro Ser Thr Asp Asp Arg Val Thr Trp Val Lys Ser Val Asp Glu
 65                  70                  75                  80

Ala Ile Ala Ala Cys Gly Asp Val Pro Glu Ile Met Val Ile Gly Gly
                 85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
             115                 120                 125

Glu Pro Asp Asp Trp Glu Ser Val Phe Ser Glu Phe Asp Ala Asp
         130                 135                 140

Ala Gln Asn Ser His Ser Tyr Cys Phe Glu Ile Leu Glu Arg Arg
145                 150                 155

<210> SEQ ID NO 67
<211> LENGTH: 621
<212> TYPE: DNA
<213> ORGANISM: Escherichia coli

<400> SEQUENCE: 67
atgtctaggc tggacaagag taaggtgatt aacagcgcac tggagctgct taatgaggtc      60
ggaatcgaag gtttgacaac ccagaaactc gcccagaagc tgggtgtgga gcagcctaca    120
ttgtattggc atgtgaagaa taagcgggct tgctcgacg ccttggccat tgagatgttg     180
gataggcacc atactcactt tgcccttttg aaggggaaa gctggcaaga cttcttgcgc     240
aataacgcta agagttttag atgtgctttg ctgagtcatc gcaatggagc aaaggtgcat    300
tctgacacac ggcctacaga gaagcagtat gaaactctgg agaatcaatt ggccttcttg    360
tgccaacaag gtttctcact ggagaatgca ttgtatgcac tcagcgctgt gggacatttt    420
actttgggtt gcgtgttgga agatcaagag catcaagtcg ctaaagaaga agggaaaca    480 cctactactg atagtatgcc gcccttgttg cggcaagcta tcgaattgtt tgatcaccaa    540
ggtgcagagc cagccttctt gttcggcctt gaattgatca tctgcggatt ggagaaacaa    600
cttaaatgtg aaagtgggtc t                                              621

<210> SEQ ID NO 68
<211> LENGTH: 207
<212> TYPE: PRT
<213> ORGANISM: Escherichia coli

<400> SEQUENCE: 68

Met Ser Arg Leu Asp Lys Ser Lys Val Ile Asn Ser Ala Leu Glu Leu
1               5                  10                  15

Leu Asn Glu Val Gly Ile Glu Gly Leu Thr Thr Arg Lys Leu Ala Gln
             20                  25                  30

Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
     50                  55                  60

Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Asp Gly
            85                  90                  95

Ala Lys Val His Leu Gly Thr Arg Pro Thr Glu Lys Gln Tyr Glu Thr
        100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 69
<211> LENGTH: 207
<212> TYPE: PRT
<213> ORGANISM: Artificial Sequence
<220> FEATURE:
<223> OTHER INFORMATION: Synthetic Construct

<400> SEQUENCE: 69

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Gln Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asn Gly
            85                  90                  95

Ala Lys Val His Ser Asp Thr Arg Pro Thr Glu Lys Gln Tyr Glu Thr
        100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 70
<211> LENGTH: 53
<212> TYPE: DNA
<213> ORGANISM: Artificial Sequence
<220> FEATURE:

<223> OTHER INFORMATION: Synthetic Construct

<400> SEQUENCE: 70
cgacatttga gcgtaatcca ccaagcttct attatctagt tggtcagtga ctc        53

<210> SEQ ID NO 71
<211> LENGTH: 79
<212> TYPE: DNA
<213> ORGANISM: Artificial Sequence
<220> FEATURE:
<223> OTHER INFORMATION: Synthetic Construct

<400> SEQUENCE: 71
atatcctgca ggctctcgac tgaaagtgct gcgacatttg agcgtacgaa agtgctgcga    60
catttgagcg taatccacc                                                 79

<210> SEQ ID NO 72
<211> LENGTH: 53
<212> TYPE: DNA
<213> ORGANISM: Artificial Sequence
<220> FEATURE:
<223> OTHER INFORMATION: Synthetic Construct

<400> SEQUENCE: 72
gcactgtagc tcataatcca ccaagcttct attatctagt tggtcagtga ctc         53

<210> SEQ ID NO 73
<211> LENGTH: 79
<212> TYPE: DNA
<213> ORGANISM: Artificial Sequence
<220> FEATURE:
<223> OTHER INFORMATION: Synthetic Construct

<400> SEQUENCE: 73
atatcctgca ggctctcgac tgtgagatga agcactgtag ctcaatcgtg agatgaagca    60
ctgtagctca taatccacc                                                 79

<210> SEQ ID NO 74
<211> LENGTH: 52
<212> TYPE: DNA
<213> ORGANISM: Artificial Sequence
<220> FEATURE:
<223> OTHER INFORMATION: Synthetic Construct

<400> SEQUENCE: 74
caatggtgtt tgtaatccac caagcttcta ttatctagtt ggtcagtgac tc           52

<210> SEQ ID NO 75
<211> LENGTH: 79
<212> TYPE: DNA
<213> ORGANISM: Artificial Sequence
<220> FEATURE:
<223> OTHER INFORMATION: Synthetic Construct

<400> SEQUENCE: 75
atatcctgca ggctctcgac tgtggagtgt gacaatggtg tttgatcgtg gagtgtgaca    60
atggtgtttg taatccacc                                                 79

<210> SEQ ID NO 76
<211> LENGTH: 54
<212> TYPE: DNA
<213> ORGANISM: Artificial Sequence
<220> FEATURE:
<223> OTHER INFORMATION: Synthetic Construct

<400> SEQUENCE: 76
gatctaacca tgtgtaatcc accaagcttc tattatctag ttggtcagtg actc         54

<210> SEQ ID NO 77
<211> LENGTH: 79
<212> TYPE: DNA
<213> ORGANISM: Artificial Sequence
<220> FEATURE:
<223> OTHER INFORMATION: Synthetic Construct

<400> SEQUENCE: 77
atatcctgca ggctctcgac tgttgtgctt gatctaacca tgtgatcgtt gtgcttgatc    60
taaccatgtg taatccacc                                                 79

<210> SEQ ID NO 78
<211> LENGTH: 53
<212> TYPE: DNA
<213> ORGANISM: Artificial Sequence
<220> FEATURE:
<223> OTHER INFORMATION: Synthetic Construct

<400> SEQUENCE: 78
cggtgaatgc caataatcca ccaagcttct attatctagt tggtcagtga ctc           53

<210> SEQ ID NO 79
<211> LENGTH: 76
<212> TYPE: DNA
<213> ORGANISM: Artificial Sequence
<220> FEATURE:
<223> OTHER INFORMATION: Synthetic Construct

<400> SEQUENCE: 79
atatcctgca ggctctcgac tgtaaggcac gcggtgaatg ccaaatcgta aggcacgcgg    60
tgaatgccaa taatcc                                                    76

<210> SEQ ID NO 80
<211> LENGTH: 53
<212> TYPE: DNA
<213> ORGANISM: Artificial Sequence
<220> FEATURE:
<223> OTHER INFORMATION: Synthetic Construct

<400> SEQUENCE: 80
gtgaatcagg ccgtaatcca ccaagcttct attatctagt tggtcagtga ctc           53

<210> SEQ ID NO 81
<211> LENGTH: 79
<212> TYPE: DNA
<213> ORGANISM: Artificial Sequence
<220> FEATURE:
<223> OTHER INFORMATION: Synthetic Construct

<400> SEQUENCE: 81
atatcctgca ggctctcgac tagctggtgt tgtgaatcag ccgatcagc tggtgttgtg     60 aatcaggccg taatccacc                                                 79

<210> SEQ ID NO 82
<211> LENGTH: 80
<212> TYPE: DNA
<213> ORGANISM: Artificial Sequence
<220> FEATURE:
<223> OTHER INFORMATION: Synthetic Construct

<400> SEQUENCE: 82
atatcctgca ggctatcgaa ttgcacttta gcaatggtga taatccacca agcttctatt    60
atctagttgg tcagtgactc                                                80

<210> SEQ ID NO 83
<211> LENGTH: 32
<212> TYPE: DNA
<213> ORGANISM: Artificial Sequence
<220> FEATURE:
<223> OTHER INFORMATION: Synthetic Construct

<400> SEQUENCE: 83
agagaacaag actaaggcta ccaggtttga cc                                   32

<210> SEQ ID NO 84
<211> LENGTH: 30
<212> TYPE: DNA
<213> ORGANISM: Artificial Sequence
<220> FEATURE:
<223> OTHER INFORMATION: Synthetic Construct

<400> SEQUENCE: 84
aggcgatcgc tctttcaccc taagttttc                                       30

<210> SEQ ID NO 85
<211> LENGTH: 30
<212> TYPE: DNA
<213> ORGANISM: Artificial Sequence
<220> FEATURE:
<223> OTHER INFORMATION: Synthetic Construct

<400> SEQUENCE: 85
gaaagagcga tcgcctaaca cggcgcaatg                                      30

<210> SEQ ID NO 86
<211> LENGTH: 23
<212> TYPE: DNA
<213> ORGANISM: Artificial Sequence
<220> FEATURE:
<223> OTHER INFORMATION: Synthetic Construct

<400> SEQUENCE: 86
tttgggatct tggctatggt gat                                             23

<210> SEQ ID NO 87
<211> LENGTH: 65
<212> TYPE: DNA
<213> ORGANISM: Artificial Sequence
<220> FEATURE:
<223> OTHER INFORMATION: Synthetic Construct

<400> SEQUENCE: 87
atatgcggcc gcatcaccat tgctaaagtg caattcagat cttcacgatg gccgggttgt    60
tgagc                                                                 65

<210> SEQ ID NO 88
<211> LENGTH: 23
<212> TYPE: DNA
<213> ORGANISM: Artificial Sequence
<220> FEATURE:
<223> OTHER INFORMATION: Synthetic Construct

<400> SEQUENCE: 88
cgtcttgtct gaacgcctct aac                                             23

```
<210> SEQ ID NO 89
<211> LENGTH: 30
<212> TYPE: DNA
<213> ORGANISM: Artificial Sequence
<220> FEATURE:
<223> OTHER INFORMATION: Synthetic Construct

<400> SEQUENCE: 89
gccttgcgat cgccgatcgg tggatgaact                              30

<210> SEQ ID NO 90
<211> LENGTH: 30
<212> TYPE: DNA
<213> ORGANISM: Artificial Sequence
<220> FEATURE:
<223> OTHER INFORMATION: Synthetic Construct

<400> SEQUENCE: 90
ccgatcggcg atcgcaaggc cacacccaac                              30

<210> SEQ ID NO 91
<211> LENGTH: 24
<212> TYPE: DNA
<213> ORGANISM: Artificial Sequence
<220> FEATURE:
<223> OTHER INFORMATION: Synthetic Construct

<400> SEQUENCE: 91
cagagtttgt accagttctt cccc                                    24

<210> SEQ ID NO 92
<211> LENGTH: 30
<212> TYPE: DNA
<213> ORGANISM: Artificial Sequence
<220> FEATURE:
<223> OTHER INFORMATION: Synthetic Construct

<400> SEQUENCE: 92
atatggcgcg ccaaggtact tgatccgtag                              30

<210> SEQ ID NO 93
<211> LENGTH: 56
<212> TYPE: DNA
<213> ORGANISM: Artificial Sequence
<220> FEATURE:
<223> OTHER INFORMATION: Synthetic Construct

<400> SEQUENCE: 93
atatgcgatc gcgaattgca ctttagcaat ggtgatcgat cggtggatga actttc  56

<210> SEQ ID NO 94
<211> LENGTH: 61
<212> TYPE: DNA
<213> ORGANISM: Artificial Sequence
<220> FEATURE:
<223> OTHER INFORMATION: Synthetic Construct

<400> SEQUENCE: 94
atatggccgg ccatcaccat tgctaaagtg caattcatag gtcatggatg ggcaggagtc  60
c                                                                 61

<210> SEQ ID NO 95
<211> LENGTH: 28
<212> TYPE: DNA
```

```
<213> ORGANISM: Artificial Sequence
<220> FEATURE:
<223> OTHER INFORMATION: Synthetic Construct

<400> SEQUENCE: 95
gaatatttat cgaaggttca gaggtgtg                                          28

<210> SEQ ID NO 96
<211> LENGTH: 80
<212> TYPE: DNA
<213> ORGANISM: Artificial Sequence
<220> FEATURE:
<223> OTHER INFORMATION: Synthetic Construct

<400> SEQUENCE: 96
atatcctgca ggctctcgac tgaattgcac tttatcaatg gtgaatcgaa ttgcacttta      60
tcaatggtga taatccacca                                                  80

<210> SEQ ID NO 97
<211> LENGTH: 80
<212> TYPE: DNA
<213> ORGANISM: Artificial Sequence
<220> FEATURE:
<223> OTHER INFORMATION: Synthetic Construct

<400> SEQUENCE: 97
atatcctgca ggctctcgac tgaattgcac tttattaatg gtgaatcgaa ttgcacttta      60
ttaatggtga taatccacca                                                  80

<210> SEQ ID NO 98
<211> LENGTH: 80
<212> TYPE: DNA
<213> ORGANISM: Artificial Sequence
<220> FEATURE:
<223> OTHER INFORMATION: Synthetic Construct

<400> SEQUENCE: 98
atatcctgca ggctctcgac tgaattgcac tttcttaatg gtgaatcgaa ttgcactttc      60
ttaatggtga taatccacca                                                  80

<210> SEQ ID NO 99
<211> LENGTH: 80
<212> TYPE: DNA
<213> ORGANISM: Artificial Sequence
<220> FEATURE:
<223> OTHER INFORMATION: Synthetic Construct

<400> SEQUENCE: 99
atatcctgca ggctctcgac tgaattgcac ttacttaatg gtgaatcgaa ttgcacttac      60
ttaatggtga taatccacca                                                  80

<210> SEQ ID NO 100
<211> LENGTH: 40
<212> TYPE: DNA
<213> ORGANISM: Artificial Sequence
<220> FEATURE:
<223> OTHER INFORMATION: Synthetic Construct

<400> SEQUENCE: 100
atatgcggcc gcgacgtcac catggcttct taccctggac                            40

<210> SEQ ID NO 101
<211> LENGTH: 69
```

```
<212> TYPE: DNA
<213> ORGANISM: Artificial Sequence
<220> FEATURE:
<223> OTHER INFORMATION: Synthetic Construct

<400> SEQUENCE: 101
atatgcggcc gcgatgaact ttcaccctaa gttttcttta ctacggttag ttggcctctc     60
ccatctccc                                                             69

<210> SEQ ID NO 102
<211> LENGTH: 43
<212> TYPE: DNA
<213> ORGANISM: Artificial Sequence
<220> FEATURE:
<223> OTHER INFORMATION: Synthetic Construct

<400> SEQUENCE: 102
atatgcgatc gcaaacatga cagcatatat ccagagatca cag                       43

<210> SEQ ID NO 103
<211> LENGTH: 30
<212> TYPE: DNA
<213> ORGANISM: Artificial Sequence
<220> FEATURE:
<223> OTHER INFORMATION: Synthetic Construct

<400> SEQUENCE: 103
caatttaaat tcatcttttc tcagccattg                                      30

<210> SEQ ID NO 104
<211> LENGTH: 30
<212> TYPE: DNA
<213> ORGANISM: Artificial Sequence
<220> FEATURE:
<223> OTHER INFORMATION: Synthetic Construct

<400> SEQUENCE: 104
gaaaagatga atttaaattg tgcacccatc                                      30

<210> SEQ ID NO 105
<211> LENGTH: 29
<212> TYPE: DNA
<213> ORGANISM: Artificial Sequence
<220> FEATURE:
<223> OTHER INFORMATION: Synthetic Construct

<400> SEQUENCE: 105
atatttaatt aaccaagcac tcacaaggg                                       29

<210> SEQ ID NO 106
<211> LENGTH: 30
<212> TYPE: DNA
<213> ORGANISM: Artificial Sequence
<220> FEATURE:
<223> OTHER INFORMATION: Synthetic Construct

<400> SEQUENCE: 106
gtgcacattt aaattcatct tttctcagcc                                      30

<210> SEQ ID NO 107
<211> LENGTH: 30
<212> TYPE: DNA
<213> ORGANISM: Artificial Sequence
<220> FEATURE:
<223> OTHER INFORMATION: Synthetic Construct
```

```
<400> SEQUENCE: 107
atgaatttaa atgtgcaccc atcagagacc                                   30

<210> SEQ ID NO 108
<211> LENGTH: 30
<212> TYPE: DNA
<213> ORGANISM: Artificial Sequence
<220> FEATURE:
<223> OTHER INFORMATION: Synthetic Construct

<400> SEQUENCE: 108
atatgcgatc gccaccatga cagcatatat                                   30

<210> SEQ ID NO 109
<211> LENGTH: 30
<212> TYPE: DNA
<213> ORGANISM: Artificial Sequence
<220> FEATURE:
<223> OTHER INFORMATION: Synthetic Construct

<400> SEQUENCE: 109
atatatttaa attcagcggt catctggatt                                   30

<210> SEQ ID NO 110
<211> LENGTH: 38
<212> TYPE: DNA
<213> ORGANISM: Artificial Sequence
<220> FEATURE:
<223> OTHER INFORMATION: Synthetic Construct

<400> SEQUENCE: 110
atatgcgatc gcgacatgac tgccctgacc gaaggtgc                          38

<210> SEQ ID NO 111
<211> LENGTH: 68
<212> TYPE: DNA
<213> ORGANISM: Artificial Sequence
<220> FEATURE:
<223> OTHER INFORMATION: Synthetic Construct

<400> SEQUENCE: 111
atatgcgatc gcgatgaact ttcaccctaa gttttttctta ctacggttac tgataggtat   60
cgagatcg                                                           68

<210> SEQ ID NO 112
<211> LENGTH: 29
<212> TYPE: DNA
<213> ORGANISM: Artificial Sequence
<220> FEATURE:
<223> OTHER INFORMATION: Synthetic Construct

<400> SEQUENCE: 112
attggcgcgc caaggtactt gatccgtag                                    29

<210> SEQ ID NO 113
<211> LENGTH: 29
<212> TYPE: DNA
<213> ORGANISM: Artificial Sequence
<220> FEATURE:
<223> OTHER INFORMATION: Synthetic Construct

<400> SEQUENCE: 113
aatcctgcag gatctagttg gtcagtgac                                    29
```

<210> SEQ ID NO 114
<211> LENGTH: 1750
<212> TYPE: DNA
<213> ORGANISM: Artificial Sequence
<220> FEATURE:
<223> OTHER INFORMATION: Synthetic Construct

<400> SEQUENCE: 114

```
gcggccgcgc caccatggat caagacgcct tcatcctcaa agaagactcc gaggtggaga      60
gagaggctcc tggcggcaga gagagcctga gcgacgtcat cggcttcctg gacgccgtgc     120
tgtccagcga gcctacagac attggcggcg ataggagctg gctgcacaat accattaaca     180
cccccaggg ccccggatcc gctcacagag ctaagtccga gggcgaggga gaagtgagca     240
caccctccac ccaggacaac aggagcggcg aggaaagcag ggtgtccggc agaacaagca     300
agcctgaggc tgaggcccac gccggcaacc tggataagca gaatatccac agggccttcg     360
gcggcagaac cggcaccaac tccgtgtccc aggatctggg agacgaggc gacagcggaa     420
tcctggagaa ccccctaat gagagaggct accccaggag cggcatcgag gacgagaaca     480
gggagatggc cgcccacccc gacaagagag gcgaggacca ggctgagggc ctgcctgagg     540
aagtcagagg cagcacctcc ctccctgatg aaggcgaggg cggagccagc aataacggca     600
gatccatgga gcctggctcc tcccacagcg ccagagtcac cggagtgctg gtgattccct     660
cccctgagct ggaggaggct gtgctgagga ggaacaaaag aagacccacc aactccggaa     720
gcaagcctct gacccccgct acagtgcctg gcacaaggag ccccccctctg aataggtaca     780
atagcacagg cagccccccc ggaaaacccc ctagcaccca ggacgagcac atcaacagcg     840
gcgacacacc cgctgtgagg gtgaaggaca gaaagccccc cattggcacc aggagcgtga     900
gcgactgtcc tgccaacggc aggcctatcc accctggcct ggagacagac agcaccaaaa     960
agggcatcgg cgagaacacc tcctccatga aggagatggc caccctgctc acaagcctgg    1020
gagtgatcca gagcgcccaa gagttcgaat cctccagaga cgccagctat gtgtttgcta    1080
ggagggccct gaagtccgcc aactacgccg agatgacctt taatgtctgc ggcctcatcc    1140
tgagcgctga gaagagcagc gccaggaaag tggacgagaa caagcagctg ctcaagcaga    1200
ttcaggaaag cgtcgagagc ttcagggaca tctataagag gttcagcgag taccagaaag    1260
agcagaactc cctgctgatg agcaacctca gcaccctgca catcatcacc gacagaggcg    1320
gcaagaccga taacaccgac agcctgacaa gatcccccctc cgtgttcgcc aagtccaagg    1380
agaacaagac caaagccaca aggtttgacc ctagcatgga gaccctggag atatgaagt    1440
acaagcccga cctcatcagg gaggacgagt ttagagacga aatcaggaat cccgtgtacc    1500
aagagaggga taccgagcct agagcctcca cgccagcag actgctgcct tccaaggaga    1560
aacccacaat gcactccctc agactggtga ttgagagctc ccctctgagc agggccgaaa    1620
aggtggccta tgtcaagtcc ctgtccaagt gcaagaccga tcaggaggtg aaggctgtga    1680
tggagctggt ggaggaggac atcgaaagcc tgaccaattg atagggtacc taatgactcg    1740
aggcggccgc                                                          1750
```

<210> SEQ ID NO 115
<211> LENGTH: 30
<212> TYPE: DNA
<213> ORGANISM: Artificial Sequence
<220> FEATURE:
<223> OTHER INFORMATION: Synthetic Construct

<400> SEQUENCE: 115

```
gcgatcgcgc caccatggat caagacgcct                                           30

<210> SEQ ID NO 116
<211> LENGTH: 44
<212> TYPE: DNA
<213> ORGANISM: Artificial Sequence
<220> FEATURE:
<223> OTHER INFORMATION: Synthetic Construct

<400> SEQUENCE: 116
aatggtgata atccaccaag cttctatcta tcaattggtc aggc                           44

<210> SEQ ID NO 117
<211> LENGTH: 70
<212> TYPE: DNA
<213> ORGANISM: Artificial Sequence
<220> FEATURE:
<223> OTHER INFORMATION: Synthetic Construct

<400> SEQUENCE: 117
tcttactcga ctgaattgca ctttagcaat ggtgaatcga attgcacttt agcaatggtg          60
ataatccacc                                                                 70

<210> SEQ ID NO 118
<211> LENGTH: 51
<212> TYPE: DNA
<213> ORGANISM: Artificial Sequence
<220> FEATURE:
<223> OTHER INFORMATION: Synthetic Construct

<400> SEQUENCE: 118
gcgatcgcga actttcaccc taagttttc ttactcgact gaattgcact t                    51
```

PARAMYXOVIRUS VECTOR

SEQUENCE LISTING

The instant application contains a Sequence Listing which has been submitted electronically in ASCII format and is hereby incorporated by reference in its entirety. Said ASCII copy, created May 7, 2020, is named 50026-087001_Sequence_Listing_05.07.20_ST25 and is 37,389 bytes in size.

TECHNICAL FIELD

The present invention relates to an improved minus-strand RNA virus vector. More particularly, the present invention relates to a minus-strand RNA virus vector that has been modified so as to add a microRNA target sequence to the NP gene, P gene, and/or L gene, and utilization of the virus vector.

BACKGROUND ART

Minus-strand RNA virus vectors such as Sendai virus (SeV) are cytoplasm-type RNA virus vectors (vectors for which all the stages of expression are carried out in the cytoplasm), and therefore, even if such a negative-strand RNA virus vector is used in vivo, there is no risk of genes carried by the vector being incorporated into host chromosomes and causing genetic toxicity. Furthermore, negative-strand RNA virus vectors have several excellent performances, such as that high gene transfer efficiency and high gene expression efficiency can be obtained both in vitro and in vivo, and that long-term sustained expression in vitro is enabled. Accordingly, SeV vectors are widely applied and utilized as gene transfer vectors in the production of pluripotent stem cells, gene therapy/gene vaccination, application to antibody production and functional analysis, and the like (Patent Documents 1 and 2 and Non-Patent Documents 1 and 2).

Heretofore, transient expression caused by deficiency in the P protein of a SeV vector (Patent Document 3 and Non-Patent Document 3), non-replicating vectors (Patent Document 4), removal of a SeV vector by insertion of a temperature-sensitive mutation to the P protein or the L protein and temperature shift (Patent Documents 1 and 2), and removal of a SeV vector by addition of a target sequence of miR-302a or addition of siRNA to the 3'-non-coding region of the L gene (Patent Document 5) have been reported. However, P protein-deficient vectors have problems of low-level expression of carried genes and short expression periods (high expression capability of SeV vectors is impaired), and conventional temperature-sensitive mutant vectors have a problem that removal of the vectors takes time (culturing for several days at 39° C.).

In fact, there is an instance in which a microRNA target sequence was added to the 3'-non-coding region of the L gene of a SeV vector (Patent Document 5); however, there is no instance of adding a microRNA target sequence to the NP gene or P gene of a SeV vector.

CITATION LIST

Patent Documents

Patent Document 1: International Publication No. WO 2010/008054

Patent Document 2: International Publication No. WO 2012/029770
Patent Document 3: International Publication No. WO 2008/133206
Patent Document 4: International Publication No. WO 2008/007581
Patent Document 5: International Publication No. WO 2012/063817

Non-Patent Documents

Non-Patent Document 1: Bitzer M, et al., J Gene Med. (2003) 5, 543-553
Non-Patent Document 2: Griesenbach U, et al., Curr Opin Mol Ther. (2005) 7, 346-352
Non-Patent Document 3: Abe T, et al., Exp Hematol. (2011) 39, 47-54

SUMMARY OF THE INVENTION

Problems to be Solved by the Invention

An object of the present invention is to provide a method for controlling the expression of a minus-strand RNA virus vector by adding a microRNA target sequence to the NP gene, P gene, and/or L gene of a minus-strand RNA virus, and to provide the vector and utilization thereof. Specifically, it is an object of the present invention to provide a minus-strand RNA virus vector in which a microRNA target sequence has been added to the NP gene and/or the P gene of the minus-strand RNA virus, a method for producing the vector, and use of the vector. Furthermore, the present invention provides a method for negatively controlling the expression of the vector by adding a microRNA target sequence to the NP gene and/or the P gene of a minus-strand RNA virus. The present invention also relates to a method for promoting removal of a vector, the method including using a minus-strand RNA virus vector in which a microRNA target sequence has been added to the NP gene and/or the P gene of a minus-strand RNA virus.

Furthermore, another object of the present invention is to provide a minus-strand RNA virus vector in which a microRNA target sequence has been added to the L gene, a method for producing the vector, and use of the vector. Furthermore, the present invention provides a method for positively controlling the expression of the vector by adding a microRNA target sequence to the L gene of a minus-strand RNA virus.

Means for Solving the Problems

The inventors of the present invention searched for a method of improving the speed of removal of a minus-strand RNA virus vector while maintaining the gene expression capability of the vector.

In order to achieve transient expression using a minus-strand RNA virus vector, the inventors of the present invention initially attempted to use P gene-deficient vectors. However, when vectors thus produced were introduced into cells and expression of reporter proteins was investigated, expression of reporter proteins could not be confirmed in HeLa cells, which do not express P protein. In Non-Patent Document 3, it has been also reported that the level of expression of carried genes from a P gene-deficient vector is ⅒ or less compared to vectors in which the P gene is not deleted. Furthermore, the non-replicating SeV vector of Patent Document 4 requires a high titer or the presence of a helper vector in order to obtain a sufficient amount of gene expression, and the vector also exhibits low production efficiency. Meanwhile, in regard to the vectors (TS12 skeleton and TS15 skeleton) described in Patent Document 2, removal of the SeV vectors is carried out by culturing infected cells under the culturing conditions at 39° C. for 7 days; however, the removal needs a longer time at 37° C. For example, in the induction of iPS cells, it took 28 days to obtain alkaline phosphatase-positive colonies from SeV vector infection. Furthermore, from the observation that the vectors are not quickly removed despite the assumption that iPS cells show fast cell proliferation and the vectors are easily removable, it is suggested that common cell strains such as HeLa cells require a longer time for the removal of the vectors.

The present inventors also attempted removal of SeV vectors by addition of degron to the P protein (International Publication No. WO 2016/125364). In a vector in which degron had been added to temperature-sensitive P protein, more rapid removal of the vector was realized compared to the vectors described in Patent Document 2; however, there was a problem that infection needed to be achieved at a temperature lower than the temperature at which vector removal was performed (in the case of the skeleton that is removable at 37° C., infection at 32° C. to 35° C.).

In regard to such problems, the present inventors speculated that the removal of a vector would possibly be promoted by adding a microRNA target sequence to the viral gene of a minus-strand RNA virus vector. Thus, the present inventors first attempted removal of a vector by adding a microRRNA target sequence to the L gene, which was considered to be most suitable for promoting the removal of a vector by a microRNA target sequence among the viral proteins of minus-strand RNA virus vectors. However, when a microRNA target sequence was added to the L gene, the level of expression of the vector in cells that express the microRNA rather increased, and thus, it was difficult to effectively control the expression of an introduced gene or the removal of a vector by adding a microRNA target sequence to the L gene.

Thus, the present inventors carried out an experiment of adding a microRNA target sequence to the P gene of a minus-strand RNA virus. As a result, the inventors found that when a microRNA target sequence was added to the coding region, or the 5'- or 3'-non-coding region of the P gene, highly excellent characteristics were exhibited that the expression of the introduced gene immediately after introduction into a vector in non-microRNA-expressing cells can be achieved at very high level, while the vector is rapidly removed in microRNA-expressing cells. Furthermore, in the case of the L gene, an effect of lowering the level of expression of an introduced gene could not be obtained even when a four-fold repeat microRNA target sequence was added; whereas in the case of the P gene, the same effect was exhibited with a single microRNA target sequence. Moreover, even as compared with a vector in which a microRNA target sequence had been added to the NP gene, the effect of lowering the level of expression of the introduced gene was significant in the case of adding a microRNA target sequence to the P gene. When a comparison was made between the 5'-non-coding region and the 3'-non-coding region of the P gene, the effect of lowering the level of expression of the introduced gene was greater on the 3'-side.

In regard to a vector carrying two P genes, it was successful in lowering the level of expression of one of the P proteins in a cell-specific manner by means of a microRNA target sequence, while lowering the level of expression of the other one of the P proteins by means of temperature sensitivity or a degron. By carrying two P genes having different characteristics of expression control, a vector which can be infected at 37° C. and whose expression is controlled by a plurality of systems of a microRNA target sequence and temperature sensitivity or a degron could be obtained.

Promotion of the removal of vectors in iPS cells was confirmed by a plurality of microRNAs. Furthermore, it was found that not only in iPS cells but also in vascular endothelial cells as a model of the mesoderm, liver cells as a model of the endoderm, nerve cells as a model of the ectoderm, and BJ cells used as a model of normal cells, vectors carrying microRNA target sequences that are expressed specifically in the respective cells are removed. Furthermore, it was found that when a microRNA target sequence which is expressed in normal cells and is expressed to a reduced extent in cancer cells is loaded into an oncolytic virus, the oncolytic virus proliferates in a cancer cell-selective manner. That is, the following can be achieved: causing a transcription factor or the like that is carried on a vector to be transiently expressed at high level in cells that constitute a material for iPS cells, and removing the vector by means of a microRNA that is expressed after reprogramming; causing a transcription factor to be transiently expressed at high level in stem cells, and removing the vector by means of a microRNA that is expressed after induction of differentiation; and increasing the selectivity to cancer cells while suppressing the influence on normal cells with regard to an oncolytic virus. Therefore, the vector of the present invention can be expected to serve as a gene expression vector useful for the modification of the phenotype of cells in regenerative medicine, cell therapy, and the like, or for cancer therapy and the like.

The present invention also provides a modified paramyxovirus vector that has been modified so as to carry a plurality of P genes. According to the present invention, it has been made clear that control of the expression of the P gene is very useful for the control of the expression of a vector or the control of elimination of a vector. When a plurality of P genes is loaded into a vector and the expression of the respective P genes is controlled, the regulation of vector expression or the control of vector elimination can be carried out in a more complicated and richly flexible manner. Particularly, a paramyxovirus vector modified so as to carry a plurality of P genes, in which a microRNA control sequence has been added to at least one P gene, exhibits superior characteristics as a vector for iPS cell production.

That is, the present invention relates to a minus-strand RNA virus vector modified so as to add a microRNA target sequence to the NP gene, P gene, and/or L gene, and utilization thereof, and more specifically, the present invention provides the following inventions.

[1] A modified paramyxovirus vector, comprising the NP gene, P gene, or L gene of the virus that has been modified so as to have a target sequence of a microRNA added to the gene, in which in a cell expressing the microRNA, expression of the vector in which the target sequence of the microRNA is added to the NP gene or P gene is negatively controlled, and expression of the vector in which the target sequence of the microRNA is added to the L gene is positively controlled.

[2] The vector described in [1], wherein the vector is deficient in at least one envelope protein gene.

[3] The vector described in [2], wherein the vector is deficient in at least the F gene or the M gene.

[4] The vector described in any one of [1] to [3], wherein the microRNA target sequence is added to the coding region or the 5'- or 3'-non-coding region of the NP gene, P gene, or L gene.

[5] The vector described in any one of [1] to [4], wherein the paramyxovirus is Sendai virus.

[6] The vector described in any one of [1] to [5], wherein the vector includes a temperature-sensitive mutation.

[7] The vector described in [6], wherein the temperature-sensitive mutation includes the L511F mutation of the P protein.

[8] The vector described in [6] or [7], wherein the temperature-sensitive mutation includes D433A, R434A, and K437A of the P protein.

[9] The vector described in any one of [1] to [8], wherein the microRNA target sequence is selected from the group consisting of various target sequences of miR-122, miR-124, miR-126, miR-138, miR-143, miR-218, miR-302 cluster, miR-367, and miR-372.

[10] The vector described in any one of [1] to [9], wherein the vector carries a transcription factor gene or a suicide gene.

[11] A method for promoting the removal of a paramyxovirus vector, the method including using the vector described in any one of [1] to [10], in which a microRNA target sequence has been added to the NP gene or the P gene.

[12] A method for producing the vector described in any one of [1] to [10], the method including a step of causing a nucleic acid encoding genomic RNA of the vector or a complementary strand thereof together with the NP gene, P gene, and L gene, to none of which a microRNA target sequence is added.

[13] A method for controlling the expression amount of a carried gene, the method including using the vector described in any one of [1] to [10].

[14] The method described in [13], wherein the carried gene encodes a transcription factor.

[15] The method described in [14], wherein the carried gene encodes a reprogramming factor that induces a pluripotent stem cell.

[16] The method described in [13], wherein the carried gene is a suicide gene.

[17] The method described in [13] or [16], wherein the vector is used for the lysis of a tumor cell.

[18] A method for promoting the removal of a paramyxovirus or a paramyxovirus vector, the method including a step of co-infecting the virus or virus vector with the vector described in any one of [1] to [10], in which a microRNA target sequence has been added to the NP gene or P gene.

[19] An agent for promoting the removal of a paramyxovirus or a paramyxovirus vector, the agent including the vector described in any one of [1] to [10].

[20] A modified paramyxovirus vector, carrying two or more P genes.

[21] The vector described in [20], wherein a P protein encoded by at least one Pg gene is temperature-sensitive, and/or a degron has been added.

[22] The vector described in [20] or [21], wherein a microRNA target sequence has been added to the coding region or the 5'- or 3'-non-coding region of the NP gene, P gene, or L gene.

[23] The vector described in [22], wherein the vector is the vector described in any one of [1] to [10].

[24] A method for controlling the amount of expression and/or removal of a vector, the method including using the vector described in any one of [20] to [23] carrying at least one P gene encoding the P protein, which is temperature-sensitive, and/or to which a degron has been added, and at least one P gene to which a microRNA target sequence has been added.

The present invention also relates to the following inventions.

[25] The vector described in any one of [1] to [10], wherein the vector carries a gene encoding a transcription factor.

[26] The vector described in any one of [1] to [10], wherein the vector carries a gene encoding a reprogramming factor.

[27] The vector described in [26], wherein the reprogramming factor is KLF4.

[28] The vector described in any one of [1] to [10], wherein the vector is deficient in the M gene.

[29] The vector described in [28], wherein the cleavage site of the F protein has been modified.

[30] The vector described in [29], wherein the F protein is cleaved by a cancer-specific protease.

[31] The vector described in any one of [28] to [30], carrying a suicide gene.

[32] The vector described in any one of [1] to [10], carrying two or more P genes.

[33] The vector described in [32], wherein a P protein encoded by at least one P gene is temperature-sensitive, and/or a degron has been added.

[34] The vector described in [32] or [33], wherein a microRNA target sequence has been added to the coding region or the 5'- or 3'-non-coding region of the NP gene, P gene, or L gene.

[35] The vector described in any one of [32] to [34], wherein a degron and/or a microRNA target sequence has been added to all of the P genes.

[36] A method for controlling the amount of expression and/or removal of a vector, the method including using the vector described in any one of [32] to [35] carrying at least one P gene encoding a P protein, which is temperature-sensitive, and/or to which a degron has been added, and at least one P gene to which a microRNA target sequence has been added.

[37] Use of a vector for the introduction of a reprogramming factor gene in the reprogramming of cells, the vector being the vector described in any one of [32] to [35] carrying at least one P gene encoding a P protein, which is temperature-sensitive, and/or to which a degron has been added, and at least one P gene to which a microRNA target sequence has been added.

[38] Use of the vector described in [26] or [27] in the reprogramming of cells.

[39] Use of the vector described in any one of [28] to [31] in cancer therapy.

Effects of the Invention

According to the present invention, the removal of a vector can be significantly promoted by adding a microRNA target sequence to the NP gene or P gene. Both a high amount of gene expression and rapid removal of a vector are achieved, and thus, promotion of vector removal in the regulation of expression of a transcription factor, production of iPS cells, and cell differentiation can be achieved without performing culture at high temperature, while enhancement in tumor cell-specific infection can be achieved at the time of oncolytic vector infection. Furthermore, by adding a microRNA target sequence to the L gene, expression of a vector can be increased. For example, when a microRNA target sequence is added to the L gene in an M gene-deficient type oncolytic vector, an increase in the proliferation of the vector can be obtained at the time of oncolytic vector infection.

BRIEF DESCRIPTION OF THE DRAWINGS

FIG. 18(A) shows the appearance of colonies on Day 21 in an assay using Matrigel. In the case of using a vector carrying miR367T2, there were many large ASP-positive colonies. FIG. 18(B) shows the appearance of ALP-positive colonies in a case in which a microRNA target sequence was not added to a KLF4 expression vector (KLF4) and in a case in which miR302T2 or miR367T2 was added (KLF4/miR302T2 and KLF4/miR367T2, respectively).

MODE(S) FOR CARRYING OUT THE INVENTION

Figure 1:
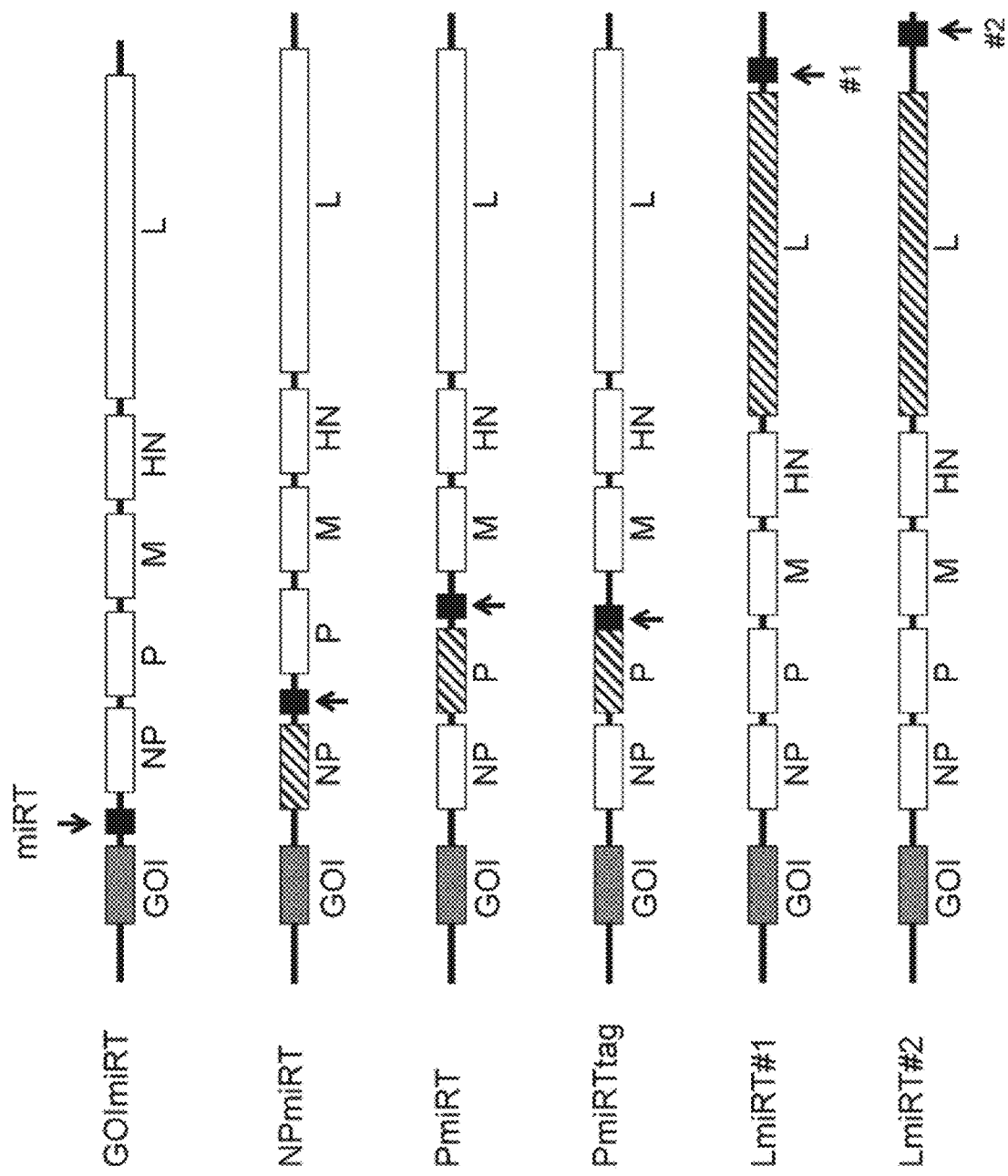
FIG. 1 is a diagram illustrating the loading positions of microRNA target sequences.

Hereinafter, embodiments of the present invention will be described in detail.

The present invention provides a minus-strand RNA virus vector in which a microRNA target sequence has been added to the NP gene, P gene, or L gene of a minus-strand RNA virus, a method for producing a vector, use of a vector, and a method for promoting the removal of a vector. Particularly, the present invention provides a minus-strand RNA virus vector that is deficient in the F gene or M gene of the virus, in which a microRNA target sequence has been added to the NP gene, P gene, or L gene, a method for producing a vector, use of a vector, and a method for promoting the removal of a vector. Here, the term "or" includes embodiments of "and". That is, when it is said that a microRNA target sequence has been added to the NP gene, P gene, or L gene, it is implied that at least a microRNA target sequence has been added to any of the NP gene, P gene, and L gene, and this is not to exclude an embodiment in which a microRNA target sequence has been added to the other genes. For example, microRNA target sequences may be added to two or more of the NP gene, P gene, and L gene, or to all of the genes, and it is also acceptable that a microRNA target sequence is further added to a gene other than those.

A minus-strand RNA virus vector is a virus vector derived from a virus containing a minus-strand (strand encoding a viral protein in antisense) RNA as the genome. A minus-strand RNA is also referred to as negative-strand RNA. According to the present invention, a single-stranded minus-strand RNA virus (non-segmented minus-strand RNA virus) in particular may be mentioned as an example. A single-stranded negative-strand RNA virus refers to a virus having a single-stranded negative-strand (that is, minus-strand) RNA in the genome. Examples of such a virus include viruses belonging to families such as Paramyxoviridae (including the genera *Paramyxovirus, Morbillivirus, Rubulavirus*, and *Pneumovirus*), Rhabdoviridae (including the genera *Vesiculovirus, Lyssavirus*, and *Ephemerovirus*), and Filoviridae, and these viruses taxonomically belong to the order Mononegavirales (Virus, Vol. 57(1), pp. 29-36, 2007; Annu. Rev. Genet. 32, 123-162, 1998; Fields Virology, Fourth Edition, Philadelphia Lippincott-Raven, 1305-1340, 2001; Microbiol. Immunol. 43, 613-624, 1999; and Field Virology, Third Edition, pp. 1205-1241, 1996).

Preferred examples of the minus-strand RNA virus vector according to the present invention include paramyxovirus vectors and rhabdovirus vectors. The paramyxovirus in the present invention refers to a virus belonging to the family Paramyxoviridae or a derivative thereof. The family Paramyxoviridae is one of viral groups having non-segmented negative-strand RNA in the genome, and the family includes the family Paramyxovirinae (including the genera *Respirovirus* (also referred to as the genus *Paramyxovirus*), *Rubulavirus*, and *Morbillivirus*) and the family Pneumovirinae (including the genera *Pneumovirus* and *Metapneumovirus*). Specific examples of the virus included in the viruses of the family Paramyxoviridae include Sendai virus, Newcastle disease virus, Mumps virus, Measles virus, Respiratory syncytial virus, rinderpest virus, distemper virus, simian parainfluenza virus (SV5), and human parainfluenza viruses I, II, and III. More specific examples include Sendai virus (SeV), human parainfluenza virus-1 (HPIV-1), human parainfluenza virus-3 (HPIV-3), phocine distemper virus (PDV), canine distemper virus (CDV), dolphin morbillivirus (DMV), peste-des-petits-ruminants virus (PDPR), measles virus (MeV), rinderpest virus (RPV), Hendra virus (Hendra), Nipah virus (Nipah), human parainfluenza virus-2 (HPIV-2), simian parainfluenza virus 5 (SV5), human parainfluenza virus-4a (HPIV-4a), human parainfluenza virus-4b (HPIV-4b), mumps virus (Mumps), and Newcastle disease virus (NDV). Examples of rhabdovirus include Vesicular stomatitis virus and Rabies virus of the family Rhabdoviridae.

The virus of the present invention is preferably a virus belonging to the family Paramyxovirinae (including the genera *Respirovirus, Rubulavirus*, and *Morbillivirus*) or a derivative thereof, and is more preferably a virus belonging to the genus *Respirovirus* (also referred to the genus *Paramyxovirus*) or a derivative thereof. Examples of the derivative include viruses in which viral genes have been modified so as not to impair the gene transfer ability of the virus, and chemically modified viruses. Examples of the viruses of the genus *Respirovirus*, to which the present invention can be applied, include human parainfluenza virus type 1 (HPIV-1), human parainfluenza virus type 3 (HPIV-3), bovine parainfluenza virus type 3 (BPIV-3), Sendai virus (also called mouse parainfluenza virus type 1), measles virus, simian parainfluenza virus (SV5), and simian parainfluenza virus type 10 (SPIV-10). The paramyxovirus according to the present invention is preferably Sendai virus.

The minus-strand RNA virus generally contains a complex comprising RNA and proteins in the interior of an envelope (ribonucleoprotein; RNP). The RNA included in RNP is (−)-strand (negative-strand) single-stranded RNA that is a genome of a minus-strand RNA virus, and this single-stranded RNA is bound to the NP protein, P protein, and L protein to form RNP. The RNA included in this RNP serves as a template for the transcription and replication of the viral genome (Lamb, R. A., and D. Kolakofsky, 1996, Paramyxoviridae: The viruses and their replication, pp. 1177-1204, In Fields Virology, 3rd ed. Fields, B. N., D. M. Knipe and P. M. Howley, et al., (ed.), Raven Press, New York, N.Y.).

The "NP, P, M, F, HN, and L genes" of a minus-strand RNA virus refer to the genes encoding nucleocapsid, phosphor, matrix, fusion, hemagglutinin-neuraminidase, and large proteins, respectively. The nucleocapsid (NP) protein is bound to the genomic RNA and is an essential protein in order for the genomic RNA to have template activity. Generally, the NP gene may also be described as "N gene". The phosphor (P) protein is a phosphorylated protein that is a small subunit of RNA polymerase. The matrix (M) protein accomplishes a function of maintaining the virus particle structure from the interior. The fusion (F) protein is a membrane fusion protein involved in the penetration into a host cell, and the hemagglutinin-neuraminidase (HN) protein is a protein involved in the binding with a host cell. The large (L) protein is a large subunit of RNA polymerase. Each of the above-described genes has a transcription control unit, and single mRNA is transcribed from each of the genes, from which a protein is transcribed. From the P gene, non-structural protein (C) that is translated by utilizing a different ORF, and protein (V) formed by RNA editing during the reading of P protein mRNA are translated in addition to the P protein. For example, various genes in the various viruses belonging to the family Paramyxovirinae are generally described as follows in the order from the 3'-terminus.

Genus *Respirovirus* N P/C/V M F HN-L
  Genus *Rubulavirus* N P/V M F HN (SH) L
Genus *Morbillivirus* N P/C/V M F H-L For example, regarding the accession numbers in the database of the base sequences of various genes of Sendai virus, see M29343, M30202, M30203, M30204, M51331, M55565, M69046, and X17218 for the N gene; M30202, M30203, M30204, M55565, M69046, X00583, X17007, and X17008 for the P gene; D11446, K02742, M30202, M30203, M30204, M69046, U31956, X00584, and X53056 for the M gene; D00152, D11446, D17334, D17335, M30202, M30203, M30204, M69046, X00152, and X02131 for the F gene; D26475, M12397, M30202, M30203, M30204, M69046, X00586, X02808, and X56131 for the HN gene; and D00053, M30202, M30203, M30204, M69040, X00587, and X58886 for the L gene. Furthermore, examples of viral genes encoded by other viruses may include CDV, AF014953; DMV, X75961; HPIV-1, D01070; HPIV-2, M55320; HPIV-3, D10025; Mapuera, X85128; Mumps, D86172; MeV, K01711; NDV, AF064091; PDPR, X74443; PDV, X75717; RPV, X68311; SeV, X00087; SV5, M81442; and Tupaia, AF079780 for the N gene; CDV, X51869; DMV, Z47758; HPIV-1, M74081; HPIV-3, X04721; HPIV-4a, M55975; HPIV-4b, M55976; Mumps, D86173; MeV, M89920; NDV, M20302; PDV, X75960; RPV, X68311; SeV, M30202; SV5, AF052755; and Tupaia, AF079780 for the P gene; CDV, AF014953; DMV, Z47758; HPIV-1, M74081; HPIV-3, D00047; MeV, ABO16162; RPV, X68311; SeV, AB005796; and Tupaia, AF079780 for the C gene; CDV, M12669; DMV Z30087; HPIV-1, S38067; HPIV-2, M62734; HPIV-3, D00130; HPIV-4a, D10241; HPIV-4b, D10242; Mumps, D86171; MeV, AB012948; NDV, AF089819; PDPR, Z47977; PDV, X75717; RPV, M34018; SeV, U31956; and SV5, M32248 for the M gene; CDV, M21849; DMV, AJ224704; HPN-1, M22347; HPIV-2, M60182; HPIV-3, X05303, HPIV-4a, D49821; HPIV-4b, D49822; Mumps, D86169; MeV, AB003178; NDV, AF048763; PDPR, Z37017; PDV, AJ224706; RPV, M21514; SeV, D17334; and SV5, AB021962 for the F gene; CDV, AF112189; DMV, AJ224705; HPIV-1, U709498; HPIV-2. D000865; HPIV-3, AB012132; HPIV-4A, M34033; HPIV-4B, AB006954; Mumps, X99040; MeV, K01711; NDV, AF204872; PDPR, X74443; PDV, Z36979; RPV, AF132934; SeV, U06433; and SV-5, S76876 for the HN (H or G) gene; and CDV, AF014953; DMV, AJ608288; HPIV-1, AF117818; HPIV-2, X57559; HPIV-3, AB012132; Mumps, AB040874; MeV, K01711; NDV, AY049766; PDPR, AJ849636; PDV, Y09630; RPV, Z30698; and SV-5, D13868 for the L gene. However, a plurality of strains is known for each of the viruses, and genes comprising sequences other than those exemplified above also exist due to the differences in strains. Sendai virus vectors having viral genes derived from any of these genes are useful as vectors of the present invention. Furthermore, in regard to the P protein, the functional site of the protein is a region including the N-binding site, the L-binding site, and the oligomer-forming site on the C-terminal side (in the case of SeV, 320-568 on the C-terminal side of the P protein) (Blanchard L. et al., Virology, (2004) 319, 201-211). It is preferable that the P protein of the present invention includes at least this region. For example, the vector of the present invention includes a base sequence having at least 90%, preferably at least 95', at least 96%, at least 97%, at least 98%, or at least 99% identity with the coding sequence of any one of the above-mentioned viral genes (regarding the P gene of SeV, for example, the coding sequence may be a sequence on the C-terminal side, and for example, may be the amino acid sequence from the 479$^{th}$ to 568$^{th}$ amino acids or the amino acid sequence from the 320$^{th}$ to 568$^{th}$ amino acids). Furthermore, the vector of the present invention includes, for example, a base sequence encoding an amino acid sequence having at least 90%, preferably at least 95%, at least 96%, at least 97%, at least 98%, or at least 99% identity with the amino acid sequence encoded by the coding sequence of any one of the above-mentioned viral genes (regarding the P protein of SEV, for example, the amino acid sequence may be a sequence on the C-terminal side, and for example, may be the amino acid sequence from the 479$^{th}$ to 568$^{r}$ amino acids or the amino acid sequence from the 320$^{th}$ to 568$^{th}$ amino acids). Furthermore, the vector of the present invention includes, for example, a base sequence encoding a polypeptide including an amino acid sequence that has substitutions, insertions, deletions, and/or additions of ten or fewer, preferably nine or fewer, eight or fewer, seven or fewer, six or fewer, five or fewer, four or fewer, three or fewer, two or fewer, or one amino acid with respect to the amino acid sequence encoded by the coding sequence of any one of the above-mentioned viral genes (regarding the P gene of SEV, for example, the amino acid sequence may be a sequence on the C-terminal side, and for example, may be the amino acid sequence from the 479$^{th}$ to 568$^{th}$ amino acids or the amino acid sequence from the 320$^{th}$ to 568$^{th}$ amino acids). Vectors modified so as to add microRNA target sequences to the NP gene, P gene, and/or L gene encoded by such vectors, are very suitable as the vector of the present invention.

The sequences for which the database accession numbers have been referred to, such as base sequences and amino acid sequences described in the present specification, refer to the sequences on, for example, the filing date and priority date of this application and can be identified as sequences at the time of either the filing date or the priority date of the present application. Preferably, the sequences are identified as sequences on the filing date of the present specification. The sequences at the respective time points can be identified by referring to the revision history of the database.

Furthermore, the minus-strand RNA virus of the present invention may be derived from a natural strain, a wild-type strain, a mutant strain, a laboratory-subcultured strain, an artificially established strain, or the like. An example thereof is Sendai virus Z strain (Medical Journal of Osaka University, Vol. 6, No. 1, March 1955, p. 1-15). That is, this virus may be a virus vector having a structure similar to that of a virus isolated from nature, or may be a virus artificially modified by genetic recombination. For example, the virus may have mutations or deletions in any of the genes of a wild-type virus. For example, a virus having a mutation or deletion in at least one gene encoding an envelope virus or a coat protein can be suitably used. Such a virus vector is a virus vector that can, for example, replicate the genome in infected cells but cannot form infective virus particles. Since there is no risk that such a transmission-defective virus vector may spread infection to the surroundings, the virus vector is highly safe. For example, a minus-strand RNA virus that does not contain at least one gene encoding an envelope protein such as the F protein and/or HN protein or a spine protein, or a combination thereof can be used (WO 0070055 and WO 00/70070; Li, H.-O. et al., J. Virol. 74(14) 6564-6569 (2000)). In a case in which proteins necessary for genome replication (for example, the N protein, P protein, and L protein) are encoded in the genomic RNA, the genome can be amplified in infected cells. In order to produce a defective type virus, for example, the deleted gene product or a protein that can complement the gene product is exogenously supplied to the virus-producing cell (WO 00/07755 and WO 00/70070; LI, H.-O. et al., J. Virol. 74(14) 6564-6569 (2000)). Furthermore, a method of collecting a virus vector as non-infective virus-like particles (VLP) without completely complementing the deleted virus protein is also known (WO 00/70070). Furthermore, in the case of collecting a virus vector as RNP (for example, RNP comprising the N, L, and P proteins and genomic RNA), the vector can be produced without complementing the envelope proteins.

The virus of the present invention is not limited to a naturally-occurring virus, and for example, artificially produced viruses are also included in the virus. For example, the virus of the present invention also includes a virus in which mutations have been introduced into the nucleic acid sequence in order to optimize codons, chimeric viruses (including, for example, a chimera between homogenous viruses, and a chimeric virus between heterogeneous viruses (for example, a chimera between PIV and SeV)), and the like (J. Virol. 1995, 849-855).

According to the present invention, the viral proteins such as the N, L, and P proteins may not be wild-type proteins as long as they maintain the function of expressing genes in transduced cells. For example, a modified protein in which a peptide such as a tag has been appropriately added, a protein having modified codons, and a protein in which a portion of the amino acid sequence of the wild type protein has been deleted so as not to lose the function can be used as appropriate. According to the present invention, the N, L, and P proteins also include such modified proteins and deletion type protein. For example, as long as the P protein has a portion of the C-terminus, other regions are not essential for the expression of a virus vector.

The minus-strand RNA virus vector according to the present invention is a vector that has a genomic nucleic acid derived from the virus and is capable of expressing a transgene by incorporating the transgene into the nucleic acid. The minus-strand RNA virus vector according to the present invention includes infective virus particles, as well as a complex of a viral core, a viral genome and viral proteins, or a complex comprising non-infective virus particles or the like, the complex having an ability to express carried genes when introduced into cells.

The vector of the present invention is a vector having the NP gene, P gene, or L gene modified so as to have a microRNA target sequence added thereto, in which in the case of a vector having a microRNA target sequence added to the NP gene and/or P gene as a result of the modification, when the vector is introduced into a cell expressing the microRNA, the expression of the microRNA is negatively controlled compared to the case in which the microRNA target sequence has not been added; and in the case of a vector having a microRNA target sequence added to the L gene, when the vector is introduced into a cell expressing the microRNA, the expression of the microRNA Is positively controlled compared to the case in which the microRNA target sequence has not been added. Here, in regard to the expression of a vector, any one of the level of expression of a gene from the vector (level of expression of mRNA and/or a protein), the number of copies of the vector genome in transduced cells, and the expression period for a transgene, or any arbitrary combination thereof, and preferably at least the level of expression of a gene from the vector, is controlled as described above. For a vector in which a microRNA target sequence has been added to the NP gene and/or P gene, preferably the time taken for the vector to be removed from cells is also shortened.

The virus vector according to the present invention is a vector expressing carried genes when introduced into cells, the virus vector being a complex of, for example, RNA derived from the (−)-strand single-stranded RNA genome of the relevant virus, and proteins derived from the viral proteins binding to a (−)-strand single-stranded RNA of the virus, the proteins being bound to the RNA. The protein that binds to (−)-strand single-stranded RNA according to the present invention refers to a protein that is bound directly and/or indirectly to the (−)-strand single-stranded RNA and forms a complex with the (−)-strand single-stranded RNA. In the complex of the present invention, a complex comprising (−)-strand single-stranded RNA derived from a minus-strand RNA virus, and proteins derived from a minus-strand RNA virus and binding to that RNA (for example, NP, P, and L proteins) is included. According to the present invention, the phrase "derived from a minus-strand RNA virus" means that the constituents (including proteins and RNAs) of a minus-strand RNA virus are in an intact state, or in a state of being partially modified. For example, a protein or RNA produced by modifying a protein or RNA of a minus-strand RNA virus is a protein or RNA "derived from a minus-strand RNA virus" Regarding the vector of the present invention, the type of the vector is not limited as long as the vector has the above-described features. For example, the vector of the present invention may be a virus vector having envelope proteins (F, HN, and M proteins) and having a structure of a virus particle. Furthermore, the vector may also be a RNP vector, which is RNP itself and does not have a viral envelope.

In regard to the minus-strand RNA virus, the NP, P, and L proteins are bound to (−)-strand single-stranded RNA and accomplish the functions indispensable for genomic RNA replication and protein expression (in the following description, in some cases, the NP, P, and L proteins are referred to as "genomic RNA-binding proteins"). The NP protein is a protein that binds very strongly to genomic RNA and imparts template activity to the genomic RNA. The genomic RNA has template activity for RNA synthesis only in a state of being bound to the NP protein and does not have template activity at all in a state of being unbound to the NP protein. The P protein is bound to the genomic RNA as a small subunit of RNA polymerase, and the L protein is bound to the genomic RNA as a large subunit of RNA polymerase. Therefore, in a minus-strand RNA virus, if even any one of the NP, P, and L proteins is missing, genomic RNA replication does not occur.

Such an embodiment of the vector of the present invention is characterized by containing a complex comprising: (a) (−)-strand single-stranded RNA derived from a minus-strand RNA virus, the RNA having the NP gene, P gene, or L gene modified so as to have a microRNA target sequence added thereto; and (b) the NP protein, P protein, and L protein. The vector of the present invention may be a virus particle containing a complex (RNP) comprising a modified (−)-strand single-stranded RNA (genomic RNA) and the NP, P, and L proteins. When a host is infected with the vector of the present invention, proteins are expressed from the genes encoded in the genomic RNA as a result of the functions of the NP, P, and L proteins contained in the vector of the present invention. A vector in which a microRNA target sequence has been added to the NP gene and/or P gene is such that when the vector is introduced into cells expressing the microRNA, expression of the vector is negatively controlled, amplification of the vector genome in the cells is suppressed, and the vector is easily eliminated from the cells. When such a vector is appropriately used in combination of a temperature-sensitive mutation, more effective control of vector expression and more effective control of vector removal can be achieved.

The genes encoded in the genomic RNA of the vector of the present invention may have the intact virus-derived gene sequence; however, it is also acceptable that any mutation is introduced into the genes. For example, a person having ordinary skill in the art can introduce a minor mutation that would not impair the functions of various proteins, into various genes on the genomic RNA according to a known method. For example, mutations can be incorporated site-specifically by a PCR method, a cassette mutagenesis method, or the like, or random mutations can be introduced by means of chemical reagents, random nucleotides, or the like.

For example, in connection with the envelope proteins or spike proteins, many mutations including attenuation mutations and temperature-sensitive mutations are known. Viruses having these mutated protein genes can be suitably used in the present invention. According to the present invention, a vector having attenuated cytotoxicity can be desirably used. Cytotoxicity of a vector can be measured by, for example, quantitatively determining the release of lactic acid dehydrogenase (LDH) from vector-infected cells. As the amount of released LDH is smaller, the cytotoxicity is lower. For example, a vector having significantly attenuated cytotoxicity compared to the wild type can be used. Regarding the degree of attenuation of cytotoxicity, a vector with which the amount of released LDH in a culture fluid obtained by infecting human-derived HeLa cells (ATCC CCL-2) or simian-derived CV-1 cells (ATCC CCL 70) with MOI (multiplicity of infection) of 3, and culturing the cells for three days at 35° C. to 37° C. (for example, 37° C.), is significantly decreased compared to the wild type, for example, the amount of released LDH is decreased by 20% or more, 25% or more, 30% or more, 35% or more, 40% or more, or 50% or more, can be used. Furthermore, mutations lowering cytotoxicity also include temperature-sensitive mutations.

Furthermore, temperature-sensitivity can be determined by measuring the rate of proliferation of virus or the expression level of a carried gene at a temperature normal to the virus host (for example, from 37° C. to 38° C.). It is considered that as the proliferation rate of virus and/or the expression level of a carried gene is decreased, higher temperature sensitivity is obtained, compared to a vector that does not have mutations.

The virus vector used for the present invention has deletions or mutations in preferably at least one, and more preferably at least two, three, four, five, or more viral genes. Deletions and mutations may be introduced in any arbitrary combination into the respective genes. Here, a mutation may be a function-impairing type mutation or a temperature-sensitive mutation, and is a mutation that decreases, at least at 37° C., the virus proliferation rate or the expression level of any of the carried genes to a level of preferably ½ or less, more preferably ⅓ or less, more preferably ⅕ or less, more preferably ¹⁄₁₀ or less, and more preferably ¹⁄₂₀ or less, compared to the wild type. The use of such a modified virus vector can be useful particularly from the viewpoint that cytotoxicity in the host cells can be reduced or the removal of the vector can be promoted. For example, a virus vector that is suitably used in the present invention has at least two viral genes deleted or mutated. Such a virus includes a virus having at least two viral genes deleted, at least two viral genes mutated, and at least one viral gene mutated as well as at least one viral gene deleted. The at least two mutated or deleted viral genes are preferably genes encoding envelope-constituting proteins. For example, it is preferable that the minus-strand RNA virus vector of the present invention is deficient in at least the F gene or M gene. For example, a vector having deletion of the F gene, further deletion of the M and/or HN gene, and further mutation (for example, temperature-sensitive mutation) of the M and/or HN gene, is suitably used in the present invention. Furthermore, the vector used in the present invention more preferably has at least three viral genes (preferably at least three genes encoding envelope-constituting proteins; F, HN, and M) deleted or mutated. Such a virus vector includes a vector having at least three genes deleted, a vector having at least three genes mutated, at least one gene mutated as well as at least two genes deleted, and a vector having at least two genes mutated as well as at least one gene deleted. According to a more preferred embodiment, for example, a vector further having deletion of the F gene, further deletion of the M and HN genes, and further mutation of the M and HN gene (for example, temperature-sensitive mutation), is suitably used in the present invention. Furthermore, for example, a vector further having deletion of the F gene, further deletion of the M or HN gene, and further mutation of the remaining M or HN gene (for example, temperature-sensitive mutation) is suitably used in the present invention. Such a mutated type virus can be produced according to known methods.

Examples of the temperature-sensitive mutation of the M gene include amino acid substitution at a site arbitrarily selected from the group consisting of position 69 (G69), position 116 (T116), and position 183 (A183) of the M protein of Sendai virus; and amino acid substitution at equivalent sites of the M protein of a minus-strand RNA virus (Inoue, M. et al., J. Virol. 2003, 77:3238-3246). A virus having a genome encoding a mutant M protein in which an amino acid at any one of the above-mentioned three sites, preferably amino acids at a combination of any arbitrary two sites, and more preferably amino acids at all of the three sites in the M protein have been substituted by other amino acids, is suitably used in the present invention.

The amino acid mutation is preferably substitution by another amino acid with a side chain having different chemical properties, and for example, substitution by an amino acid having a BLOSUM62 matrix (Henikoff, S. and Henikoff, J. G. (1992) Proc. Natl. Acad. Sci. USA 89:10915-10919) score of 3 or less, preferably 2 or less, more preferably 1 or less, and even more preferably zero, is achieved. Specifically, in the case of Sendai virus M protein, G69, T116, and A183 can be substituted by Glu (E), Ala (A), and Ser (S), respectively. Also for the M protein of another minus-strand RNA virus, the amino acids at the corresponding sites can be substituted by Glu (E), Ala (A), and Ser (S), respectively. Furthermore, mutations homologous to the mutations in the M protein of measles virus temperature-sensitive strain P253-505 (Morikawa Y. et al., Kitasato Arch. Exp. Med. 1991; 64; 15-30) can also be utilized. Introduction of mutations may be carried out according to a known mutagenesis method by using, for example, oligonucleotides.

Furthermore, examples of the temperature-sensitive mutation of the HN gene include amino acid substitution at a site arbitrarily selected from the group consisting of position 262 (A262), position 264 (G264), and position 461 (K461) of the HN protein of Sendai virus; and amino acid substitution at the corresponding sites of the HN protein of a minus-strand RNA virus (Inoue, M. et al., J. Virol. 2003, 77:3238-3246). A virus having a genome encoding a mutant HN protein in which an amino acid at any one of the above-mentioned three sites, preferably amino acids at a combination of any arbitrary two sites, and more preferably amino acids at all of the three sites in the M protein have been substituted by other amino acids, is suitably used in the present invention. As described above, the substitution of an amino acid is preferably substitution by another amino acid with a side chain having different chemical properties. According to a preferred example, A262, G264, and K461 of the Sendai virus HN protein are substituted by Thr (T), Arg (R), and Gly (G), respectively. Also for the M protein of another minus-strand RNA virus, the amino acids at the corresponding sites can be substituted by Thr (T), Arg (R), and Gly (G), respectively. Furthermore, for example, while referring to temperature-sensitive vaccine strain Urabe AM9 of Mumps virus, mutations can be introduced into the amino acids at positions 464 and 468 of the HN protein (Wright, K. E. et al., Virus Res. 2000: 67; 49-57).

Furthermore, the vector of the present invention may also have mutations in the P gene and/or L gene. Specific examples of such mutations include mutation of Glu at position 86 (E86) of the SeV P protein, and substitution of amino acids other than Leu at position 511 (L511) of the SeV P protein. Also for the P protein of another minus-strand RNA virus, substitution at the corresponding sites may be mentioned. As described above, the substitution of an amino acid is preferably substitution by another amino acid with a side chain having different chemical properties. Specific examples include substitution of the amino acid at position 86 by Lys and substitution of the amino acid at position 511 by Phe. In regard to the L protein, substitution by an amino acid other than Asn at position 1197 (N1197) and/or Lys at position 1795 (K1795) of the SeV L protein, and substitution at the corresponding sites of the L protein of another minus-strand RNA virus may be mentioned. As described above, the substitution of an amino acid is preferably substitution by another amino acid with a side chain having different chemical properties. Specific examples include substitution of the amino acid at position 1197 by Ser, and substitution of the amino acid at position 1795 by Glu. Mutation of the P gene and the L gene can markedly increase an effect of sustained infectiveness, suppression of release of secondary particles, or suppression of cytotoxicity. Furthermore, these effects can be dramatically increased by combining mutations and/or deficiency of the envelope protein genes. Furthermore, regarding the L gene, examples include substitution with amino acids other than Tyr at position 1214 (Y1214) and/or Met at position 1602 (M1602) of the SeV L protein, and substitution at the corresponding sites of the L protein of another minus-strand RNA virus. As described above, the substitution of an amino acid is preferably substitution by another amino acid with a side chain having different chemical properties. Specific examples include substitution of the amino acid at position 1214 by Phe, and substitution of the amino acid at position 1602 by Leu. The mutations mentioned above as examples can be used in any arbitrary combinations.

For example, Sendai virus vectors in which at least G at position 69, T at position 116, A at position 183 of the SeV M protein; at least A at position 262, G at position 264, and K at position 461 of the SeV HN protein; at least L at position 511 of the SeV P protein; and at least N at position 1197 and K at position 1795 of the SeV L protein have been respectively substituted by other amino acids, and in which the F gene is deficient or has been deleted; and an F gene-deficient or F gene-deleted Sendai virus vector having cytotoxicity at a level equal to or lower than the above-mentioned vectors and/or temperature sensitivity at a level equal to or higher than the above-mentioned vectors, are particularly suitable. Also for other minus-strand RNA viruses, vectors in which corresponding sites have been similarly substituted and the F gene is deficient or has been deleted; and F gene-deficient or F gene-deleted vectors having cytotoxicity at a level similar to or lower than the above-mentioned vectors and/or temperature sensitivity at a level equal to or higher than the above-mentioned vectors, are preferred. Specific examples of substitution include substitutions of G69E, T116A, and A183S for the M protein; substitutions of A262T, G264R, and K461G for the HN protein; substitution of L511F for the P protein; and substitutions of N1197S and K1795E for the L protein.

Amino acid mutation may be substitution by other desired amino acids; however, the mutation is preferably substitution by other amino acids with a side having different chemical properties, as described above. For example, the amino acids can be classified into groups such as basic amino acids (for example, lysine, arginine, and histidine), acidic amino acids (for example, aspartic acid and glutamic acid), non-charged polar amino acids (for example, glycine, asparagine, glutamine, serine, threonine, tyrosine, and cysteine), non-polar amino acids (for example, alanine, valine, leucine, isoleucine, proline, phenylalanine, methionine, and tryptophan), n-branched amino acids (for example, threonine, valine, and isoleucine), and aromatic amino acids (for example, tyrosine, phenylalanine, tryptophan, and histidine). However, the amino acid mutation may also be such that for a certain amino acid, substitution by amino acids other than the amino acids of the group to which the foregoing amino acid belongs. Specific examples include, in the case of a basic amino acid, substitution by an acidic or neutral amino acid; in the case of a polar amino acid, substitution by a non-polar amino acid; in the case of an amino acid having a molecular weight larger than the average molecular weight of the twenty naturally occurring amino acids, substitution by an amino acid having a molecular weight smaller than the average molecular weight; and in contrast, in the case of an amino acid having a molecular weight smaller than the average molecular weight, substitution by an amino acid having a molecular weight larger than the average molecular weight. However, the examples are not limited to those.

Furthermore, examples of the mutation of the L protein include substitutions of amino acids at sites arbitrarily selected from position 942 (Y942), position 1361 (L1361), and position 1558 (L1558) of the SeV L protein, or substitutions of amino acids at the corresponding sites of the L protein of other minus-strand RNA viruses. As described above, the substitution of an amino acid is preferably substitution by another amino acid with a side chain having different chemical properties. Specific examples may include substitution of the amino acid at position 1558 (substitution) by His, substitution of the amino acid at position 1361 by Cys, and substitution of the amino acid at position 1558 by Ile. Particularly, an L protein in which at least position 942 or position 1558 has been substituted can be suitably used. For example, a mutant L protein in which the amino acids at position 1558 as well as position 1361 have been substituted by other amino acids is also suitable. Furthermore, a mutant L protein in which the amino acids at position 942 as well as position 1558 and/or position 1361 have been substituted by other amino acids is also suitable. As a result of these mutations, the temperature sensitivity of the L protein can be enhanced.

Examples of the mutation of the P protein include substitutions of amino acids at sites arbitrarily selected from position 433 (D433), position 434 (R434), and position 437 (K437) of the SeV P protein; and substitutions of amino acids at the corresponding sites of the P protein of other minus-strand RNA viruses by other amino acids. As described above, the substitution of an amino acid is preferably substitution by another amino acid with a side chain having different chemical properties. Specific examples may include substitution of the amino acid at position 433 by Ala (A), substitution of the amino acid at position 434 by Ala (A), and substitution of the amino acid at position 437 by Ala (A). In particular, a P protein in which the amino acids at all of these three sites have been substituted can be suitably used. As a result of these mutations, the temperature sensitivity of the P protein can be enhanced.

The temperature-sensitive mutations that can be included in the vector of the present invention are described in detail in WO 2012/029770, WO 2010/008054, and WO 2003/025570. Preferably, the P protein is a mutant P protein in which at least the amino acids at three sites, namely, D at position 433, R at position 434, and K at position 437, have been substituted by other amino acids. In addition, an F gene-deficient or F gene-deleted Sendai virus vector that encodes a mutant L protein in which at least L at position 1558 in the L protein has been substituted (preferably, a mutant L protein in which at least L at position 1361 has also been substituted by another amino acid), and an F gene-deficient or F gene-deleted Sendai virus vector having cytotoxicity at a level equal to or lower than the above-mentioned vector and/or temperature sensitivity at a level equal to or higher than the above-mentioned vector, are also suitably used in the present invention. The respective viral proteins may also have mutations in other amino acids (for example, ten or fewer, five or fewer, four or fewer, three or fewer, two or fewer, or one amino acid), in addition to the mutations described above. The vectors having mutations described above have high temperature sensitivity.

The genomic RNA included in the vector of the present invention may encode all of the envelope protein genes, or may not encode some or all of the envelope protein genes. The envelope protein genes that are encoded in the genomic RNA (M gene, F gene, and HN gene) may be of wild type, or may have temperature-sensitive mutations introduced thereinto. The temperature-sensitive mutations of the envelope proteins are described in detail in WO 2012/029770, WO 2010/008054, and WO 2003/025570.

At the time of producing a virus vector, when a desired exogenous envelope protein is expressed in a virus-producing cell, a virus vector containing this protein can be produced. There are no particular limitations on such a protein, and any desired proteins capable of imparting infectivity to mammalian cells, such as an adhesion factor, a ligand, and a receptor, are used. A specific example may be the G protein of vesicular stomatitis virus (VSV) (VSV-G). The VSV-G protein may be a protein derived from any arbitrary VSV strain, and for example, the VSV-G protein derived from the Indiana serotype strain (J. Virology 39: 5 19-528 (1981)) can be used; however, the example is not limited to this. The virus vector of the present invention can contain envelope proteins derived from other viruses in any arbitrary combinations.

Temperature sensitivity according to the present invention means that activity is significantly decreased at the conventional temperature for cell culture (for example, 37° C. to 38° C.) compared to the activity at a low temperature (for example, 30° C. to 36° C.). More preferably, temperature sensitivity means that activity is significantly decreased at 37° C. compared to the activity at 35° C. For example, in the case of an expression vector, a temperature-sensitive vector implies that the expression amount at the conventional temperature for cell culture (for example, 37° C. to 38° C.) is significantly low compared to the expression amount at a low temperature (for example, 30° C. to 36° C.). For example, the proliferation rate or gene expression level of the temperature-sensitive vector is, for example, ⅔ or less, preferably ½ or less, more preferably ⅓ or less, more preferably ⅕ or less, more preferably 1/10 or less, and more preferably 1/20 or less, at 37° C. compared to that at 35° C. Furthermore, the temperature-sensitive vector is such that the proliferation rate or gene expression level at 37° C. is, for example, ½ or less, more preferably ⅓ or less, more preferably ⅕ or less, more preferably 1/10 or less, and more preferably 1/20 or less, compared to that of a vector having wild type proteins. For example, mutations in Sendai virus, such as TS 7 (Y942H/L1361C/L1558I mutations in the L protein), TS 12 (D433A/R434A/K437A mutations in the P protein), TS 13 (D433A/R434A/K437A mutations in the P protein and L1558I mutation in the L protein), TS 14 (D433A/R434A/K437A mutations in the P protein and L1361C in the L protein), TS 15 (D433A/R434A/K437A mutations in the P protein and L1361C/L1558I mutations in the L protein), as described in detail in WO 2012/029770 and WO 2010/008054 are preferable temperature-sensitive mutations.

A specific example of the vector may be an F gene-deleted type Sendai virus vector (for example, Z strain) having G69E, T116A, and A183S mutations in the M protein; A262T, G264R, and K461G mutations in the HN protein; L511F mutation in the P protein; and N1197S and K1795E mutations in the L protein, and a vector obtained by further introducing a mutation of TS 7, TS 12, TS 13, TS 14, or TS 15 into the aforementioned vector is more preferred. Specifically, examples include SeV18+/TSΔF (WO 2010/008054 and WO 2003/025570), SeV (PM)/TSΔF, and vectors that have been modified so as to have microRNA target sequences added to the NP gene, P gene, or L gene in the vectors obtained by further introducing a mutation of TS 7, TS 12, TS 13, TS 14, or TS 15 into the aforementioned vectors. However, the examples are not limited to these.

Furthermore, "TSΔF" means a vector having G69E, T116A, and A183S mutations in the M protein; A262T, G264R, and K461G mutations in the HN protein; L511F mutation in the P protein; and N1197S and K1795E mutations in the L protein, and deletion of the F gene.

Preferably, the vector of the present invention is a Sendai virus vector derived from Sendai virus Z strain. The genomic sequence of the Z strain is known, and an example of the genomic sequence of a Z strain-derived F gene-deficient type Sendai virus vector may be ACCESSION: AB855655. Here, a vector being derived from Z strain means that the sequences of the Z strain occupy the highest proportion among the sequences of the Sendai virus genome in the genome of the vector. That is, it is implied that in a case in which non-Sendai virus type sequences (the sequence of a restriction enzyme recognition site or a simple spacer, a sequence derived from a virus of another species, the sequence of a gene to be introduced, and the like) are excluded and only the sequences of Sendai virus are collected from the genomic sequence of the vector, the sequences of the SeV Z strain occupy the highest proportion among the sequences. More preferably, a vector being derived from Z strain means that among the sequences derived from minus-strand RNA viruses available in the genome of the vector, the sequences of the SeV Z strain occupy the highest proportion. That is, it is implied that in a case in which sequences that are not sequences taken from minus-strand RNA viruses (the sequence of a restriction enzyme recognition site or a simple spacer, a sequence derived from a virus other than a minus-strand RNA virus, the sequence of a gene to be introduced, and the like) are excluded and only the sequences of minus-strand RNA viruses are collected from the genomic sequence of the vector, the sequences of the SeV Z strain occupy the highest proportion among the sequences. The proportion is preferably 30% or higher, more preferably 40% or higher, 50% or higher, 60% or higher, 70% or higher, 80% or higher, 90% or higher, 95% or higher, 96% or higher, 97% or higher, 98% or higher, or 99% or higher. Furthermore, preferably, a Sendai virus vector derived from the Z strain includes genomic sequences of Sendai viruses of non-Z strains (excluding sequences that are identical to those of the Z strain) in the genome such that, for example, only 1,000 or fewer consecutive bases, 500 or fewer consecutive bases, 300 or fewer consecutive bases, 200 or fewer consecutive bases, 100 or fewer consecutive bases, 50 or fewer consecutive bases, 30 or fewer consecutive bases, or 20 or fewer consecutive bases are included. More preferably, a Sendai virus vector derived from the Z strain does not include any genomic sequence of Sendai viruses of non-Z strains (excluding sequences that are identical to those of the Z strain) in the genome.

The vector of the present invention is preferably a vector that is not derived from Sendai virus CI. 151 strain (Yoshida, et al., (1979) Virology, 92, 139-154), and it is also preferable that the vector is not a chimeric vector obtained from the CI. 151 strain. The full-length gene cDNA of the CI. 151 strain is already known (Accession AB275416). Furthermore, the vector of the present invention is preferably a vector that is not derived from Sendai virus Nagoya strain, and is preferably not a chimeric vector obtained from the Nagoya strain.

The vector of the present invention is modified so as to have microRNA target sequences added to the NP gene, P gene, and/or L gene. Here, being modified so as to have a microRNA target sequence added to a gene means that the vector is modified so as to include a microRNA target sequence within a transcription region of the gene. Such a modification can be carried out by, for example, inserting a microRNA target sequence into a transcription region of the gene.

According to the present invention, there are no particular limitations on the microRNA target sequence to be added, and a target sequence for any desired microRNA can be added. Examples of such a microRNA target sequence include target sequences for a microRNA that is specifically expressed in cells in a particular differentiation state or cells in an undifferentiated state (pluripotent stem cells or the like), and a microRNA that is specifically expressed in cancer or a desired disease. Specific examples include, but are not limited to, the respective target sequences of let7, miR-7, miR-21, miR-106 a/b, miR-122, miR-124, miR-125, miR-126, miR-138, miR-130 a/b, miR-132, miR-143, miR-145, miR-155, miR-182, miR-199 a, miR-217, miR-218, miR-301, miR-302 cluster, miR-367, miR-372, miR-375, and miR-721. Here, the miR-302 cluster includes miR302a, miR302b, miR302c, and miR302d. The target sequences for these microRNAs are already well known (Mol Cell Biol. 2008, 28, 6426-6438). As disclosed in the Examples, it has been confirmed that the effects of the present invention are exhibited for all the microRNA target sequences that have been investigated, and it is possible to control vector expression by using a target sequence for a desired microRNA. For example, a target sequence for a microRNA other than miR-302a can also be suitably used.

For example, miR-126 is expressed in vascular endothelial cells (PNAS. 2008, 105, 1516-1521). Therefore, a vector for which the expression can be controlled vascular endothelial cell-specifically can be constructed by using a target sequence of miR-126. Furthermore, miR-124, miR-138, and miR-218 are expressed in nerve cells (Nature Cell Biol. 2009, 11, 705-716), and the expression of miR varies depending on the degree of differentiation of the cells (Mol Cell Biol. 2009, 29, 5290-5305). Therefore, a vector for which expression can be controlled nerve cell-specifically according to the stage of differentiation of cells can be constructed by using target sequences of miR-124, miR-138, and miR-218. Furthermore, miR-122 is expressed in liver cells (Science 2005, 309, 1577-1581). Therefore a vector for which expression can be controlled liver cell-specifically can be constructed by using a target sequence of miR-122. Furthermore, in ES/iPS cells, various microRNAs such as miR-367 are expressed in addition to the miR-302 cluster (PLoS One. 2013, 8, 73532). Therefore, a vector for which expression can be controlled ES/iPS cell-specifically can be constructed by using target sequences for miR-367 and the like, in addition to the miR-302 cluster. Furthermore, miR-143 is expressed in normal cells, and expression thereof is decreased in cancer cells (Oncol Rep. 2006, 16, 845-850). Therefore, a vector that is cancer cell-selectively expressed can be constructed by using a target sequence of miR-143.

A microRNA target sequence refers to a sequence to which a microRNA is bound as a target. Regarding the microRNA target sequence according to the present invention, a natural microRNA target sequence or a mutant thereof can be used as long as expression of the target sequence is suppressed by binding to a microRNA. Furthermore, the microRNA target sequence may be a sequence that is not completely complementary to the microRNA, and the microRNA target sequence includes at least 10 bases, for example, 11 or more bases, 12 or more bases, 13 or more bases, 14 or more bases, 15 or more bases, 16 or more bases, 17 or more bases, 18 or more bases, 19 or more bases, 20 or more bases, 21 or more bases, or 22 or more bases, which are complementary to the microRNA, consecutively or non-consecutively. Preferably, the complementary bases are consecutive or may have several, for example, five or fewer bases, four or fewer bases, three or fewer bases, two or fewer bases, or one base, which are not associated pairwise. The bases that are no associated pairwise may be included on the microRNA target sequence side and/or on the microRNA side.

A microRNA target sequence is a sequence that is hybridized with a microRNA under physiological conditions. The physiological conditions mean conditions including, for example, 150 mM NaCl, 15 mM sodium citrate, pH 7.0, and 37° C. More preferably, the microRNA target sequence is a sequence that is hybridized with a microRNA under stringent conditions. The stringent conditions mean conditions including, for example, 1×SSC (1×SSC means 150 mM NaCl, 15 mM sodium citrate, pH 7.0) or 0.5×SSC, and 42° C., more preferably conditions including 1×SSC or 0.5×SSC and 45° C., and more preferably conditions including 1×SSC or 0.5×SSC and 50° C. In regard to hybridization, for example, any one of RNA including a microRNA sequence and RNA including a microRNA target sequence is labeled, and if necessary, the other RNA is immobilized to a membrane or the like. Then, the two are hybridized. Regarding the conditions for hybridization, hybridization may be carried out in a solution including, for example, 5×SSC, 7% (W/V) SDS, 100 μg/ml denatured salmon sperm DNA, and 5×Denhardt solution (1×Denhardt solution includes 0.2% polyvinylpyrrolidone, 0.2% bovine serum albumin, and 0.2% ficoll), for example, at 37° C., or 45° C., or 50° C. After the system is incubated for a sufficient time (for example, 3, 4, 5, or 6 hours or longer), washing is performed under the conditions described above, and whether the labeled nucleic acid has been hybridized is detected. Thereby, it can be determined whether the nucleic acid is hybridized under the mentioned conditions.

Alternatively, a microRNA target sequence preferably shows high homology with a complementary sequence of a microRNA sequence. The term high homology means that base sequences having, for example, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 93%, at least 95%, at least 96', at least 97%, at least 98%, or at least 99% identity. The identity of base sequences can be determined by using, for example, the BLAST program (Altschul, S. F. et al., J. Mol. Biol. 215: 403-410, 1990). For example, retrieval can be performed in the webpage for the BLAST of NCBI (National Center for Biotechnology Information), using default parameters (Altschul S. F. et al., Nature Genet. 3:266-272, 1993; Madden, T. L. et al., Meth. Enzymol. 266:131-141, 1996; Altschul S. F. et al., Nucleic Acids Res. 25:3389-3402, 1997; and Zhang J. & Madden T. L., Genome Res. 7:649-656, 1997). For example, an alignment of two sequences is produced by the Blast2Sequences program (Tatiana A et al., FEMS Microbiol Lett. 174:247-250, 1999), which performs a comparison of two sequences, and the identity of the sequences can be determined. The outer gap of the base sequence of a complementary sequence of the microRNA sequence is neglected, and the inner gap is dealt with similarly to, for example, a mismatch. Thus, the value of identity for the whole base sequence (total length of bases obtained by adding the gaps incorporated on the inner side of the sequence) of a complementary sequence of the microRNA sequence in the alignment is calculated.

Alternatively, the microRNA target sequence preferably comprises a sequence obtained by subjecting the complementary sequence of the microRNA sequence to insertion, substitution, and/or deletion of one or several bases. Preferably, the microRNA includes a sequence having insertion, substitution, and/or deletion of eight or fewer bases, seven or fewer bases, six or fewer bases, five or fewer bases, four or fewer bases, three or fewer bases, two or fewer bases, or one base, with respect to a complementary sequence of the microRNA sequence.

Figure 13:
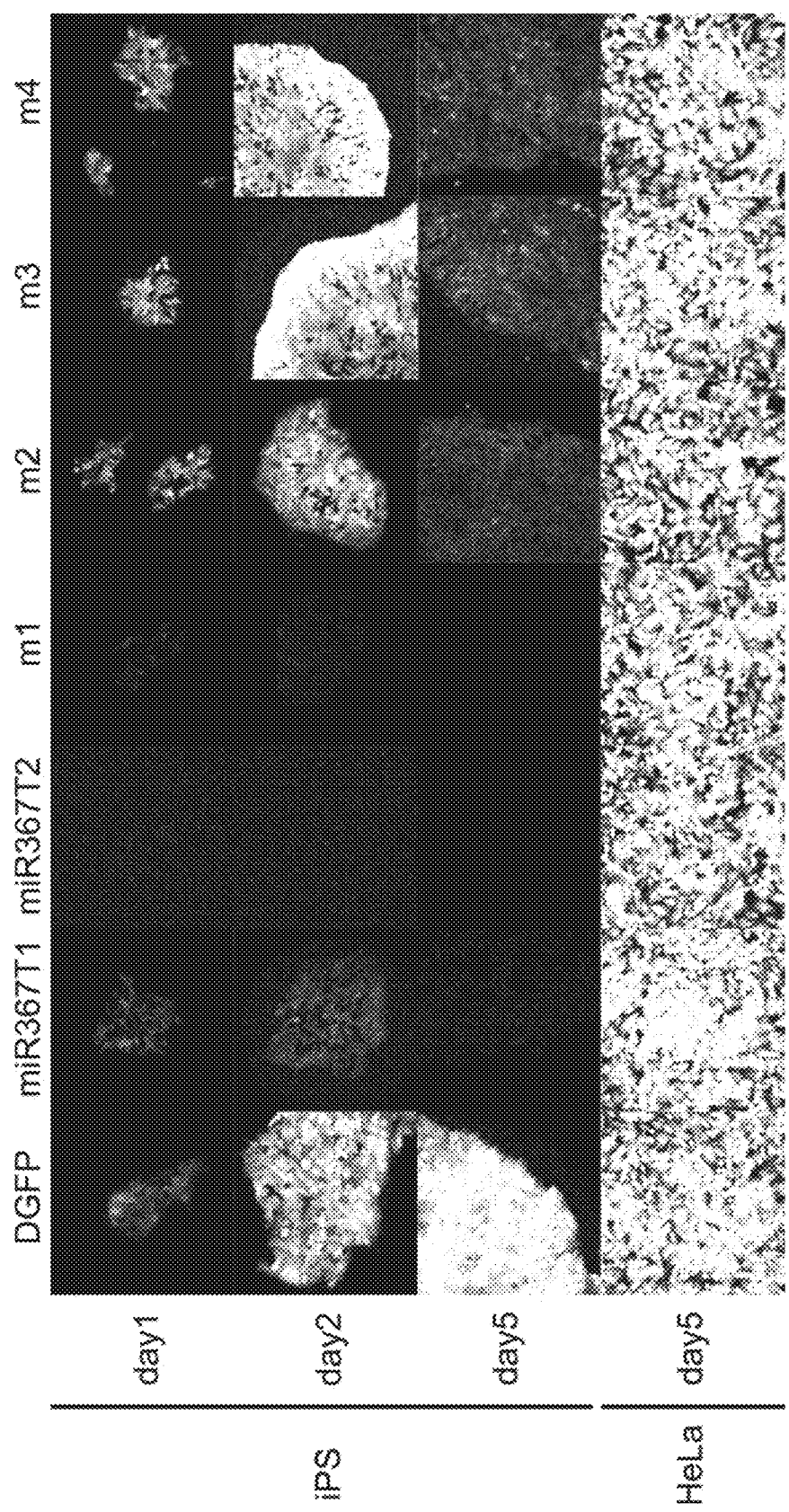
FIG. 13 is a set of diagrams showing the effect of introducing mutations into microRNA target sequences.
Figure 14:
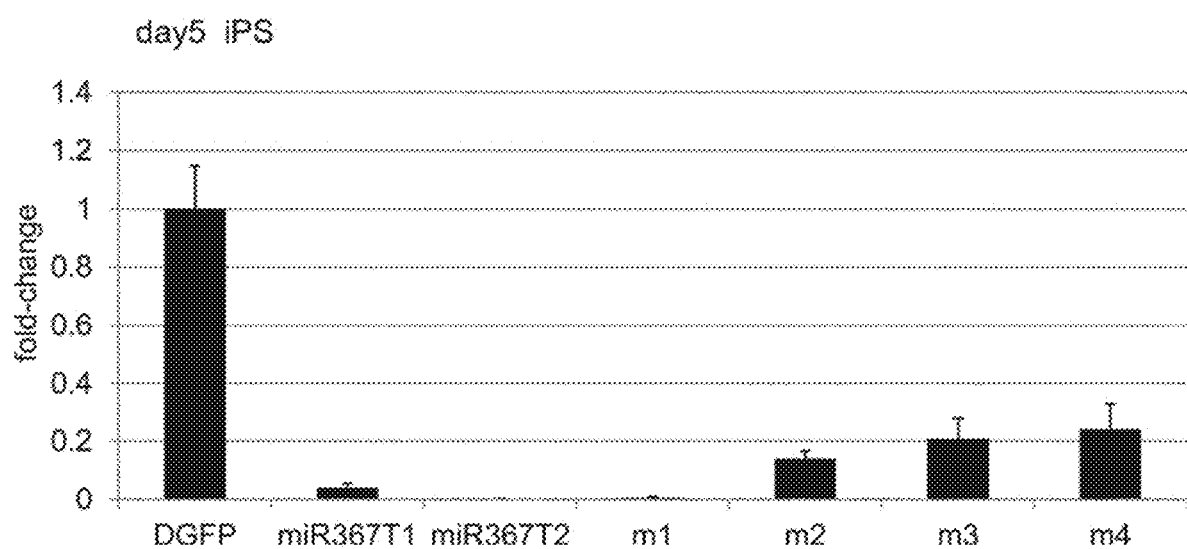
FIG. 14 is a diagram showing the effect of introducing mutations into microRNA target sequences. A comparison of fluorescence signals on Day 5 (analysis by MetaMorph) is shown. The intensity of the expression suppression effect provided by the miR367 target sequence was in the order of T2>T2 ml>T1>T2m2>T2m3>T2m4.

Generally, as more mutations are introduced into the microRNA target sequence, binding to the microRNA is suppressed, and the expression suppression effect is decreased (FIGS. 13 and 14). It is possible to regulate the suppression effect by introducing mutations as appropriate.

In the case of adding a microRNA target sequence to the NP gene, P gene, or L gene, there are no particular limitations on the position of addition, and the microRNA target sequence can be added to the coding region or non-coding region of each gene. In the case of adding the microRNA target sequence to the coding region, there are no limitations on the position, and the target sequence may be added at several positions in the region extending from the N-terminal site to the C-terminal site; however, it is preferable that, for example, the microRNA target sequence is added consecutively to the C-terminus. The non-coding region may be the 5'-non-coding region or the 3'-non-coding region; however, the 3'-non-coding region is preferred. In the case of adding the microRNA target sequence to the non-coding region, the position may be selected arbitrarily; however, for example, in a case in which a microRNA target sequence is added to the 3'-non-coding region of the NP gene and/or P gene, any position will be acceptable as long as the position is between the coding region of the gene to be added and the E (End) sequence. In a case in which the microRNA target sequence is added to the 5'-non-coding region, the target sequence can be added to, for example, a desired position between the S (Start) sequence of the gene to be added and the translation initiation site.

Furthermore, in the case of adding a microRNA target sequence to the L gene, the microRNA target sequence is added to a position as far as possible from the coding region. That is, expression level of the vector can be further increased by adding a microRNA target sequence to a position before the E sequence and near the trailer sequence of the genome. For example, the microRNA target sequence is added to a position far from the coding region by one or more bases, preferably 10 or more bases, 20 or more bases, 30 or more bases, 40 or more bases, 50 or more bases, or 56 or more bases.

Regarding the microRNA target sequence, one copy or a plurality of copies can be added. Furthermore, not only one kind of microRNA target sequence may be added, but also a plurality of kinds of microRNA target sequences may be added. For instance, for example, a sequence obtained by arranging two or more, for example, three or more, four or more, or five or more, of one kind or a plurality of kinds of microRNA target sequences in tandem, can be added.

In the case of modifying the P gene, when the expression of the C protein that is encoded in the nucleic acid in the coding region of the P protein is inhibited, the C protein may be expressed separately from the vector.

Regarding the P protein, it is acceptable not to use the full-length sequence, and appropriate fragments can be used. The region that is essential as the P protein is only a portion of the C-terminus, and the other regions are not essential for the expression of the virus vector. The P protein may be specifically a fragment maintaining a binding site for the L protein and a binding site for the N protein:RNA. Regarding the binding site for the L protein, examples include amino acid sequences from amino acid residue 411 to amino acid residue 445 of the SeV P protein, and regarding the N protein:RNA binding site, examples include amino acid sequences from amino acid residue 479 to amino acid residue 568 of the SeV P protein (for example, Accession Nos. AAB06197.1, P04859.1, P14252.1, AAB06291.1, AAX07439.1, BAM62828.1, BAM62834.1, P04860.1, BAM62840.1, BAD74220.1, P14251.1, BAM62844.1, BAM62842.1, BAM62842.1, BAF73480.1, BAD74226.1, BAF73486.1, Q9DUE2.1, BAC79134.1, NP_056873.1, and ABB00297.1). More specifically, for example, a fragment including an amino acid sequence from amino acid residue 320 to amino acid residue 568 of the SeV P protein can be suitably used as a functional P protein for the present invention. By using a deleted type P protein, the size of the vector can be reduced, and it can be expected that the vector be not easily affected by the immunoreactions of the host.

In the case of using a P protein in which the coding region of the C protein has been deleted, as described above, the C protein may be expressed separately as appropriate. Here, the C protein includes C' protein, C protein, Y1 protein, and Y2 protein (Irie T. et al., PLoS One. (2010) 5:e10719.). In order to express the C protein, the coding sequence of the C protein may be inserted into the vector as appropriate. There are no particular limitations on the position of insertion; however, the coding sequence can be inserted into a position immediately before the P protein (3'-side of the coding sequence of the P protein in the genome) or immediately after the P protein (5'-side of the coding sequence of the P protein in the genome). Upon the insertion, the E-I-S sequence may also be added as appropriate.

In a case in which a microRNA target sequence is added to the NP gene or P gene, when this microRNA is expressed in a cell into which the vector has been introduced, the expression level of the vector is decreased according to the expression of the microRNA, and the removal of the vector is promoted. For example, when a target sequence of a microRNA that is not expressed at the time of introducing the vector but is specifically expressed when the cell reaches a certain differentiation state (or undifferentiated state) is added to the vector, on the occasion that the vector has achieved its purpose, the expression is automatically expressed and removed. Furthermore, by applying the present invention to a temperature-sensitive vector, more rapid removal of the vector is made possible. For example, the vector of the present invention is preferably such that a temperature-sensitive P protein is encoded in the P gene. Specifically, a vector that includes L511F mutation in the P protein, or a vector having D433A/R434A/K437A mutations is preferred (WO 2012/029770 and WO 2010/008054). The vector may include both the L511F mutation and the D433A/R434A/K437A mutations, and the vector may further include other mutations in the P protein or other virus proteins. For example, the L gene encoding an L protein having L1361C/L1558I mutations as temperature-sensitive mutations can be suitably used.

The culturing period from the initiation of removal to the completion of removal may be appropriately determined; however, when the vector of the present invention is used, the vector is removed within, for example, four weeks, within three weeks, or within one week, for example, within 20 days, within 15 days, within 10 days, within 5 days, or within 3 days. This culturing period is, for example, 3 days to 3 weeks, 5 days to 20 days, or 5 days to 2 weeks. The removal of the virus can be confirmed by detecting a reporter gene or detecting the virus using an antibody or PCR, and thereby checking that the level of the reporter gene or the virus has decreased to a level equivalent to that in cells into which this virus is not introduced (or 1/100 or less, preferably 1/500 or less, 1/1,000 or less, or 1/5,000 or less, compared to the maximum value after virus introduction).

In the case of using a temperature-sensitive vector (vector encoding a protein including temperature-sensitive mutation), promotion of the removal of the vector can be carried out at, for example, 35° C. to 39° C. The promotion of the vector removal is carried out preferably at 36° C. to 38.5° C., and more preferably at about 37° C.

Meanwhile, in regard to a vector in which a microRNA target sequence has been added to the NP gene and/or P gene, it is preferable that a microRNA target sequence is not added to the L gene. That is, the present invention provides a modified Sendai virus vector, in which the NP gene and/or P gene of the virus has been modified such that a target sequence of microRNA Is added thereto, while no microRNA target sequence is added to the L gene of the virus, and in a cell expressing the microRNA added to the NP gene and/or P gene, the expression of the vector is negatively controlled. This vector is preferably a vector that is deficient in the F gene. This vector is preferably a vector derived from the Z strain.

Furthermore, it is preferable that the vector of the present invention does not have any functional F gene, M gene, and HN gene other than the F gene, M gene, and HN gene of the Z strain. That is, in a case in which the vector is not deficient in the F gene and has a functional F gene, it is preferable that this F gene is the F gene of the Z strain. In a case in which the vector is not deficient in the M gene and has a functional M gene, it is preferable that this M gene is the F gene of the Z strain. In a case in which the vector is not deficient in the HN gene and has a functional HN gene, it is preferable that this HN gene is the HN gene of the Z strain. It is also preferable for the vector of the present invention that the leader sequence and/or trailer sequence of the genome is also the sequence of the Z strain.

In a case in which a microRNA target sequence is added to the L gene, when this microRNA is expressed in a cell into which the vector has been introduced, the expression of the vector is increased according to the expression of the microRNA, and the genomic replication of the vector is also accelerated. Such a vector is useful for specifically expressing and/or expanding the vector in a cell expressing a particular microRNA. For example, a vector in which a target sequence for a microRNA that is expressed specifically in tumors has been added to the L gene, the expression is specifically accelerated in tumor cells. Therefore, it can be expected to destroy tumors specifically by loading a cytotoxic transgene into such a vector, or by imparting a cytotoxic effect to the vector itself.

For example, it is known that Sendai virus that is deficient in the M gene infiltrates into cells in the surroundings of the transduced cells and lyse the cells (WO 00/09700). In fact, it has been confirmed that when such a vector is injected into a tumor, the tumor cells are lysed, and the tumor size is reduced (WO 2003/093476). By applying the present invention to such a vector and specifically enhancing the expression of the vector in tumor cells, cells can be attached tumor-specifically while damage to non-cancer tissues in the surroundings is prevented. That is, a vector which is deficient in the M gene and has been modified such that a microRNA target sequence is added to the L gene, and expression of which is positively controlled by a microRNA carried by a cell, is useful for specifically lysing cells expressing that microRNA.

Such a vector has the F gene and the HN gene, and thereby, the vector can infiltrate into cells in the surroundings. That is, the present invention relates to an M gene-deficient minus-strand RNA virus vector that has been modified such that a microRNA target sequence is added to the L gene, the vector retaining the F gene and the HN gene. Such a vector does not have an ability to form infective virus particles but has an ability to infiltrate into cells adjacent to the cells into which the vector has been introduced (contact infiltration capability). The F protein may have the cleavage site of the F protein appropriately substituted by a sequence that serves as a substrate for other proteases, so that the F protein is activated by a protease specifically expressed in a target cell (WO 2003/093476).

Furthermore, when a target sequence of a microRNA that is expressed in normal cells but is not expressed or expressed to a reduced extent in cancer cells, is added to a paramyxovirus vector, a paramyxovirus vector which is expressed specifically in cancer cells while expression of the vector is suppressed, or the vector is eliminated, in normal cells, can be created. For example, the vector of the present invention in which a target sequence of a microRNA that is expressed in normal cells but is not expressed or is expressed to a reduced extent in cancer cells, has been added to the NP gene or P gene, is useful as a cancer-targeted vector. The present invention provides use of the vector of the present invention for cancer targeting, the vector being a vector in which a target sequence of a microRNA that is expressed in normal cells but is not expressed or is expressed to a reduced extent in cancer cells, has been added to the NP gene or P gene. Furthermore, the present invention provides a method for targeting cancer, the method including use of the vector of the present invention, in which a target sequence of a microRNA that is expressed in normal cells but is not expressed or is expressed to a reduced extent in cancer cells has been added to the NP gene or P gene. For example, when a suicide gene or a gene exhibiting cytotoxicity is loaded into that vector, cancer cells can be killed. The suicide gene is not particularly limited; however, for example, herpes virus-derived thymidine kinase gene (HSV-tk) can be used, and in this case, cells expressing HSV-tk can be killed by administering ganciclovir (GCV). The present invention provides use of the vector of the present invention for cancer therapy, the vector being a vector in which a target sequence of a microRNA that is expressed in normal cells but is not expressed or is expressed to a reduced extent in cancer cells has been added to the NP gene or P gene, and the vector carrying a suicide gene and/or a gene exhibiting cytotoxicity. Furthermore, the present invention provides a method for treating cancer, the method including use of the vector of the present invention, the vector being a vector in which a target sequence of a microRNA that is expressed in normal cells but is not expressed or is expressed to a reduced extent in cancer cells has been added to the NP gene or P gene, and the vector carrying a suicide gene and/or a gene exhibiting cytotoxicity.

Examples of the suicide gene loaded into the vector of the present invention include prodrug-converting enzyme genes for desired drugs exhibiting induction of cell death or cytotoxicity. Specific examples of a combination of a prodrug and a suicide gene include:

5-fluorocytosine and cytosine deaminase
cyclophosphamide and cytochrome P450
fludarabine and *Escherichia coli* PNP (purine-nucleoside phosphorylase)
CB1954 and nitroreductase
capecitabine and carboxylesterase.

Furthermore, regarding the suicide gene, a gene encoding a desired protein that exhibits induction of cell death or cytotoxicity by being converted from a non-active form to an active form, may be mentioned, and for example, a gene encoding a caspase that induces cell death can be suitably utilized. Specifically, a combination of a desired dimerizing agent and a caspase to which a binding domain of the dimerizing agent has been added, can be utilized, and an example of the combination of a dimerizing agent and a caspase may be:

AP20187 and iCaspase-9.

Furthermore, the above-mentioned vector that is deficient in the M gene does not have a particle forming ability; however, the vector has an ability of fusing cells in the surroundings through the function of the F gene. When a target sequence of a microRNA that is expressed in normal cells but is not expressed or is expressed to a reduced extent in cancer cells is added to this vector, a paramyxovirus vector that spreads infection in cancer cells while fusing the cancer cells and does not spread infection in normal cells, can be obtained. That is, the present invention provides use of the vector of the present invention for cancer targeting, the vector being an M gene-deficient vector in which a target sequence of a microRNA that is expressed in normal cells but is not expressed or is expressed to a reduced extent in cancer cells has been added to the NP gene or P gene. Furthermore, the present invention provides a method for targeting cancer, the method including use of the vector of the present invention, the vector being a vector in which a target sequence of a microRNA that is expressed in normal cells but is not expressed or is expressed to a reduced extent in cancer cells has been added to the NP gene or P gene. The present invention also provides use of the vector of the present invention for cancer therapy, the vector being an M gene-deficient vector in which a target sequence of a microRNA that is expressed in normal cells but is not expressed or is expressed to a reduced extent in cancer cells has been added to the NP gene or P gene. The present invention also provides a method for treating cancer, the method including use of the vector of the present invention, in which a target sequence of a microRNA that is expressed in normal cells but is not expressed or is expressed to a reduced extent in cancer cells has been added to the NP gene or P gene, and which is an M gene-deficient vector.

Generally, the F protein of a paramyxovirus is expressed as a precursor protein ($F_0$) and exhibits a fusion capability by being cleaved into $F_1$ and $F_2$ by a protease. When this protease-cleaved site is modified into an amino acid sequence that is cleaved by a protease which is expressed specifically in cancer cells, the F protein can be made to exhibit cell fusion activity specifically in cancer cells (WO 03/093476). By applying the present invention to an M gene-deficient type paramyxovirus vector in which the cleavage site of the F protein has been modified as such, a paramyxovirus vector that is rapidly eliminated in normal cells can be provided. That is, regarding the above-mentioned M gene-deficient vector, a vector carrying the F gene, in which the cleavage site of the F protein has been modified into an amino acid sequence cleavable by a protease that is expressed specifically in cancer cells, can be suitably used (see Example 17). Furthermore, when a suicide gene and/or a gene exhibiting cytotoxicity is loaded into this vector as described above, the anti-cancer effect can be further enhanced.

The present invention also provides a paramyxovirus vector carrying a plurality of P genes. In a case in which the control of vector expression or the control of vector elimination is carried out by decreasing the expression level of the P gene or lowering the activity or stability of the P protein, there is a possibility that the initial expression amount of the P gene may be too low, or the expression period of the P gene may be too short. According to the present invention, it was found that this problem can be solved by loading a plurality of P genes into a vector and suppressing the respective P genes.

By loading a plurality of P genes, the expression level of the P genes immediately after vector introduction can be increased, and consequently, the expression amounts of the carried genes can be increased. Furthermore, when the vector is controlled so as to suppress the expression of the respective P genes carried by the vector, expression of the P genes is suppressed, and expression of the carried genes from the vector is suppressed, so that elimination of the vector is promoted. The plurality of P genes may be subjected to suppression of expression in an identical manner, or may be subjected to suppression of expression in different manners. For example, in the case of loading two P genes into a vector, one of them is caused to encode a P protein having a temperature-sensitive mutation, while the other is caused to encode a non-temperature-sensitive P protein, and a microRNA target sequence can be added to the P gene encoding the non-temperature-sensitive P protein. In this case, the P protein expressed from one of the P genes can exhibit the function only at low temperature; however, the P protein expressed from the other P gene can exhibit its function even under non-low temperature conditions, while, instead, this P protein is subjected to suppression of expression by the microRNA. Thereby, the control of expression can be carried out in a more complicated and more richly flexible manner than in the case where only one P gene is carried.

It is also possible that one of the P genes is caused to encode a P protein having a degron added thereto, and a microRNA target sequence is added to the other P gene. In this case, the P protein expressed from one of the P genes is subjected to suppression by the degron, and the expression of the other P gene is subjected to suppression by the microRNA. The P protein having a degron added thereto may be modified into a temperature-sensitive P protein, and the P gene having a microRNA target sequence added thereto may be modified into a non-temperature-sensitive P protein. Meanwhile, when it is said that a degron has been added to the P gene, it means that this P gene encodes a P protein having a degron added thereto.

In regard to the induction of cell differentiation or reprogramming, when the above-described vector is constructed using a target sequence of a microRNA that is expressed in cells after induction, the expression of one of the P genes (P gene to which a target sequence of a microRNA has been added) is eliminated by the microRNA that is expressed in cells where reprogramming has been induced, and subsequently, the activity of the P protein that is expressed from the other P gene (P gene expressing a temperature-sensitive P protein or a P protein having a degron added thereto) is suppressed by temperature or the function of the degron. Thus, the vector is eliminated. By performing such dual regulation, the initial expression level or the expression period can be controlled more freely.

It is preferable that the carried P genes are modified such that expression can be suppressed compared to the wild type, and it is preferable that the P genes have modifications selected from, for example, temperature-sensitive mutation, addition of a degron, and addition of a target sequence of a microRNA. These may be used in any arbitrary combination. Preferably, it is preferable that a plurality of carried P genes is modified to be not completely identical to each other, and preferred examples include a vector carrying a P gene having a degron added thereto and a P gene having a microRNA target sequence added thereto; and a vector carrying a P gene encoding a temperature-sensitive mutant P protein and a P gene having a microRNA target sequence added thereto.

For example, when a plurality of P genes is loaded into a paramyxovirus vector, a paramyxovirus vector having excellent characteristics, by which the carried genes can be expressed at a sufficient level even if the cells into which the vector has been introduced are not cultured at low temperature, and after a predetermined effect is exhibited in the cells as a result of the expression of the carried genes, the vector can be rapidly removed from the cells, can be obtained. For example, in regard to the induction of iPS cells, a paramyxovirus vector having relatively high temperature sensitivity (particularly a paramyxovirus vector carrying a P gene having a temperature-sensitive mutation) has been conventionally used in order to rapidly remove the vector. In this case, since the vector is rapidly removed when culture is carried out at a conventional culturing temperature (for example, 37° C.), after the vector is introduced into cells, the cells needed to be cultured at a low temperature (for example, about 35° C.) for a certain time period, in order to express the carried genes in the cells.

This problem could be overcome by loading a plurality of P genes into a paramyxovirus vector. According to an embodiment of the present invention, the paramyxovirus vector carrying a plurality of P genes is such that at least one of the P genes to be carried is a non-temperature-sensitive P gene. For example, a paramyxovirus vector carrying two P genes may be such that the two P genes are both non-temperature-sensitive, or one of the P genes is temperature-sensitive while the other P gene is non-temperature-sensitive. A target sequence of a microRNA may be added to at least one of non-temperature-sensitive P genes, as described above. The other P gene can be imparted with temperature-sensitivity and/or addition of a degron.

There are no particular limitations on the genes to be loaded; however, in the case of a vector for inducing iPS cells, one or a plurality of desired reprogramming genes can be loaded as appropriate. Suitable examples of the genes to be carried include KOS (simultaneous loading of KLF4, SOX2 and OCT4) and MYC genes. A paramyxovirus vector carrying two or more P genes and carrying the KOS or MYC gene is useful for efficient induction of iPS cells. This vector carries at least one non-temperature-sensitive P gene, and a target sequence of a microRNA may be added to this non-temperature-sensitive P gene. Furthermore, the vector may also carry a P gene encoding a P protein to which a degron has been added, in addition to the non-temperature-sensitive P gene. Meanwhile, the reprogramming gene may be a gene into which a mutation has been introduced. For example, KLF4, SOX2, and OCT4 include not only wild type genes but also mutant type genes capable of inducing reprogramming. Furthermore, MYC includes cMYC, L-MYC, and mutants thereof.

Furthermore, a degron according to the present invention refers to a polypeptide that destabilizes a protein when added to the protein, and is well known to those skilled in the art. Examples of the degron include a sequence that is stabilized by binding to a low molecular weight compound, a sequence that is destabilized by binding with a low molecular weight compound, and a sequence that is destabilized irrespective of the presence or absence of a low molecular weight compound. Specific examples include an FKBP12-derived DD-tag (US 2009/0215169), which is known as mTOR protein; a dihydrofolate reductase (DHFR)-derived DDG-tag (US 2012/0178168), a TetR mutant (WO 2007/032555), a plant-derived auxin-inducible degron (AID) system (WO 2010/125620), the PEST sequence that is known as an auxilytic sequence (WO 99/54348), CL1 (WO 2004/025264), a calpain-derived sequence (JP 2009-136154 A), and NDS (JP 2011-101639 A). FKBP12 is known as a mammalian target of rapamycin (mTOR), and this is stabilized by binding to a low molecular weight compound such as rapamycin or shield1, is destabilized by removing the low molecular weight compound, and is degraded by proteasome. DHFR is stabilized by trimethoprim, and a TetR mutant is stabilized by doxycycline. The PEST sequence is a sequence rich in Pro, Glu, Ser, and Thr, and can be destabilized by adding, for example, the 422-461 sequence on the C-terminal side of mouse ornithine decarboxylase (mODC). The PEST sequence regulates the half-lives of proteins; however, a desired half-life reducing sequence can be used (Rechsteiner M, et al., Trends Biochem. Sci. 21, 267-271, 1996). The PEST sequence is a sequence in which, for example, both ends are surrounded by basic amino acids (H, K, or R), and the sequence includes (i) P, (ii) D and E, or (iii) S and E, and binds to ubiquitinating enzyme E3. The PEST sequence can be identified by, for example, GENETYX (Genetyx Corporation). Examples of a sequence capable of giving an effect similar to that of PEST include CL1, a calpain partial sequence, and NDS. An AID sequence is destabilized as TIR1, which is a plant ubiquitin ligase, binds to auxin (IAA).

According to the present invention, these degrons can be added to the P protein, and specific preferred examples of degron include mTOR degron, DHFR degron, TetR degron, PEST, and AID. Furthermore, these degrons include natural sequences and sequences derived therefrom. Particularly preferred examples of the degron include mTOR degron, DHFR degron, TetR degron, and PEST, and above all, degrons other than the AID sequence are preferred. Specifically, FKBP12 degron (DD), DHFR degron (DDG), TetR degron, and mODC PEST are preferred. Regarding the PEST, d2 derived from a natural sequence, and d1 and d4, which are modifications thereof, are known (WO 99/54348); however, these are all include in the PEST and can be used in the present invention (see Examples).

Specific examples of preferred degron sequences will be listed below.

mODC PEST sequence (WO 99/54348)

d2tag:mODC422-461: 422-462 on the C-terminal side of ACCESSION: P00860 (SEQ ID NO:58) (DNA: SEQ ID NO:57)

d4tag:mODC422-461 (T436A) (SEQ ID NO:59)

d1tag:mODC422-461 (E428A/E430A/E431A) (SEQ ID NO:60)

Furthermore, other mutants described in WO 99/54348 may also be used. Specifically, $MODC_{376-461}$, $MODC_{376-456}$, and $MODC_{422-461}$ described in WO 99/54348 (SEQ ID NO:58); P426A/P427A, P438A, E428A/E430A/E431A, E444A, S440A, S445A, T436A, D433A/D434A, and D448A, which are mutant sequences with respect to $MODC_{422-461}$; and sequences containing combinations of those mutations, may be listed as suitable PEST sequences. Furthermore, polypeptides that include amino acid sequences obtained by subjecting the above-mentioned amino acid sequences to substitution, deletion, and/or addition of one or a plurality of amino acids and have an activity of destabilizing proteins, may also be used. Particularly preferred sequences include MODC422-461 (SEQ ID NO:58) and a mutant thereof, mODC422-461 (T436A) (SEQ ID NO:59). Furthermore, P438A, S440A, and the like can also be suitably used for the present invention.

Sequence of DD-tag (US 2012/0178168) DD-tag:FKBP (L106P): mutant of ACCESSION:NP_000792 (F37V/L107P) (SEQ ID NO:62) (DNA: SEQ ID NO:61) Other mutants described in US 2012/0178168 may also be used. In US 2012/017816, a mutant is described as L106P without counting the Met on the N-terminal side, and this mutation is located at the same position as L107P of NP_000792.

Specific examples include the sequence of amino acids 2-108 of ACCESSION: NP_000792 ($FKBP_{2-108}$) (SEQ ID NO:92) and mutants thereof, and those mutants include sequences containing F36V, F15S, V24A, H25R, E60G, L106P, D100G, M66T, R71G, D100N, E102G, K105I (all representing the position where the second amino acid is regarded as residue "1" without counting the Met on the N-terminal side), and combinations of those mutations. Furthermore, polypeptides that include amino acid sequences obtained by subjecting these amino acid sequences to substitution, deletion, and/or addition of one or a plurality of amino acids and have an activity of destabilizing proteins, may also be used.

Sequence of DDG-tag (US 2012/0178168)

DDG-tag:DHFR (H12L/Y100I): mutant (R12L/G67S/Y100I) (SEQ ID NO:66) of ACCESSION: B7MAH1 [UniParc] (SEQ ID NO:65) (DNA: SEQ ID NO:64)

Other mutants described in US 2012/0178168 may also be used. Specific examples include the amino acid sequence of DFHR protein (ACCESSION: B7MAH1, SEQ ID NO:64) and mutants thereof. Examples of the mutants include sequences containing N18T/A19V, F103L, Y100I, G121V, H12Y/Y100I, H12L/Y100I, R98H/F103S, M42T/H114R, I61F/T68S, and combinations of those mutations. Furthermore, polypeptides that include amino acid sequences obtained by subjecting these amino acid sequences to substitution, deletion, and/or addition of one or a plurality of amino acids and have an activity of destabilizing proteins, may also be used. Meanwhile, the first amino acid Met may be omitted.

Sequence of TetR-Tag (WO 2007/032555)

TetR-tag: mutant (R28Q/D95N/L101S/G102D) (SEQ ID NO:69) of TetR (R28Q/D95N/L101S/G102D): ACCESSION: NP_941292 (SEQ ID NO:68) (DNA: SEQ ID NO:67)

Furthermore, other mutants described in WO 2007/032555 may also be used. Specific examples include the amino acid sequence of TetR protein (ACCESSION: NP_941292, SEQ ID NO:68) and mutants thereof. Examples of the mutants include sequences containing D95N, L101S, G102D, and combinations of those mutations. The mutants may further contain the mutation of R28Q. Furthermore, polypeptides that include amino acid sequences obtained by subjecting these amino acid sequences to substitution, deletion, and/or addition of one or a plurality of amino acids and have an activity of destabilizing proteins, may also be used. Meanwhile, the first amino acid Met may be omitted.

A nucleic acid encoding a degron can be produced as appropriate by DNA synthesis. A natural degron sequence can be separated by performing a hybridization method under stringent conditions using a DNA encoding the degron sequence described above (for example, SEQ ID NO:57, 61, 64, or 67) or a complementary sequence thereof as a probe. Stringent hybridization conditions can be appropriately selected by any person ordinarily skilled in the art. For example, hybridization can be carried out using the washing liquid and temperature conditions described in the present specification. A polynucleotide isolated by utilizing such a hybridization technology, or a polypeptide encoded by the polynucleotide usually has high homology with the polynucleotide used as a probe or a polypeptide encoded by the polynucleotide, in the base sequence and the amino acid sequence, respectively. High homology indicates sequence identity of at least 70% or higher, more preferably 80% or higher, more preferably 90% or higher, more preferably at least 95% or higher, more preferably at least 97% or higher (for example, 98% or higher, or 99% or higher). The sequence identity can be determined by, for example, the algorithm BLAST developed by Karlin and Altschul (Proc. Natl. Acad. Sci. USA 87:2264-2268, 1990 and Proc. Natl. Acad. Sci. USA 90:5873-5877, 1993). In the case of analyzing a sequence using BLAST (Altschul et al., J. Mol. Biol. 215:403-410, 1990), which was developed based on that algorithm, various default parameters of the program are used. Specific techniques for these analysis methods are known (www.ncbi.nlm.nih.gov). In the case of modifying an amino acid sequence, the amino acids to be modified preferably range from one to several amino acids, and more preferably one to ten, one to eight, one to five, one to four, one to three, or one to two amino acids.

A degron can be added as appropriate to a desired position of the P protein, and for example, a degron can be added to the N-terminus or the C-terminus of the P protein. In a case in which a degron is added to the N-terminal of the P protein, and expression of the C protein encoded in the nucleic acid within the coding region of the P protein is inhibited, the C protein may be expressed separately from the vector. In a case in which not the full-length P protein but a fragment is used as the P protein, and this fragment does not contain the coding region for the C protein, a degron can be added to any arbitrary position at the N-terminus or the C-terminus. In the present invention, a degron is preferably added to the C-terminal side of the P protein. A modified P protein having a degron added thereto can be produced by a well-known method. Specifically, a sequence encoding a degron may be inserted into the sequence of a viral genome encoding the P protein while ensuring that the reading frame is consistent.

Furthermore, as described above, while it may not be necessary to use the full-length P protein, an appropriate fragment can be used. The only essential part as the P protein is a portion of the C-terminus, and the other regions are not essential for the expression of the virus vector. The P protein may be specifically a fragment retaining the binding site to the L protein and the binding site to the N protein:RNA. The binding site to the L protein may be, for example, the amino acid sequence from amino acid residue 411 to amino acid residue 445 of the SeV P protein, and the binding site to the N protein:RNA may be, for example, the amino acid sequence from amino acid residue 479 to amino acid residue 568 of the SeV P protein (for example, accession Nos. AAB06197.1, P04859.1, P14252.1, AAB06291.1, AAX07439.1, BAM62828.1, BAM62834.1, P04860.1, BAM62840.1, BAD74220.1, P14251.1, BAM62844.1, BAM62842.1, BAM62842.1, BAF73480.1, BAD74226.1, BAF73486.1, Q9DUE2.1, BAC79134.1, NP_056873.1, and ABB00297.1). More specifically, for example, a fragment containing the amino acid sequence from amino acid residue 320 to amino acid residue 568 of the SeV P protein can be suitably used as a functional P protein for the present invention. When a deleted type P protein is used, the size of the vector can be reduced, and it can be expected that the vector be not easily affected by the immunoreactions of the host.

In the case of using a P protein in which the coding region of the C protein has been deleted, as described above, the C protein may be expressed separately as appropriate. Here, the C protein includes C', C, Y1, and Y2 proteins (Irie T. et al., PLoS One. (2010) 5:e10719). In order to express the C protein, the coding sequence of the C protein may be inserted into the vector as appropriate. There are no particular limitations on the position of insertion; however, the coding sequence can be inserted into a position immediately before the P protein (3'-side of the coding sequence of the P protein in the genome) or immediately after the P protein (5'-side of the coding sequence of the P protein in the genome). Upon the insertion, the E-I-S sequence may be added as appropriate.

According to the present invention, a vector in which a degron has been added to the P protein, particularly a vector in which a degron has been added to a temperature-sensitive P protein, specifically has D433A/R434A/K437A mutations in the P protein (WO 2012/029770 and WO 2010/008054), and the degron is DD-tag, DDG-tag, TetR-tag, the PEST sequence of mODC, or a mutant thereof having a different rate of degradation (WO 99/54348). More preferably, the vector has L1361C/L1558I mutations in the L protein as temperature-sensitive mutations.

Low-temperature culture according to the present invention refers to culturing at a temperature lower than 36.5° C. Preferably, low-temperature culture refers to culturing at a temperature lower than 36.4° C., more preferably 36.3° C., 36.2° C., 36.1° C., 36° C., 35.9° C., 35.8° C., 35.7° C., 35.6° C., 35.5° C., 35.4° C., 35.3° C., 35.2° C., 35.1° C., and more preferably lower than 35° C. The lower limit is, for example, 30° C., preferably 31° C., and more preferably 32° C., 33° C., or 34° C. Furthermore, about 37° C. as used in the present invention refers specifically to 36.5° C. to 37.5° C., preferably 36.6° C. to 37.4° C., and more preferably 36.7° C. to 37.3° C.

After the vector of the present invention is introduced and an intended gene is expressed, the vector can be removed as appropriate according to the characteristics of the degron. For example, in the case of using a ligand-controllable degron such as DD, DDG or TetR mutant, if a ligand is no added, removal is accelerated; however, expression of the vector can be prolonged by adding a ligand such as Shield-1. Furthermore, when a degron that exhibits its function even without a ligand as in the case of the PEST sequence is used, the removal of the vector can be accelerated by continuing the culture of cells into which the vector has been introduced. The culture period from the initiation of removal to the completion of removal may be determined as appropriate; however, when the vector of the present invention is used, the vector is removed within, for example, four weeks, within three weeks, within two weeks, or within one week, for example, within 20 days, within 15 days, within 10 days, within 5 days, or within 3 days. This culture period is, for example, 3 days to 3 weeks, 5 days to 20 days, or 5 days to 2 weeks. The removal of the virus can be confirmed by detecting a reporter gene or detecting the virus using an antibody or PCR, and thereby checking that the level of the reporter gene or the virus has decreased to a level equivalent to that in cells into which this virus is not introduced (or 1/100 or less, preferably 1/500 or less, 1/1,000 or less, or 1/5,000 or less, compared to the maximum value after virus introduction).

Production of the minus-strand RNA virus vector of the present invention may be carried out by utilizing a known method. Regarding the specific procedure, the minus-strand RNA virus vector can be produced typically by (a) a step of transcribing a cDNA encoding the minus-strand RNA virus genomic RNA (minus strand) or a complementary strand thereof (plus strand) in a cell that expresses viral proteins (NP, P, and L) necessary for virus particle formation; and (b) a step of collecting the virus thus produced. The virus is not limited to infective particles, and non-infective particles, RNP, and the like are also included in the definition of virus, as long as an ability of expressing a gene when introduced into a cell is retained. The viral proteins necessary for virus formation may be expressed from the transcribed viral genome RNA or may be supplied from sources other than genomic RNA. For example, viral proteins can be supplied by introducing expression plasmids encoding the NP, P, and L proteins into cells. When viral genes necessary for virus formation are lacking in the genomic RNA, those viral genes can be separately expressed in virus-producing cells, and thereby virus formation can be complemented. In order to express a viral protein or RNA genome in cells, a vector in which a DNA encoding that protein or genomic RNA is linked downstream of an appropriate promoter that functions in a host cell is introduced into the host ell. The genomic RNA thus transcribed is replicated in the presence of viral proteins, and virions are formed. When a defective type virus that is deficient in genes such as the genes of the envelope proteins is produced, the missing proteins, other viral proteins that can complement the function of those missing proteins, and the like can be expressed in virus-producing cells. According to the present invention, a vector in which at least the F gene has been deleted, or a vector having a mutation in the F gene can be suitably used.

The RNP of the present invention can be produced by transcribing the genomic RNA (positive-strand or negative-strand) included in the vector of the present invention in the presence of the NP, P, and L proteins. The formation of RNP can be carried out in, for example, BHK-21 or LLC-MK2 cells. Regarding the supply of the NP, P, and L proteins, the proteins may be supplied by virus vectors or may be supplied by other various methods. For example, the supply of the proteins may be carried out by introducing expression vectors encoding the respective genes into cells as described above. Furthermore, the respective genes may be incorporated into the chromosome of the host cell. It is not necessary for the NP, P and L genes that are expressed for forming RNP to be completely identical to the NP, P, and L genes that are encoded in the genome of the vector. That is, regarding the amino acid sequences of the proteins encoded by these genes, even though those amino acid sequences are not identical to the amino acid sequences of the proteins encoded by RNP genome, as long as the NP, P, and L proteins bind to the genomic RNA and exhibit transcription and replication activity for the genome in the cells, mutations may be introduced into the genes, or homologous genes of other viruses may be used as substitutes. It is also acceptable that wild type proteins (wild-type NP, P, and/or L proteins) are expressed.

In the case of a vector deficient in the envelope protein genes, when envelope proteins such as the F, HN, and/or M proteins are expressed in cells at the time of reconstituting the vector in the cells, these proteins are incorporated into the virus vector, and a virus vector maintaining infectiousness can be produced. Once such a vector infects cells, although the vector can express proteins from the genomic RNA due to the function of the RNP introduced into the cells, the vector itself cannot express envelope proteins, and therefore, infective virus particles cannot be formed. Also, since microRNA target sequences have been added, the expression of the vector can be controlled dependently by the expression of the microRNAs. Such a vector is very useful for the modification of cells, particularly when the vector carries transcription factor genes. For example, by loading a gene encoding a desired differentiation factor or a dedifferentiation factor into the vector of the present invention having a microRNA target sequence added thereto, differentiation or dedifferentiation of cells can be induced efficiently and/or specifically.

For example, the production of the minus-strand RNA virus of the present invention can be carried out by utilizing the following conventional methods (WO 97/16539; WO 97/16538; WO 00/70055; WO 00/70070; WO 01/18223; WO 03/025570; WO 2005/071092; WO 2006/137517; WO 2007/083644; WO 2008/007581; Hasan, M. K. et al., J. Gen. Virol. 78: 2813-2820, 1997, Kato, A. et al., 1997, EMBO J. 16: 578-587, and Yu, D. et al., 1997, Genes Cells 2: 457-466; Durbin, A. P. et al., 1997, Virology 235: 323-332; Whelan, S. P. et al., 1995, Proc. Natl. Acad. Sci. USA 92: 8388-8392; Schnell. M. J. et al., 1994, EMBO J. 13: 4195-4203; Radecke, F. et al., 1995, EMBO J. 14: 5773-5784; Lawson, N. D. et al., Proc. Natl. Acad. Sci. USA 92: 4477-4481; Garcin, D. et al., 1995, EMBO J. 14: 6087-6094; Kato, A. et al., 1996, Genes Cells 1: 569-579; Baron, M. D. and Barrett, T., 1997, J. Virol. 71: 1265-1271; Bridgen, A. and Elliott, R. M., 1996, Proc. Natl. Acad. Sci. USA 93: 15400-15404; Tokusumi, T. et al. Virus Res. 2002: 86; 33-38, and Li, H.-O. et al., J. Virol. 2000: 74; 6564-6569). Furthermore, regarding the methods for proliferation of viruses and the methods for production of recombinant viruses, see also "Uirusu-gaku Jikken-gaku Kakuron (Detailed Virology Experimens) ", 2$^{nd}$ revised edition (edited by the National Institute of Infectious Diseases, Student's Association, Maruzen Co. Ld., 1982).

In regard to the construction of the vector of the present invention, when the expression of a viral gene to which a microRNA target sequence has been added is decreased, preferably, production is carried out using cells that express the gene separately (helper cells). For example, in a case in which the gene to which a microRNA target sequence has been added is the P gene, P protein-expressing cells may be used. Also, in a case in which such a vector is a vector that is also deficient in the F gene, the production may be carried out using cells that express the P protein and the F protein (PF-expressing cells).

The vector of the present invention can carry desired genes. There are no particular limitations on the genes to be carried, and any desired exogenous gene (gene which the vector originally does not have) can be loaded. There are no particular limitations on the number of exogenous genes to be loaded, and one, two, or more genes can be loaded. An exogenous gene may have an appropriate microRNA target sequence added thereto.

In regard to the vector of the present invention, an exogenous gene can be generally inserted at a position immediately before (3'-side of the genome) or immediately after (5'-side of the genome) of any of the viral genes (for example, NP, P, M, F, HN, and L). The exogenous gene may be disposed between the Sendai virus S (Start) sequence and the E (End) sequence as appropriate. The S sequence is a signal sequence for initiating transcription, and the E sequence terminates the transcription. A region disposed between the S sequence and the E sequence becomes a single transcription unit. A sequence that serves as a spacer (intervening sequence) can be inserted as appropriate into any position between the E sequence of a certain gene and the S sequence of the next gene.

Regarding the S sequence, any desired S sequence of Sendai virus can be used; however, the sequence of 3'-UCCCWVUUWC-5' (W=A or U; and V=A, C, or G) (SEQ ID NO:1) can be suitably used. In particular, 3'-UCCCAGUUUC-5' (SEQ ID NO:2), 3'-UCCCAC-UUAC-5' (SEQ ID NO:3), and 3'-UCCCACUUUC-5' (SEQ ID NO:4) are preferred. When these sequences are presented as DNA sequences encoding the plus-strands, the DNA sequences are 5'-AGGGTCAAAG-3' (SEQ ID NO:5), 5'-AGGGTGAATG-3' (SEQ ID NO:6), and 5'-AGGGT-GAAAG-3' (SEQ ID NO:7), respectively. Regarding the E sequence of the Sendai virus vector, for example, 3'-AUUC-UUUUU-5' (5'-TAAGAAAAA-3' in the DNA encoding the plus-strand) is preferred. The I sequence may be, for example, any arbitrary trinucleotide, and specifically, 3'-GAA-5' (5'-CTT-3' in the plus-strand DNA) may be used.

The vector of the present invention can be applied to the production of pluripotent stem cells by loading genes that encode reprogramming factors such as transcription factors, and the removal of the vector at that time can be promoted. For example, in WO 2012/029770 and WO 2010/008054, cMYC is carried by a temperature-sensitive TS15 vector; however, by loading and substituting this into the vector of the present invention, when pluripotent stem cells are produced using KLF4, OCT4, SOX2, and cMYC, removal of the vector can be promoted. Regarding the transcription factors to be used at the time of producing pluripotent stem cells, molecules other than the above-mentioned molecules, such as L-MYC, Glis1, Lin28, and NANOG, may be used. A transcription factor gene to be carried by the vector may be modified as appropriate. For example, when one or more, preferably two or more, three or more, four or more, or all the five mutations selected from the group consisting of a378g, t1122c, t1125c, a1191g, and a1194g are introduced into wild type cMYC, genes can be stably expressed at high level from the vector (for example, SEQ ID NO:45 described in WO 2010/008054).

The present invention provides use of the vector of the present invention for the reprogramming of cells, and more specifically, use for the production of induced pluripotent stem cells, the vector being a vector having a microRNA target sequence added to the NP gene or P gene and carrying the KOS or MYC gene. Furthermore, the present invention provides a method for producing induced pluripotent stem cells by using the vector of the present invention, in which a microRNA target sequence has been added to the NP gene or P gene and carries the KOS or MYC gene.

This vector may have a microRNA target sequence added to the NP gene or P gene; however, it is preferable that a microRNA target sequence is added to the P gene, and it is more preferable that a microRNA target sequence is added to the 3'-non-coding region of the P gene (5'-side of the coding region on the genome). There are no particular limitations on the loading position of the KOS or MYC gene; however, for example, in the case of the KOS gene, it is preferable that the gene is loaded upstream of the M gene (that is, 3'-side of the M gene on the genome, for example, between the P gene and the M gene), and in the case of the MYC gene, it is preferable that the gene is loaded upstream of the L gene (that is, 3'-side of the L gene on the genome, for example, between the HN gene and the L gene). Furthermore, this vector preferably has the F gene deleted therefrom. An F gene-deleted type paramyxovirus vector in which a microRNA target sequence has been added to the 3'-non-coding region of the P gene and the KOS or MYC gene is carried, is very useful for efficient induction of reprogramming.

It is also preferable that KLF4 is expressed by using the vector of the present invention. For example, the vector of the present invention, in which a microRNA target sequence has been added to the NP gene or P gene and the KLF4 gene is carried, is useful as a vector for the induction of iPS cells. The present invention provides use of the vector of the present invention for the reprogramming of cells, and more specifically, for the production of induced pluripotent stem cells, the vector being a vector having a microRNA target sequence added to the NP gene or P gene and carrying the KLF4 gene. The present invention also provides a method for producing induced pluripotent stem cells by using the vector of the present invention, the vector being a vector having a microRNA target sequence added to the NP gene or P gene and carrying the KLF4 gene. By using the vector of the present invention, the formation of colonies of pluripotent stem cells can be promoted, as compared to the case of using a control vector that does not have a target sequence of a microRNA added thereto. Here, the promotion of the formation of colonies of pluripotent stem cells may be an enhancement of the colony formation efficiency and/or promotion of the growth of the colonies, and preferably promotion of the growth of the colonies. For example, whether the growth of colonies has been expedited can be investigated by measuring the size of ALP-positive colonies. Furthermore, even if the colony formation promoting effect is disregarded, when the vector of the present invention is used, the vector can be removed rapidly after the induction of iPS cells.

In this vector, it is desirable that a microRNA target sequence is added to the NP gene or P gene; however, it is preferable that a microRNA target sequence is added to the P gene, and it is more preferable that a microRNA target sequence is added to the 3'-non-coding region of the P gene (5'-side of the coding region on the genome). There are no particular limitations on the loading position of the KLF4 gene; however, for example, it is preferable that the KLF4 gene is carried downstream of the NP gene (that is, between the NP gene and the P gene), or upstream of the NP gene (that is, between the leader sequence and the NP gene). Furthermore, this vector preferably has the F gene deleted therefrom. An F gene-deleted type paramyxovirus vector in which a microRNA target sequence has been added to the 3'-non-coding region of the P gene, and the KLF4 gene is carried between the leader sequence and the NP gene, is very useful for efficient induction of reprogramming.

Regarding the microRNA target sequence, for example, a target sequence of a desired microRNA that is specifically expressed in induced pluripotent stem cells can be used, and specifically, a target sequence of miR-302 or miR-367 can be used; however, the invention is not limited to those. Furthermore, in regard to the target sequence, a plurality of copies can be used, or the suppressive action can be regulated by introducing an appropriate mutation into the target sequence.

The gene encoding a reprogramming factor for inducing pluripotent stem cells is not particularly limited as long as it is a gene capable of functioning so as to induce reprogramming, and examples include a gene that is specifically expressed or is expressed at high level in ES cells; a gene encoding a factor that is activated by the Wnt signal or the LIF signal; a gene essential for the sustenance of differentiation/pluripotency of ES cells; genes causing the expression of endogenous Oct3/4 gene and Nanog gene when introduced from the genes of those families into somatic cells; and combinations thereof (WO 2007/069666; JP 5467223). Specific examples include, as described above but are not limited to, KLF4, OCT4, SOX2, cMYC, L-MYC, Glis1, Lin28, and NANOG.

The pluripotent stem cells according to the present invention refer to stem cells produced from the inner cell mass of an embryo in the blastocyst stage of an animal, or cells having phenotypes similar to those cells. Specifically, the pluripotent stem cells induced in the present invention are cells that express alkaline phosphatase, which is an indicator of ES-like cells. Here, ES-like cells refer to pluripotent stem cells having properties and/or forms similar to those of ES cells. Preferably, pluripotent stem cells form, when cultured, flat colonies comprising cells having a higher volume proportion of nucleus than cytoplasm. Culturing may be carried out together with a feeder as appropriate. Furthermore, while cultured cells such as MEF stop proliferation in a few weeks, pluripotent stem cells can be subcultured for a long time period, and this can be confirmed from the fact that the proliferation properties are not lost even if the cells are passaged, for example, 15 or more times, preferably 20 or more times, 25 or more times, 30 or more times, 35 or more times, or 40 or more times. Furthermore, pluripotent stem cells preferably express endogenous NANOG. Pluripotent stem cells preferably express TERT and exhibit telomerase activity (activity of synthesizing a telomeric repeat sequence). Furthermore, pluripotent stem cells preferably have a capability of differentiating into three germ layers (endoderm, mesoderm, and ectoderm) (for example, this can be confirmed during teratoma formation and/or embryoid body formation). More preferably, pluripotent stem cells produce germline chimeras when transplanted into blastocysts. Pluripotent stem cells capable of germline transmission are referred to as germline-competent pluripotent stem cells. Confirmation of these phenotypes can be carried out by well-known methods (WO 2007/69666; Ichisaka T. et al., Nature 448(7151):313-7, 2007). Also, it is also possible to cause differentiation of desired cells or tissues by loading differentiation inducing factor genes into the vector of the present invention, and introducing the vector into undifferentiated cells, stem cells, or the like.

Cells produced by introducing the vector of the present invention are useful for causing differentiation of various tissues or cells, and the cells can be used in desired tests, studies, diagnoses, examinations, treatments, and the like. For example, induced stem cells are expected to be utilized in stem cell therapy. For example, reprogramming is induced using somatic cells collected from a patient, and then somatic stem cells or other somatic cells obtainable by inducing differentiation can be transplanted into the patient. The method for inducing cellular differentiation is not particularly limited, and for example, differentiation can be induced by retinoic acid treatment, treatment with a variety of growth factors/cytokines, and treatment using hormones. The cells thus obtained can be used for detecting the effects of a desired drug or compound, and screening of drugs or compounds can be carried out through this use. The present invention can be used for medical uses and for non-medical uses, and is useful in medical and non-medical embodiments. For example, the present invention can be used for therapeutic, surgical, and/or diagnostic purposes, or non-therapeutic, non-surgical, and/or non-diagnostic purposes.

There are no particular limitations on the cells into which the vector is introduced, and the cells may be differentiated somatic cells or may be somatic stem cells or germ stem cells such as hematopoietic stem cells, neural stem cells, mesenchymal stem cells, hepatic stem cells, and skin epidermal stem cells. The cells may be derived from, for example, cells of embryos, fetuses, infants, children, adults, or aged people. There are no particular limitations on the animal origin, and mammals including humans and non-human primates (monkeys and the like), rodents such as mouse and rat, and non-rodents such as cattle, pig, and goat are included in the animals.

The vector of the present invention is such that when a microRNA target sequence is added to the NP gene or P gene, the amount of gene expression from the vector or the amount of the vector is significantly low compared to the case in which a microRNA target sequence is not added, and specifically, the amount is decreased to, for example, 70% or lower, preferably 60% or lower, 50% or lower, 40% or lower, 30% or lower, or $1/5$ or lower, preferably $1/8$ or lower, preferably $1/10$ or lower, $1/20$ or lower, $1/30$ or lower, or $1/50$ or lower. Furthermore, the vector of the present invention is such that when a microRNA target sequence is added to the NP gene or P gene, the expression amount of a reporter protein from the vector is significantly low compared to the expression amount of the reporter protein in the case in which a microRNA target sequence is not added, and specifically, for example, the expression amount is $2/3$ or less, preferably $1/2$ or less, preferably $1/3$ or less, $1/5$ or less, $1/8$ or less, preferably $1/10$ or less, $1/20$ or less, $1/30$ or less, or $1/50$ or less. Regarding the cells, any desired cells capable of expressing the microRNA are used. There are no particular limitations on the timing for measuring the gene expression from the vector as long as the microRNA is expressed in a cell; however, for example, measurement may be made at any time after 24 hours, after 48 hours, after 3 days, after 5 days, after one week, after two weeks, or after three weeks, from the introduction of the virus vector.

The vector of the present invention is such that when a microRNA target sequence is added to the L gene, the amount of gene expression from the vector or the amount of vector obtainable after the vector is introduced into cells is significantly high compared to the case in which a microRNA target sequence is not added, and specifically, the amount is, for example, 1.2 times or higher, preferably 1.3 times or higher, preferably 1.4 times or higher, 1.5 times or higher, 1.6 times or higher, preferably 1.7 times or higher, 1.8 times or higher, 1.9 times or higher, 2 times or higher, 3 times or higher, 4 times or higher, 5 times or higher, or 6 times or higher. Regarding the cells, any desired cells capable of expressing the microRNA are used. Furthermore, there are no particular limitations on the timing for measuring the gene expression from the vector as long as the microRNA is expressed in a cell; however, for example, measurement may be made at any time after 24 hours, after 48 hours, after 3 days, after 5 days, after one week, or after two weeks, from the introduction of the virus vector.

The present invention relates to a method for promoting the removal of a minus-strand RNA virus vector, the method including co-infecting the minus-strand RNA virus vector having a microRNA target sequence added to the NP gene or P gene, together with the minus-strand RNA virus vector for which removal is intended. This minus-strand RNA virus vector to be removed is not particularly limited as long as the virus vector is a minus-strand RNA virus vector of the same kind as the minus-strand RNA virus vector of the present invention, and may be a wild type minus-strand RNA virus vector or a genetically deficient or genetically modified minus-strand RNA virus vector. According to the present invention, the minus-strand RNA virus of the present invention can be expected to promote the removal of the vector itself from the infected cells, and to also promote the removal of any other co-existing minus-strand RNA virus vectors. That is, the vector of the present invention is not only useful for promoting the removal of the vector of the present invention itself and the removal of genes carried by that vector, but also useful for promoting the removal of any other co-existing minus-strand RNA virus or minus-strand RNA virus vector and genes carried by that vector.

That is, the present invention provides a method for promoting the removal of a minus-strand RNA virus or a minus-strand RNA virus vector, the method including a step of co-infecting the minus-strand RNA virus vector of the present invention having a microRNA target sequence added to the NP gene or P gene, together with the minus-strand RNA virus or the minus-strand RNA virus vector, for which removal is intended. Co-infection may be achieved as long as there is a time period for which the vectors co-exist in cells, and it is not necessary to simultaneously achieve infection. Initially, cells may be infected with the minus-strand RNA virus or the minus-strand RNA virus vector to be removed, and when there is a need to remove the virus or vector, the cells may be infected with the vector of the present invention.

The present invention also provides a removal promoting agent for a minus-strand RNA virus or a minus-strand RNA virus vector, the agent including the minus-strand RNA virus vector of the present invention having a microRNA target sequence added to the NP gene or P gene. The present invention also provides a removal promoter for a gene to be introduced into a minus-strand RNA virus vector, the agent including the minus-strand RNA virus vector of the present invention. The present invention also provides use of the minus-strand RNA virus vector of the present invention, for the promotion of removal of a minus-strand RNA virus vector and/or a gene to be introduced by a minus-strand RNA virus vector. The present invention also provides use of the minus-strand RNA virus vector of the present invention, for the production of a removal-promoting agent for a minus-strand RNA virus vector and/or a gene to be introduced by a minus-strand RNA virus vector. The expression of genes carried by the vector of the present invention can be controlled by using the vector of the present invention, and in addition to that, expression of genes carried by other minus-strand RNA virus vectors can also be controlled.

EXAMPLES

Hereinafter, the present invention will be described in more detail by way of Examples; however, the present invention is not intended to be limited to these Examples. Furthermore, those documents and other references cited in the present specification are all incorporated herein as part of the present specification.

<Production of Sendai Virus Vector Used in Present Invention for Carrying Exogenous Gene>

A method for producing a Sendai virus vector carrying exogenous genes as used in the present invention will be described below. According to the present invention, the term "18+" means that GOI is inserted before the NP gene; the term "(PM)" means that GOI is inserted between the P gene and the M gene; the term "(F)" means that GOI is inserted in place of the F gene (between the M gene and the HN gene); and the term "(HNL)" means that GOID is inserted between the HN gene and the L gene. In the present invention, for the Sendai virus, Z strain virus was used in all cases. Furthermore, the term "TS" according to the present invention means that there are mutations of G69E, T116A, and A183S in the M protein; mutations of A262T, G264R, and K461G in the HN protein; a mutation of L511F in the P protein; and mutations of N1197S and K1795E in the L protein. The term "ΔF" means that the F gene has been deleted. For example, an F gene-deleted type Sendai virus vector in which GOI has been inserted before the NP gene is described as SeV18+/ΔF, and the same vector having the TS mutation is described as SeV18+/TSΔF. Similarly, in regard to a vector in which GOI has been inserted before the NP gene, the M gene has been deleted, and the proteolytic orientation of the F protein has been modified, a vector in which the proteolytic orientation has been modified into MMP type is described as SeV18+/Fct14 (MMP)-HN/ΔM, and a vector in which the proteolytic orientation has been modified into uPA type is described as SeV18+/Fct14 (uPA)-HN/ΔM. Unless particularly stated otherwise, the restriction enzyme used for the insertion of GOI is NotI. Furthermore, TS12 is a Sendai virus vector-containing mutations of D433A, R434A, and K437A in the P protein in addition to the TS mutation described above, and TS15 is a Sendai virus vector-containing mutations of L1361C and L1558I in the L protein in addition to the TS12 mutation described above. However, these are only examples, and the present invention is not intended to be limited to these.

1) Construction of SeV18+DGFP/TSΔF Vector

A PCR reaction was carried out using DasherGFP (DNA2.0, Inc.) as a template and using primers NotI- DGFP-F (5'-ATAGCGGCCGCGACATGACTGCC-CTG-ACCG-3') (SEQ ID NO:8) and DGFP-EIS-NotI-R (5'-TATGCGGCCGCGATGAACTTTCACCCTAAGTTTT-TCTTACTACGGTTACTGATAGGTATCGAGA TCGAC-3') (SEQ ID NO:9). This product was digested with NotI and cloned into pSeV18+TSΔF to obtain pSeV18+DGFP/TSΔF. A Sendai virus produced from the transcription product of the pSeV18+DGFP/TSΔF is referred to as SeV18+DGFP/TSΔF.

2) Construction of SeV18+DGFPmiRT/TSΔF Vector

A PCR reaction was carried out using pSeV18+DGFP/TSΔF as a template and using primers EcoRI-DGFP (5'-ATATGAATTCGCGGCCGCTCGCCACCATGACTG-CCCTGACCG-3') (SEQ ID NO:10) and DGFP-HindIII (5'-ATATAAGCTTCTATTACTGATAGGTATC-3') (SEQ ID NO:11). This product was digested with EcoRI and HindIII, and thus EcoRI-DGFP-HindIII fragment was obtained. Next, miR302-1+(5'-ATATAAGCTTGGTACCT-TATCACCAAAACATGGAAGCACTTACGATTCACCA-AAACATGGAAGC ACTTAGAGCTCATAT-3') (SEQ ID NO:12) and miR302-2+(5'-ATATGAGCTCTAAGTG-CTTCCATGTTTTGGTGAATCGTAAGTGCTTCCATG-TTTTGGTGATAAG GTACCAAGCTTATAT-3') (SEQ ID NO:13) were annealed and digested with HindIII and SacII, and thus HindIII-miR302-SacII fragment was obtained. Next, miR302-3+(5'-ATATGAGCTCTCACCAAAACATG-GAAGCACTTACGATTCACCAAAACATGGAAGCAC-TTAAGTA TGGTACCTCTAGAATAT-3') (SEQ ID NO:14) and miR302-4+(5'-ATATTCTAGAGGTACCATACTTAA-GTGCTTCCATGTTTTGGTGAATCGTAAGTGCTTC-CATGTT TTGGTGAGAGCTCATAT-3') (SEQ ID NO:15) were annealed and digested with SacII and XbaI, and thus SacII-miR302-XbaI fragment was obtained. Next, XbaI-EIS-NotI-BamHI-F (5'-ATATTCTAGAGTAAGAAAAA-CTTAGGGTGAAAGTTCGCGGCCGCGGATCCATAT-3') (SEQ ID NO:16) and XbaI-EIS-NotI-BamHI-R (5'-ATATG-GATCCGCGGCCGCGAACTTTCACCCTAAGTTTTTC-TTACTCTAGAATAT-3') (SEQ ID NO:17) were annealed and digested with XbaI and BamHI, and thus XbaI-EIS-BamHI fragment was obtained. Next, these were digested with BamHI and EcoRI and cloned into pBlueScript II-SK+ (Stratagene Corporation), and thus pBS-DGFP-miR302T4 was obtained. Next, pBS-DGFP-miR302T4 was digested with NotI and cloned into pSeV18+TSΔF, and thus pSeV18+DGFPmiRT/TSΔF was obtained. A Sendai virus produced from the transcription product of the pSeV18+DGFPmiRT/TSΔF vector is referred to as SeV18+DGFPmiRT/TSΔF.

3) Construction of SeV18+DGFP/PmiRT-TSΔF Vector

First, construction of pSeV18+/PLmutTSΔF was carried out as follows. A PCR reaction was carried out using pSeV18+/TSΔF as a template and using primers BamHI-P-F (5'-ATATGGATCCAGTTCACGCGGCCGCA-3') (SEQ ID NO:41) and XhoI-P-R (5'-ATATCTCGAGTCGG-TGCAGGCCTTTA-3') (SEQ ID NO:42). This PCR product was digested with BamHI and XhoI, and a DNA fragment thus obtained was cloned into pBlueScript II-SK+(Stratagene Corporation) to obtain pBS-P. A PCR reaction was carried out using this pBS-P as a template and using primers Pmut-F1 (5'-GGATCATACGGCGCGCCAAGGTACTTG-3') (SEQ ID NO:43), Pmut-R1 (5'-CAAGTACCTTGG-CGCGCCGTATGATCC-3') (SEQ ID NO:44), Pmut-F2 (5'-CAACTAGATCCTGCAGGAGGCATCCTAC-3') (SEQ ID NO:45), and Pmut-R2 (5'-GTAGGATGCCTCCTGCAG-GATCTAGTTG-3') (SEQ ID NO:46). An AscI site was introduced at a position upstream of the P gene, and an SbfI site was introduced into a position downstream of the P gene. Thus, pBS-Pmut was obtained. Next, a PCR reaction was carried out using pSeV18+TSΔF as a template and using primers BamHI-L-F (5'-ATATGGATCCGTAC-GATCGCAGTCCACCAT-3') (SEQ ID NO:47) and XhoI-L-R (5'-ATATCTCGAGCAGCTAGCTCAACTGA-3') (SEQ ID NO:48). This PCR product was digested with BamHI and XhoI, a DNA fragment thus obtained was cloned into pBlueScript II-SK+, and thus pBS-L was obtained. A PCR reaction was carried out using this pBS-L as a template and using primers Lmut-F (5'-GTGAATGGGAGGCCGGC-CATAGGTC-3') (SEQ ID NO:49) and Lmut-R (5'-GACC-TATGGCCGGCCTCCCATTCAC-3') (SEQ ID NO:50). An FseI site was introduced into a position upstream of the L gene, and thus pBS-Lmut was obtained. Next, pSeV18+/TSΔF was digested with SalI and PvuI, pBS-Lmut was digested with PvuI and KpnI, and the digestion product was cloned into pBlueScript II-SK+. Thus, pBS-LmutSeV was obtained. Next, pBS-LmutSeV was digested with NheI and SalI and cloned into pSeV18+/TSΔF, and thus pSeV18+/LmutTSΔF was obtained. Next, pSeV18+/LmutTSΔF was digested with NotI, NheI, and StuI, and pBS-Pmut was digested with NotI and StuI. These DNA fragments were joined to obtain pSeV18+/PLmutTSΔF.

A PCR reaction was carried out using pSeV18+/PLmutTSΔF as a template and using primers SeVF1603 (5'-CTGCAACCCATGGAGATGAAGG-3') (SEQ ID NO:18) and P-miR302T4-C (5'-CCAAGCTTCTAT-TATCTAGTTGGTCAGTG-3') (SEQ ID NO:19), and thus SeVF1603-P-miRT fragment was obtained. Next, a PCR reaction was carried out using pSeV18+DGFPmiRT/TSΔF as a template and using primers P-miR302T4-N (5'-CACTGACCAACTAGATAATAGAAGCTTGG-3') (SEQ ID NO:20) and P-miR302T4-SbfI-C (5'-TATACCT-GCAGGCTCTAGAGGTACCATAC-3') (SEQ ID NO:21), and P-miRT-SbfI fragment was obtained. Next, a PCR reaction was carried out using the SeVF1603-P-miRT fragment and the P-miRT-SbfI fragment as templates and primers SeVF1603 (SEQ ID NO:18) and P-miR302T4-SbfI-C (SEQ ID NO:21). This product was digested with AscI and SbfI and cloned into pSeV18+/PLmutTSΔF, and thus pSeV18+/PmiRT-TSΔF was obtained. Next, pSeV18+DGFP/TSΔF was digested with NotI, and DGFP-NotI fragment thus obtained was cloned into pSeV18+/PmiRT-TSΔF. Thus, pSeV18+DGFP/PmiRT-TSΔF was obtained. A Sendai virus produced from the transcription product of the pSeV18+DGFP/PmiRT-TSΔF vector is referred to as SeV18+DGFP/PmiRT-TSΔF.

4) Construction of SeV18+DGFP/LmiRT #2-TSΔF Vector pBS-DGFP-miR302T4 was digested with KpnI and cloned into pSeV18+DGFP/TSΔF, and thus pSeV18+DGFP/LmiRT #2-TSΔF was obtained. A Sendai virus produced from the transcription product of the pSeV18+DGFP/LmiRT #2-TSΔF vector is referred to as SeV18+DGFP/LmiRT #2-TSΔF.

5) Construction of SeV18+DGFP/LmiRT #1-TSΔF Vector

A PCR reaction was carried out using pSeV18+DGFPmiRT/TSΔF as a template and using primers SeVF13201 (5'-TCGTGGAACCTGTGTATGGGCC-3') (SEQ ID NO:22) and L-miR302T4-C (5'-GGTAC-CAAGCTTCTATTATTACGAGCTGTC-3') (SEQ ID NO:23), and SeVF13201-LmiRT fragment was obtained.

Next, a PCR reaction was carried out using pSeV18+DGFPmiRT/TSΔF as a template and using primers L-miR302T4-N (5'-GACAGCTCGTAATAATAGAAGC-TTGGTACC-3') (SEQ ID NO:24) and L-miR302T4-SacII-C (5'-ATATCCGCGGAGCTTCGATCGTTCTGC-ACGATAGGGACTAATTCTCTAGAGGTACCATAC-3') (SEQ ID NO:25), and LmiRT-SacII fragment was obtained. Next, a PCR reaction was carried out using the SeVF13201-LmiRT fragment and the LmiRT-SacII fragment as templates and using primers SeVF13201 (SEQ ID NO:22) and L-miR302T4-SacII-C (SEQ ID NO:25). This product was digested with XhoI and SacII and cloned into pSeV18+DGFP/TSΔF, and thus pSeV18+DGFP/LmiRT #1-TSΔF was obtained. A Sendai virus produced from the transcription product of the pSeV18+DGFP/LmiRT #1-TSΔF vector is referred to as SeV18+DGFP/LmiRT #1-TSΔF.

6) Construction of SeV18+DGFP/NPmiRT-TSΔF Vector

A PCR reaction was carried out using pSeV18+/PLmutTSΔF as a template and primers SeVF426 (5'-ATC-TACAACATAGAGAAAGACC-3') (SEQ ID NO:26) and NP-miR302T4-C (5'-AGCTTCTATTATCTAGATTCC-TCCTATCCC-3') (SEQ ID NO:27), and SeVF426-NPmiRT fragment was obtained. Next, a PCR reaction was carried out using pSeV18+DGFP/PmiRT-TSΔF as a template and using primers NP-miR302T4-N (5'-GGAGGAATCTAGA-TAATAGAAGCTTGGTAC-3') (SEQ ID NO:28) and miR302T4-AscI-C (5'-ATATGCGCGCCGTATGATCATA-TCTCTAGAGGTACC-3') (SEQ ID NO:29), and NPmiRT-AscI fragment was obtained. Next, a PCR reaction was carried out using the SeVF426-NPmiRT fragment and the NPmiRT-AscI fragment as templates and using primers SeVF426 (SEQ ID NO:26) and miR302T4-AscI-C (SEQ ID NO:29). This product was digested with SphI and AscI and cloned into pSeV18+/PLmutTSΔF, and thus pSeV18+/NPmiRT-TSΔF was obtained. DGFP-NotI fragment was cloned into pSeV18+/NPmiRT-TSΔF, and thus pSeV18+DGFP/NPmiRT-TSΔF was obtained. A Sendai virus produced from the transcription product of the pSeV18+DGFP/NPmiRT-TSΔF vector is referred to as SeV18+DGFP/NPmiRT-TSΔF.

7) Construction of SeV18+DGFP/PmiRTtag-TSΔF Vector

A PCR reaction was carried out using pSeV18+DGFP/TSΔF as a template and using primers SeVF1603 (SEQ ID NO:18) and P-miR302T4tag-C (5'-GCTTCTAT-TAATGTTGGTCAGTGACTCTAT-3') (SEQ ID NO:30), and SeVF1603-P-miR302T4tag fragment was obtained. Next, a PCR reaction was carried out using pSeV18+DGFP/TSΔF as a template and using primers P-miR302T4tag-N (5'-GACCAACATTAATAGAAGCTTGGTACCTTA-3') (SEQ ID NO:31) and P-miR302T4tag-SbfI-C (5'-ATATCCTGCAGGTATTACTACTCTAGAGGTAC-CATAC-3') (SEQ ID NO:32), and thus P-miR302T4tag-SbfI fragment was obtained. Next, a PCR reaction was carried out using the SeVF1603-P-miR302T4tag fragment and the P-miR302T4tag-SbfI fragment as templates and using primers SeVF1603 (SEQ ID NO:18) and P-miR302T4tag-SbfI-C (SEQ ID NO:32). This product was digested with AscI and SbfI and cloned into pSeV18+DGFP/PmiRT-TSΔF, and thus pSeV18+DGFP/PmiRTtag-TSΔF was obtained. A Sendai virus produced from the transcription product of the pSeV18+DGFP/PmiRTtag-TSΔF vector is referred to as SeV18+DGFP/PmiRTtag-TSΔF.

8) Construction of SeV18+DGFP/PmiRTx1-TSΔF Vector

A PCR reaction was carried out using pSeV18+/PLmutTSΔF as a template and using primers SeVF1603 (SEQ ID NO:18) and P-miR302T1-C1 (5'-GTACCATACT-TAAGTGCTTCCATGTTTTGGTGATAAGGTACCAAG-CTTCTATTATCTAGTTGGT CAGTGAC-3') (SEQ ID NO:33), and SeVF1603-PmiR302T1 fragment was obtained. Next, a PCR reaction was carried out using the SeVF1603-PmiR302T1 fragment as a template and using primers SeVF1603 (SEQ ID NO:18) and P-miR302T1-C2-SbfI (5'-ATATCCTGCAGGTATCTCTAGAGGTACCAT-ACTTAAG-3') (SEQ ID NO:34). This product was digested with AscI and SbfI and cloned into pSeV18+DGFP/PmiRT-TSΔF, and thus pSeV18+DGFP/PmiRTx1-TSΔF was obtained. A Sendai virus produced from the transcription product of the pSeV18+DGFP/PmiRTx1-TSΔF vector is referred to as SeV18+DGFP/PmiRTx1-TSΔF.

9) Construction of SeV18+DGFP/PmiRTx2-TSΔF Vector

A PCR reaction was carried out using pSeV18+/PLmutTSΔF as a template and primers SeVF1603 (SEQ ID NO:18) and P-miR302T2-C1 (5'-CATGTTTTGGTGAAT-CGTAAGTGCTTCCATGTTTTGGTGATAAGGTACCA-AGCTTCTATTATCT AGTTGGTCAGTGACTC-3') (SEQ ID NO:35), and SeVF1603-PmiR302T2 fragment was obtained. Next, a PCR reaction was carried out using the SeVF1603-PmiR302T2 fragment as a template and using primers SeVF1603 (SEQ ID NO:18) and P-miR302T2-C2-SbfI (5'-ATATCCTGCAGGATCTCTAGAGGTACCATAC-TTAAGTGCTTCCATGTTTTGGTGAATCGTAAGT GC-TTCCATGTTTTGGT-3') (SEQ ID NO:36). This product was digested with AscI and SbfI and cloned into pSeV18+DGFP/PmiRT-TSΔF, and thus pSeV18+DGFP/PmiRTx2-TSΔF was obtained. A Sendai virus produced from the transcription product of the pSeV18+DGFP/PmiRTx2-TSΔF vector is referred to as SeV18+DGFP/PmiRTx2-TSΔF.

10) Construction of SeV18+DGFP/PmiR367T2-TSΔF Vector

A PCR reaction was carried out using pSeV18+/PLmutTSΔF as a template and using primers SeVF1603 (SEQ ID NO:18) and P-miR367T2-C1 (5'-CTTTAG-CAATGGTGATAATCCACCAAGCTTCTATTATCTAG-TTGGTCAGTGACTC-3') (SEQ ID NO:37), and SeVF-1603-PmiR367T2 fragment was obtained. Next, a PCR reaction was carried out using the SeVF1603-PmiR367T2 fragment as a template and using primers SeVF1603 (SEQ ID NO:18) and P-miR367T2-C2-SbfI (5'-ATATCCTGC-AGGCTCTCGACTGAATTGCACTTTAGCAATGGTGA-ATCGAATTGCACTTTAGCAA TGGTGATAATCCACC-3') (SEQ ID NO:38). This product was digested with AscI and SbfI and cloned into pSeV18+DGFP/PmiRT-TSΔF, and thus pSeV18+DGFP/PmiR367T2-TSΔF was obtained. A Sendai virus produced from the transcription product of the pSeV18+DGFP/PmiR367T2-TSΔF vector is referred to as SeV18+DGFP/PmiR367T2-TSΔF.

11) Construction of SeV18+DGFP/PmiR126T2-TSΔF Vector

A PCR reaction was carried out using pSeV18+/PLmutTSΔF as a template and using primers SeVF1603 (SEQ ID NO:18) and P-miR126T2-C1 (5'-GAGTAA-TAATGCGTAATCCACCAAGCTTCTATTATCTAGTT-GGTCAGTGACTC-3') (SEQ ID NO:39), and SeVF1603-PmiR126T2 fragment was obtained. Next, a PCR reaction was carried out using the SeVF1603-PmiR126T2 fragment and using primers SeVF1603 (SEQ ID NO:18) and P-miR126T2-C2-SbfI (5'-ATATCCTGCAGGCTCTCG-ACT- GTCGTACCGTGAGTAATAATGCGATCGTCGT-ACCGTGAGTAAT AATGCGTAATCCACC-3') (SEQ ID NO:40). This product was digested with AscI and SbfI and cloned into pSeV18+DGFP/PmiRT-TSΔF, and thus pSeV18+DGFP/PmiR126T2-TSΔF was obtained. A Sendai virus produced from the transcription product of the pSeV18+DGFP/PmiR126T2-TSΔF vector is referred to as SeV18+DGFP/PmiR126T2-TSΔF.

12) Construction of SeV18+DGFP/PmiRTΔF Vector

A PCR reaction was carried out using pSeV18+ΔF as a template and using primers BamHI-P-F (SEQ ID NO:41) and Pmut-R1 (SEQ ID NO:44), and BamHI-PmutdF fragment was obtained. Next, a PCR reaction was carried out using pSeV18+ΔF as a template and using primers Pmut-F1 (SEQ ID NO:43) and Pmut-R2 (SEQ ID NO:46), and PmutdF fragment was obtained. Next, a PCR reaction was carried out using pSeV18+ΔF as a template and using primers Pmut-F2 (SEQ ID NO:45) and XhoI-P-R (SEQ ID NO:42), and PmutdF-XhoI fragment was obtained. Next, a PCR reaction was carried out using the BamHI-PmutdF fragment, PmutdF fragment and PmutdF-XhoI fragment as templates and using primers BamHI-P-F (SEQ ID NO:41) and XhoI-P-R (SEQ ID NO:42). A DNA fragment thus obtained was cloned into pBlueScript II-SK+, and pBS-PmutdF was obtained. Next, pBS-PmutdF was digested with NotI, StuI, and XhoI, and thus a 3878 bp fragment was obtained. Next, pSeV18+ΔF was digested with NotI and NheI, and a 6321 bp fragment was obtained. Next, pSeV18+ΔF was digested with NotI, StuI, and NheI, and a 6161 bp fragment was obtained. Next, the 3878 bp fragment, the 6321 bp fragment, and the 6161 bp fragment were joined, and thus pSeV18+/PmutΔF was obtained. Next, a PCR reaction was carried out using pSeV18+/PmutΔF as a template and using primers SeVF1603 (SEQ ID NO:18) and P-miR302T4-C (SEQ ID NO:19), and SeVF1603-PdF-miRT fragment was obtained. Next, a PCR reaction was carried out using the SeVF1603-PdF-miRT fragment and the P-miRT-SbfI fragment and using primers SeVF1603 (SEQ ID NO:18) and P-miR302T4-SbfI-C (SEQ ID NO:21). This product was digested with AscI and SbfI and cloned into pSeV18+/PmutΔF, and thus pSeV18+/PmiRTΔF was obtained. Next, the DGFP-NotI fragment was cloned into pSeV18+/PmiRTΔF, and thus pSeV18+DGFP/PmiRTΔF was obtained. A Sendai virus produced from the transcription product of the pSeV18+DGFP/PmiRTΔF vector is referred to as SeV18+DGFP/PmiRTΔF.

13) Construction of SeV18+DGFP/PmiR372T2-TSΔF Vector

A PCR reaction was carried out using pSeV18+/PLmutTSΔF as a template and using primers SeVF1603 (SEQ ID NO:18) and P-miR372T2-C1 (5'-CGACATTT-GAGCGTAATCCACCAAGCTTCTATTATCTAGTT-GGTCAGTGACTC-3') (SEQ ID NO:70), and SeVF1603-PmiR372T2 fragment was obtained. Next, a PCR reaction was carried out using the SeVF1603-PmiR124T2 fragment as a template and using primers SeVF1603 (SEQ ID NO:18) and P-miR372T2-C2-SbfI (5'-ATATCCTGCAGGCTC-TCGACTGAAAGTGCTGCGACATTTGAGCGTACG-AAAGTGCTGCGACATT TGAGCGTAATCCACC-3') (SEQ ID NO:71). This product was digested with AscI and SbfI and cloned into pSeV18+DGFP/PmiRT-TSΔF, and thus pSeV18+DGFP/PmiR372T2-TSΔF was obtained. A Sendai virus produced from the transcription product of the pSeV18+DGFP/PmiR372T2-TSΔF vector is referred to as SeV18+DGFP/PmiR372T2-TSΔF.

14) Construction of SeV18+DGFP/PmiR143T2-TSΔF Vector

A PCR reaction was carried out using pSeV18+/PLmutTSΔF as a template and using primers SeVF1603 (SEQ ID NO:18) and P-miR143T2-C1 (5'-GCACTGT-AGCTCATAATCCACCAAGCTTCTATTATCTAGTTG-GTCAGTGACTC-3') (SEQ ID NO:72), and SeVF1603-PmiR143T2 fragment was obtained. Next, a PCR reaction was carried out using the SeVF1603-PmiR143T2 fragment as a template and using primers SeVF1603 (SEQ ID NO:18) and P-miR143T2-C2-SbfI (5'-ATATCCTGCAGGCTCTC-GACTGTGAGATGAAGCACTGTAGCTCAATCGTGA-GATGAAGCACTGT AGCTCATAATCCACC-3') (SEQ ID NO:73). This product was digested with AscI and SbfI and cloned into pSeV18+DGFP/PmiRT-TSΔF, and thus pSeV18+DGFP/PmiR143T2-TSΔF was obtained. A Sendai virus produced from the transcription product of the pSeV18+DGFP/PmiR143T2-TSΔF vector is referred to as SeV18+DGFP/PmiR143T2-TSΔF.

15) Construction of SeV18+DGFP/PmiR122T2-TSΔF Vector

A PCR reaction was carried out using pSeV18+/PLmutTSΔF as a template and using primers SeVF1603 (SEQ ID NO:18) and P-miR122T2-C1 (5'-CAATGG-TGTTTGTAATCCACCAAGCTTCTATTATCTAGTTGG-TCAGTGACTC-3') (SEQ ID NO:74), and SeVF1603-PmiR122T2 fragment was obtained. Next, a PCR reaction was carried out using the SeVF1603-PmiR122T2 fragment as a template and using primers SeVF1603 (SEQ ID NO:18) and P-miR122T2-C2-SbfI (5'-ATATCCTGCAGG- CTCTC-GACTGTGGAGTGTGACAATGGTGTTTGATCGTGGA-GTGTGACAATGG TGTTTGTAATCCACC-3') (SEQ ID NO:75). This product was digested with AscI and SbfI and cloned into pSeV18+DGFP/PmiRT-TSΔF, and thus pSeV18+DGFP/PmiR122T2-TSΔF was obtained. A Sendai virus produced from the transcription product of the pSeV18+DGFP/PmiR122T2-TSΔF vector is referred to as SeV18+DGFP/PmiR122T2-TSΔF.

16) Construction of SeV18+DGFP/PmiR218T2-TSΔF Vector

A PCR reaction was carried out using pSeV18+/PLmutTSΔF as a template and using primers SeVF1603 (SEQ ID NO:18) and P-miR218T2-C1 (5'-GATCTAAC-CATGTGTAATCCACCAAGCTTCTATTATCTAGTT-GGTCAGTGACTC-3') (SEQ ID NO:76), and SeVF1603-PmiR218T2 fragment was obtained. Next, a PCR reaction was carried out using the SeVF1603-PmiR218T2 fragment and using primers SeVF1603 (SEQ ID NO:18) and P-miR218T2-C2-SbfI (5'-ATATCCTGCAGGCTCT- CGA-CTGTTGTGCTTGATCTAACCATGTGATCGTTGT-GCTTGATCTAAC CATGTGTAATCCACC-3') (SEQ ID NO:77). This product was digested with AscI and SbfI and cloned into pSeV18+DGFP/PmiRT-TSΔF, and thus pSeV18+DGFP/PmiR218T2-TSΔF was obtained. A Sendai virus produced from the transcription product of the pSeV18+DGFP/PmiR218T2-TSΔF vector is referred to as SeV18+DGFP/PmiR218T2-TSΔF.

17) Construction of SeV18+DGFP/PmiR124T2-TSΔF Vector

A PCR reaction was carried out using pSeV18+/PLmutTSΔF as a template and using primers SeVF1603 (SEQ ID NO:18) and P-miR124T2-C1 (5'-CGGTGAATGC-CAATAATCCACCAAGCTTCTATTATCTAGTTGG-TCAGTGACTC-3') (SEQ ID NO:78), and thus SeVF1603-PmiR124T2 fragment was obtained. Next, a PCR reaction was carried out using the SeVF1603-PmiR124T2 fragment as a template and using primers SeVF1603 (SEQ ID NO:18) and P-miR124T2-C2-SbfI (5'-ATATCCTGCAGGC-TCTCGACTGTAAGGCACGCGGTGAATGCCAAA-TCGTAAGGCACGCGGTGAA TGCCAATAATCC-3') (SEQ ID NO:79). This product was digested with AscI and SbfI and cloned into pSeV18+DGFP/PmiRT-TSΔF, and thus pSeV18+DGFP/PmiR124T2-TSΔF was obtained. A Sendai virus produced from the transcription product of the pSeV18+DGFP/PmiR124T2-TSΔF vector is referred to as SeV18+DGFP/PmiR124T2-TSΔF.

18) Construction of SeV18+DGFP/PmiR138T2-TSΔF Vector

A PCR reaction was carried out using pSeV18+/PLmutTSΔF as a template and using primers SeVF1603 (SEQ ID NO:18) and P-miR138T2-C1 (5'-GTGAATCAGGCCGTAATCCACCAAGCTTCTATTATCTAGTTGGTCAGTGACTC-3') (SEQ ID NO:80), and SeVF1603-PmiR138T2 fragment was obtained. Next, a PCR reaction was carried out using the SeVF1603-PmiR138T2 fragment as a template and using primers SeVF1603 (SEQ ID NO:18) and P-miR138T2-C2-SbfI (5'-ATATCCTGCAGGCTCTCGACTAGCTGGTGTTGTGAATCAGGCCGATCAGCTGGTGTTGTGAATC AGGCCGTAATCCACC-3') (SEQ ID NO:81). This product was digested with AscI and SbfI and cloned into pSeV18+DGFP/PmiRT-TSΔF, and thus pSeV18+DGFP/PmiR138T2-TSΔF was obtained. A Sendai virus produced from the transcription product of the pSeV18+DGFP/PmiR138T2-TSΔF vector is referred to as SeV18+DGFP/PmiR138T2-TSΔF.

19) Construction of SeV18+DGFP/PmiR367T1-TSΔF Vector

A PCR reaction was carried out using pSeV18+DGFP/PmiR367T2-TSΔF as a template and using primers SeVF1603 (SEQ ID NO:18) and miR367T1-C-SbfI (5'-ATATCCTGCAGGCTATCGAATTGCACTTTAGCAATGGTGATAATCCACCAAGCTTCTATTATCT AGTTGGTCAGTGACTC-3') (SEQ ID NO:82). This product was digested with AscI and SbfI and cloned into pSeV18+DGFP/PmiRT-TSΔF, and thus pSeV18+DGFP/PmiR367T1-TSΔF was obtained. A Sendai virus produced from the transcription product of the pSeV18+DGFP/PmiR367T1-TSΔF vector is referred to as SeV18+DGFP/PmiR367T1-TSΔF.

20) Construction of SeV18+DGFP/miR367T1-NP-TSΔF Vector

First, construction of pSeV18+/PLmutTSΔFver2 was carried out as follows. A PCR reaction was carried out using pSeV18+/PLmutTSΔF as a template and using primers SeVF3208 (5'-AGAGAACAAGACTAAGGCTACCAGGTTTGACC-3') (SEQ ID NO:83) and AsiSI-C (5'-AGGCGATCGCTCTTTCACCCTAAGTTTTTC-3') (SEQ ID NO:84), and thus SeVF3208-AsiSI-C fragment was obtained. Next, a PCR reaction was carried out using pSeV18+/PLmutTSΔF as a template and using primers AsiSI-N (5'-GAAAGAGCGATCGCCTAACACGGCGCAATG-3') (SEQ ID NO:85) and SeVR4246 (5'-TTTGGGATCTTGGCTATGGTGAT-3') (SEQ ID NO:86), and AsiSI-N-SeVR4246 fragment was obtained. Next, a PCR reaction was carried out using the SeVF3208-AsiSI-C fragment and the AsiSI-N-SeVR4246 fragment as templates and using primers SeVF3208 and SeVR4246. The product was cloned into pGEM-T Easy (Promega Corporation), and thus pGEM/P-SbfI-AsiSI was obtained. Next, pGEM/P-SbfI-AsiSI was digested with StuI and SbfI, pSeV18+/PLmutTSΔF was digested with NheI and SbfI, and pSeV18+/PLmutTSΔF was digested with StuI and NheI. The three fragments were annealed, and thus pSeV18+/PLmutTSΔFver2 was obtained. The DGFP-NotI fragment was cloned into pSeV18+/PLmutTSΔFver2, and thus pSeV18+DGFP/PLmutTSΔFver2 was obtained.

A PCR reaction was carried out using pSeV18+/PLmutTSΔF as a template and using primers NotI-miR367T1-NP-N (5'-ATATGCGGCCGCATCACCATTGCTAAAGTGCAATTCAGATCTTCACGATGGCCGG GTTGTTGAG C-3') (SEQ ID NO:87) and SeVR744 (5'-CGTCTTGTCTGAACGCCTCTAAC-3') (SEQ ID NO:88). This product was cloned into pSeV18+DGFP/PLmutTSΔFver2, and thus pSeV18+DGFP/miR367T1-NP-TSΔF was obtained. A Sendai virus produced from the transcription product of the pSeV18+DGFP/miR367T1-NP-TSΔF vector is referred to as SeV18+DGFP/miR367T1-NP-TSΔF.

21) Construction of SeV18+DGFP/miR367T1-P-TSΔF Vector

First, construction of pSeV18+/PLmutTSΔFver3 was carried out as follows. A PCR reaction was carried out using pSeV18+/PLmutTSΔF as a template and using primers SeVF1603 (SEQ ID NO:18) and AscI-AsiSI-SalI-C (5'-GCCTTGCGATCGCCGATCGGTGGATGAACT-3') (SEQ ID NO:89), and thus SeVF1603-AscI-AsiSI-SalI-C fragment was obtained. Next, a PCR reaction was carried out using pSeV18+/PLmutTSΔF as a template and using primers AscI-AsiSI-SalI-N (5'-CCGATCGGCGATCGCAAGGCCACACCCAAC-3') (SEQ ID NO:90) and SeVR2231 (5'-CAGAGTTTGTACCAGTTCTTCCCC-3') (SEQ ID NO:91), and thus AscI-AsiSI-SalI-N-SeVR2231 fragment was obtained. Next, a PCR reaction was carried out using the SeVF1603-AscI-AsiSI-SalI-C fragment and the AscI-AsiSI-SalI-N-SeVR2231 fragment as templates and using primers SeVF1603 and SeVR2231. This product was digested with AscI and SalI and cloned into pSeV18+/PLmutTSΔF, and thus pSeV18+/PLmutTSΔFver3 was obtained.

A PCR reaction was carried out using pSeV18+/PLmutTSΔF as a template and using primers AscI-miR-N (5'-ATATGGCGCGCCAAGGTACTTGATCCGTAG-3') (SEQ ID NO:92) and miR367T1-AsiSI-C (5'-ATATGCGATCGCGAATTGCACTTTAGCAATGGTGATCGATCGGTGGATGAACTTTC-3') (SEQ ID NO:93). This product was digested with AscI and AsiSI and cloned into pSeV18+/PLmutTSΔFver3, and thus pSeV18+/miR367T1-P-TSΔF was obtained. The DGFP-NotI fragment was cloned into pSeV18+/miR367T1-P-TSΔF, and thus pSeV18+DGFP/miR367T1-P-TSΔF was obtained. A Sendai virus produced from the transcription product of the pSeV18+DGFP/miR367T1-P-TSΔF is referred to as SeV18+DGFP/miR367T1-P-TSΔF.

22) Construction of SeV18+DGFP/miR367T1-L-TSΔF Vector

A PCR reaction was carried out using pSeV18+/PLmutTSΔF as a template and using primers FseI-miR367T1-L-N (5'-ATATGGCCGGCCATCACCATTGCTAAAGTGCAATTCATAGGTCATGGATGGGCAGGAGTCC-3') (SEQ ID NO:94) and SeVR12508 (5'-GAATATTTATCGAAGGTTCAGAGGTGTG-3') (SEQ ID NO:95). This product was digested with FseI and NheI and cloned into pSeV18+DGFP/PLmutTSΔFver2, and thus pSeV18+/miR367T1-L-TSΔF was obtained. A Sendai virus produced from the transcription product of the pSeV18+DGFP/miR367T1-L-TSΔF vector is referred to as SeV18+DGFP/miR367T1-L-TSΔF.

23) Construction of SeV18+DGFP/PmiR367T2 m1-TSΔF Vector

A PCR reaction was carried out using pSeV18+DGFP/PmiR367T2-TSΔF as a template and using primers SeVF1603 (SEQ ID NO:18) and miR367T2 m1-C-SbfI (5'-ATATCCTGCAGGCTCTCGACTGAATTGCACTTTATCAATGGTGAATCGAATTGCACTTTATCAA TGGTGATAATCCACCA-3') (SEQ ID NO:96). This product was digested with AscI and SbfI and cloned into pSeV18+DGFP/PmiR367T2-TSΔF, and pSeV18+DGFP/PmiR367T2 ml-TSΔF was obtained. A Sendai virus produced from the transcription product of the pSeV18+DGFP/PmiR367T2 ml-TSΔF vector is referred to as SeV18+DGFP/PmiR367T2 ml-TSΔF.

24) Construction of SeV18+DGFP/PmiR367T2m2-TSΔF Vector

A PCR reaction was carried out using pSeV18+DGFP/PmiR367T2-TSΔF as a template and using primers SeVF1603 (SEQ ID NO:18) and miR367T2m2-C-SbfI (5'-ATATCCTGCAGGCTCTCGACTGAATTGCACTTTAT-TAATGGTGAATCGAATTGCACTTTATTAA TGGTGA-TAATCCACCA-3') (SEQ ID NO:97). This product was digested with AscI and SbfI and cloned into pSeV18+DGFP/PmiR367T2-TSΔF, and thus pSeV18+DGFP/PmiR367T2m2-TSΔF was obtained. A Sendai virus produced from the transcription product of the pSeV18+DGFP/PmiR367T2m2-TSΔF vector is referred to as SeV18+DGFP/PmiR367T2m2-TSΔF.

25) Construction of SeV18+DGFP/PmiR367T2m3-TSΔF

A PCR reaction was carried out using pSeV18+DGFP/PmiR367T2-TSΔF as a template and using primers SeVF1603 (SEQ ID NO:18) and miR367T2m3-C-SbfI (5'-ATATCCTGCAGGCTCTCGACTGAATTGCACTTTCT-TAATGGTGAATCGAATTGCACTTTCTTAA TGGTGA-TAATCCACCA-3') (SEQ ID NO:98). This product was digested with AscI and SbfI and cloned into pSeV18+DGFP/PmiR367T2-TSΔF, and thus pSeV18+DGFP/PmiR367T2m3-TSΔF was obtained. A Sendai virus produced from the transcription product of the pSeV18+DGFP/PmiR367T2m3-TSΔF vector is referred to as SeV18+DGFP/PmiR367T2m3-TSΔF.

26) Construction of SeV18+DGFP/PmiR367T2m4-TSΔF Vector

A PCR reaction was carried out using pSeV18+DGFP/PmiR367T2-TSΔF as a template and using primers SeVF1603 (SEQ ID NO:18) and miR367T2m4-C-SbfI (5'-ATATCCTGCAGGCTCTCGACTGAATTGCACTTACT-TAATGGTGAATCGAATTGCACTTACTTAA TGGTGA-TAATCCACCA-3') (SEQ ID NO:99). This product was digested with AscI and SbfI and cloned into pSeV18+DGFP/PmiR367T2-TSΔF, and thus pSeV18+DGFP/PmiR367T2m4-TSΔF was obtained. A Sendai virus produced from the transcription product of the pSeV18+DGFP/PmiR367T2m4-TSΔF vector is referred to as SeV18+DGFP/PmiR367T2m4-TSΔF.

27) Construction of SeV18+DGFP(HNL)HSV-TK/PmiR302T4-TSΔF Vector

A PCR reaction was carried out using pSELECT-zeo-HSV1tk (InvivoGen, Inc.) as a template and using primers NotI-HSVtk-N (5'-ATATGCGGCCGCGACGTCACCAT-GGCTTCTTACCCTGGAC-3') (SEQ ID NO:100) and HSVtk-EIS-NotI-C (5'-ATATGCGGCCGCGATGAACT-TTCACCCTAAGTTTTTCTTACTACGGTTAGTTGG-CCTCTCCCAT CTCCC-3') (SEQ ID NO:101), and thus HSVtk-NotI fragment was obtained. Next, pSeV18+/PmiRT-TSΔF was digested with AscI and SbfI, and the PmiR302T4 fragment thus obtained was cloned into pSeV(HNL)AG/d2PTS15ΔF (WO 2016/125364). Thus, pSeV(HNL)AG/PmiR302T4-TS15ΔF was obtained. Next, pSeV18+/PLmutTSΔF was digested with NheI and SacI, the L gene (TS) thus obtained was cloned into pSeV(HNL)AG/PmiR302T4-TS15Δ, and thus pSeV(HNL)AG/PmiR302T4-TSΔF was obtained. Next, the HSVtk-NotI fragment was digested with NotI and cloned into pSeV(HNL)AG/PmiR302T4-TSΔF, and thus pSeV(HNL)HSVtk/PmiR302T4-TSΔF was obtained. Next, pSeV18+DGFP/PmiRT-TSΔF and pSeV(HNL)HSVtk/PmiR302T4-TSΔF were digested with AscI and SacII, and these fragments were joined to obtain pSeV18+DGFP(HNL)HSV-TK/PmiR302T4-TSΔF. A Sendai virus produced from the transcription product of the pSeV18+DGFP(HNL)HSV-TK/PmiR302T4-TSΔF vector is referred to as SeV18+DGFP(HNL)HSV-TK/PmiR302T4-TSΔF.

28) Construction of SeV(PF)DGFP/TSΔM-Fct14 (uPA #2) Vector

A PCR reaction was carried out using pSeV18+(WO 97/16539) as a template and using primers AsiSI-F-N (5'-ATATGCGATCGCAAACATGACAG-CATATATCCAGAGATCACAG-3') (SEQ ID NO:102) and F-SwaI-C (5'-CAATTTAAATTCATCTTTTCTCAGC-CATTG-3') (SEQ ID NO:103), and AsiSI-F-SwaI fragment was obtained. Next, a PCR reaction was carried out using pSeV18+/PLmutTSΔF as a template and using primers F-SwaI-N (5'-GAAAAGATGAATTTAAATTGTGCACC-CATC-3') (SEQ ID NO:104) and PacI-C (5'-ATATTTAAT-TAACCAAGCACTCACAAGGG-3') (SEQ ID NO:105), and F-SwaI-PacIgrag fragment was obtained. Next, a PCR reaction was carried out using the AsiSI-F-SwaI fragment and the F-SwaI-PacI fragment as templates and using primers AsiSI-F—N and PacI-C. This product was digested with AsiSI and PacI and cloned into pSeV18+/PLmutTSΔFver2, and thus pSeV18+/PLmutTSΔM-SwaI was obtained. Next, a PCR reaction was carried out using pSeV18+/PLmutTSΔM-SwaI as a template and using primers AsiSI-F—N and F-SwaI-Cver2 (5'-GTGCACATTTAAATT-CATCTTTTCTCAGCC-3') (SEQ ID NO:106), and thus AsiSI-F-SwaIver2 fragment was obtained. Next, a PCR reaction was carried out using pSeV18+/PLmutTSΔM-SwaI as a template and using primers F-SwaI-Nver2 (5'-AT-GAATTTAAATGTGCACCCATCAGAGACC-3') (SEQ ID NO:107) and PacI-C, and thus F-SwaI-PacIver2 fragment was obtained. Next, a PCR reaction was carried out using the AsiSI-F-SwaIver2 fragment and the F-SwaI-PacIver2 fragment as templates and using primers AsiSI-F—N and PacI-C. This product was digested with AsiSI and PacI and cloned into pSeV18+/PLmutTSΔFver2, and thus pSeV18+/PLmutTSΔM-SwaIver2 was obtained. Next, a PCR reaction was carried out using pSeV18+/Fct14 (uPA #2)dM-GFP (Gene Therapy (2009) 16, 392-403) as a template and using primers AsiSI-Fct14 (uPA #2)-N (5'-ATATGCGATCGC-CACCATGACAGCATATAT-3') (SEQ ID NO:108) and Fct14 (uPA #2)-SwaI-C (5'-ATATATTTAAATTCAGCGGT-CATCTGGATT-3') (SEQ ID NO:109). This product was digested with AsiSI and cloned into pSeV18+/PLmutTSΔM-SwaIver2, and thus pSeV18+/TSΔM-Fct14 (uPA #2) was obtained. Next, a PCR reaction as carried out using DasherGFP as a template and using primers AsiSI-DGFP-N (5'-ATATGCGATCGCGA-CATGACTGCCCTGACCGAAGGTGC-3') (SEQ ID NO:110) and DGFP-EIS-AsiSI-C (5'-ATATGCGATCGC-GATGAACTTTCACCCTAAGTTTTTCTTACTACGGT-TACTGATAGGTATCGAG ATCG-3') (SEQ ID NO:111). This product was digested with AsiSI and cloned into pSeV18+/TSΔM-Fct14 (uPA #2), and thus pSeV18+(PF)DGFP/TSΔM-Fct14 (uPA #2) was obtained. A Sendai virus produced from the transcription product of the pSeV18+(PF)DGFP/TSΔM-Fct14 (uPA #2) is referred to as SeV(PF)DGFP/TSΔM-Fct4 (uPA #2).

29) Construction of SeV(PF)DGFP/PmiR143T2-TSΔM-Fct14 (uPA #2) Vector pSeV18+DGFP/PmiR143T2-TSΔF was digested with AscI and SbfI and cloned into pSeV18+(PF)DGFP/TSΔM-Fct14 (uPA #2), and thus pSeV18+(PF)DGFP/PmiR143T2-TSΔM-Fct14 (uPA #2) was obtained. A Sendai virus produced from the transcription product of the pSeV18+(PF) DGFP/PmiR143T2-TSΔM-Fct14 (uPA #2) vector is referred to as SeV(PF)DGFP/PmiR143T2-TSΔM-Fct14 (uPA #2).

30) Construction of SeV18+KLF4/PmiR367T1-TSΔF Vector pSeV18+KLF4/TSΔF (WO 2010/008054) was digested with NotI, and the KLF4-NotI fragment thus obtained was cloned into pSeV18+DGFP/PmiR367T1-TSΔF. Thus, pSeV18+KLF4P/PmiR367T1-TSΔF was obtained. A Sendai virus produced from the transcription product of the pSeV18+KLF4P/PmiR367T1-TSΔF vector is referred to as SeV18+KLF4P/PmiR367T1-TSΔF.

31) Construction of SeV18+KLF4/PmiR367T2-TSΔF Vector

The KLF4-NotI fragment was cloned into pSeV18+ DGFP/PmiR367T2-TSΔF, and thus pSeV18+KLF4P/PmiR367T2-TSΔF was obtained. A Sendai virus produced from the transcription product of the pSeV18+KLF4P/PmiR367T2-TSΔF vector is referred to as SeV18+KLF4P/PmiR367T2-TSΔF.

32) Construction of SeV18+KLF4/PmiR367T2m2-TSΔF Vector

The KLF4-NotI fragment was cloned into pSeV18+ DGFP/PmiR367T2m2-TSΔF, and thus pSeV18+KLF4P/PmiR367T2m2-TSΔF was obtained. A Sendai virus produced from the transcription product of the pSeV18+ KLF4P/PmiR367T2m2-TSΔF is referred to as SeV18+KLF4P/PmiR367T2m2-TSΔF.

33) Construction of SeV18+KLF4/PmiR302T2-TSΔF Vector

The KLF4-NotI fragment was cloned into pSeV18+ DGFP/PmiRTx2-TSΔF, and thus pSeV18+KLF4P/PmiR302T2-TSΔF was obtained. A Sendai virus produced from the transcription product of the pSeV18+KLF4P/PmiR302T2-TSΔF vector is referred to as SeV18+KLF4P/PmiR302T2-TSΔF.

34) Construction of SeV18+DGFP(HNL)cMYC/PsPmiR367T2-TS15ΔF Vector

First, construction of pSeV18+/PLmutTS12ΔF was carried out as follows. A PCR reaction was carried out using pSeV18+/TS12ΔF (WO 2010/008054) as a template and using primers AscI-N (5'-ATTGGCGCGCCAAGGTACTT-GATCCGTAG-3') (SEQ ID NO:112) and P-SbfI-C (5'-AATCCTGCAGGATCTAGTTGGTCAGTGAC-3') (SEQ ID NO:113). This product was digested with AscI and SbfI and cloned into pSeV18+/PLmutTSΔFver2, and thus pSeV18+/PLmutTS12ΔFver2 was obtained.

A PCR reaction was carried out using a P gene synthesized by artificial gene synthesis (sP) (SEQ ID NO:114) as a template and primers AsiSI-sP4Cmut-N (5'-GC-GATCGCGCCACCATGGATCAAGACGCCT-3') (SEQ ID NO:115) and sP4Cmut-miR367T2-C1 (5'-AATGGTGA-TAATCCACCAAGCTTCTATCTATCAATTGGTCAGGC-3') (SEQ ID NO:116), and thus AsiSI-sPmiR367T2-C1 fragment was obtained. Next, a PCR reaction was carried out using the AsiSI-sPmiR367T2-C1 fragment as a template and primers AsiSI-sP4Cmut-N and miR367T2-C2ver3 (5'-TCTTACTCGACTGAATTGCACTTTAGCAATGGT-GAATCGAATTGCACTTTAGCAATGGTGATAA TCCACC-3') (SEQ ID NO:117), and thus AsiSI-sPmiR367T2-C2 fragment was obtained. Next, a PCR reaction was carried out using the AsiSI-sPmiR367T2-C2 fragment as a template and using primers AsiSI-sP4Cmut-N and miR-EIS-AsiSI-C (5'-GCGATCGCGAACTTT-CACCCTAAGTTTTTCTTACTCGACTGAATTGCACTT-3') (SEQ ID NO:118). This product was cloned into pGEM-T Easy, and thus sPmiR367T2-AsiSI was obtained.

Next, sPmiR367T2-AsiSI was digested with AsiSI and cloned into pSeV18+/PLmutTS12ΔFver2, and thus pSeV18+/PsPmiR367T2-TS12ΔF was obtained. Next, the DGFP-NotI fragment was cloned into pSeV18+/PsPmiR367T2-TS12ΔF, and thus pSeV18+DGFP/PsPmiR367T2-TS12ΔF was obtained. Next, pSeV18+DGFP/PsPmiR367T2-TS12ΔF and pSeV(HNL)cMYC/TS15ΔF (WO 2010/008054) were digested with MluI and PacI and joined, and thus pSeV18+DGFP(HNL)cMYC/PsPmiR367T2-TS15ΔF was obtained. A Sendai virus produced from the transcription product of the pSeV18+DGFP (HNL)cMYC/PsPmiR367T2-TS15ΔF vector is referred to as SeV18+DGFP(HNL)cMYC/PsPmiR367T2-TS15ΔF.

35) Construction of SeV18+DGFP(HNL)cMYC/Pd2sPmiR367T2-TS15ΔF Vector pSeV18+DGFP(HNL)cMYC/PsPmiR367T2-TS15ΔF was digested with AscI and PacI, pSeV18+d2AG/d2PTS15ΔF (WO 2016/125364) was digested with AscI and SbfI, and pSeV18+DGFP/PsPmiR367T2-TS15ΔF was digested with SbfI and PacI. These were joined, and pSeV18+DGFP(HNL)cMYC/Pd2sPmiR367T2-TS15ΔF was obtained. A Sendai virus produced from the transcription product of the pSeV18+DGFP(HNL)cMYC/Pd2sPmiR367T2-TS15ΔF vector is referred to as SeV18+DGFP(HNL)cMYC/Pd2sPmiR367T2-TS15ΔF.

36) Construction of SeV18+DGFP(HNL)cMYC/PddsPmiR367T2-TS15ΔF Vector pSeV18+DGFP(HNL)cMYC/PsPmiR367T2-TS15ΔF was digested with AscI and PacI, pSeV18+d2AG/PddTS15ΔF (WO 2016/125364) was digested with AscI and SbfI, and pSeV18+DGFP/PsPmiR367T2-TS15ΔF was digested with SbfI and PacI. These were joined, and pSeV18+DGFP(HNL)cMYC/PddsPmiR367T2-TS15ΔF was obtained. A Sendai virus produced from the transcription product of the pSeV18+DGFP(HNL)cMYC/PddsPmiR367T2-TS15ΔF vector is referred to as SeV18+DGFP(HNL)cMYC/PddsPmiR367T2-TS15ΔF.

37) Construction of SeV18+DGFP(HNL)cMYC/PtetRsPmiR367T2-TS15ΔF Vector pSeV18+DGFP(HNL)cMYC/PsPmiR367T2-TS15ΔF was digested with AscI and PacI, pSeV18+d2AG/PtetRTS15ΔF (WO 2016/125364) was digested with AscI and SbfI, and pSeV18+DGFP/PsPmiR367T2-TS15ΔF was digested with SbfI and PacI. These were joined, and thus pSeV18+DGFP(HNL)cMYC/PtetRsPmiR367T2-TS15ΔF was obtained. A Sendai virus produced from the transcription product of the pSeV18+DGFP(HNL)cMYC/PtetRsPmiR367T2-TS15ΔF vector is referred to as SeV18+DGFP(HNL)cMYC/PtetRsPmiR367T2-TS15ΔF.

Figure 5A:
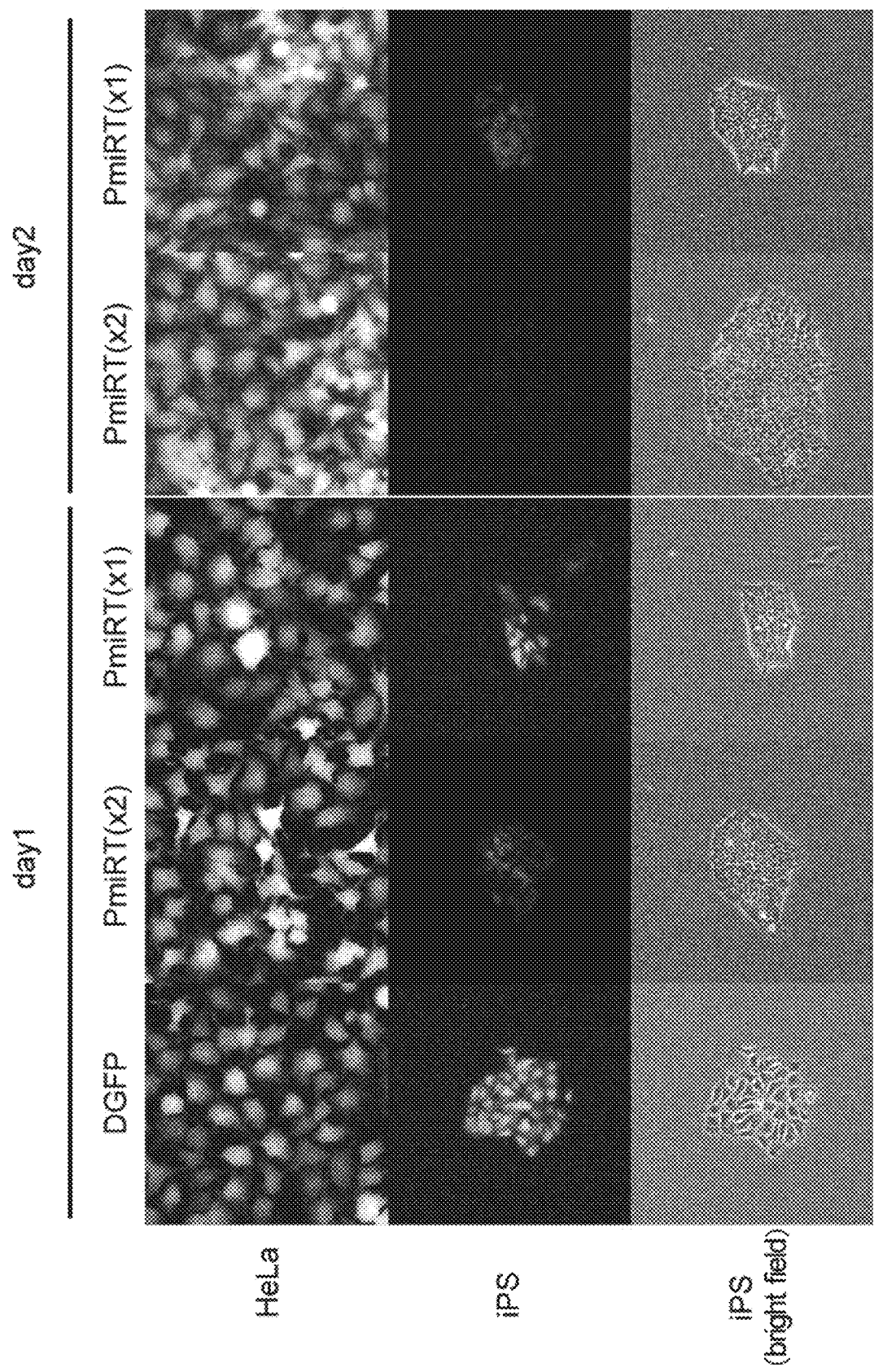
FIG. 5A is a set of pictures showing an investigation of the number of repetitions of microRNA target sequences. PmiRTx2 in which miR302T2, a two-repeat sequence of a target sequence of miR-302, was added to the P gene, and PmiRTx1 in which miR302T1, a single target sequence of miR-302, was added to the P gene, also exhibited an expression suppression effect. PmiRTx2 exhibited an expression suppression effect equivalent to that of PmiRT, in which the number of repetitions of the microRNA target sequence was four times, on Day 2, to which the culture period had been prolonged.
Figure 5B:
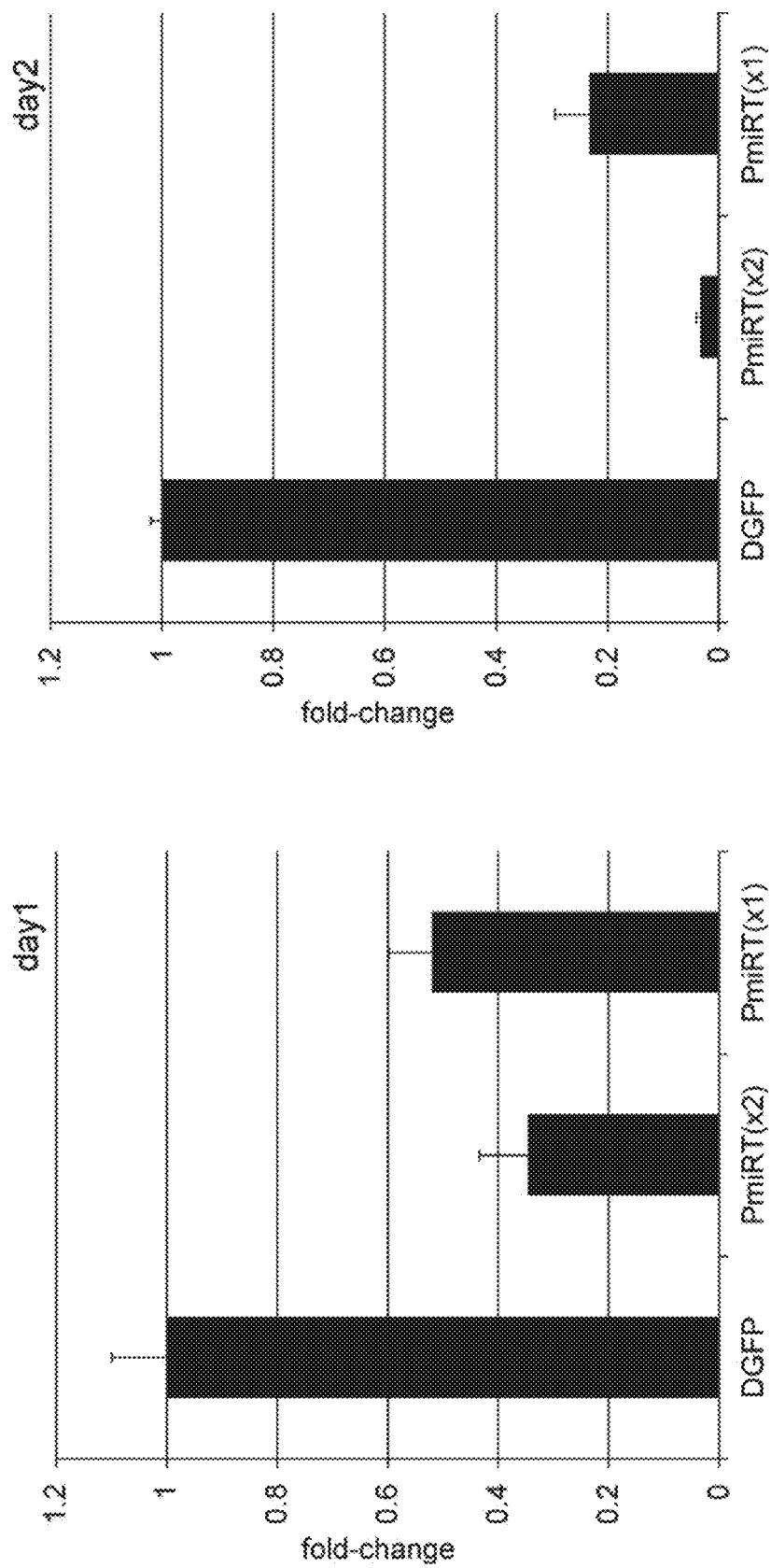
FIG. 5B is a set of diagrams showing a continuation of FIG. 5A.

In Examples 1 to 7, unless particularly stated otherwise, a product obtained by adding a sequence (miR302T1) having one microRNA target sequence (miR-302 target sequence) is described as "miRT×1"; a product obtained by adding a two-repeat sequence (miR302T2) is described as "miRT×2" (in FIG. 5, "miRT(×1)" and "miRT(×2)", respectively); and a product obtained by adding a four-repeat sequence (miR302T4) is described as "miRT".

Example 1

Figure 2A:
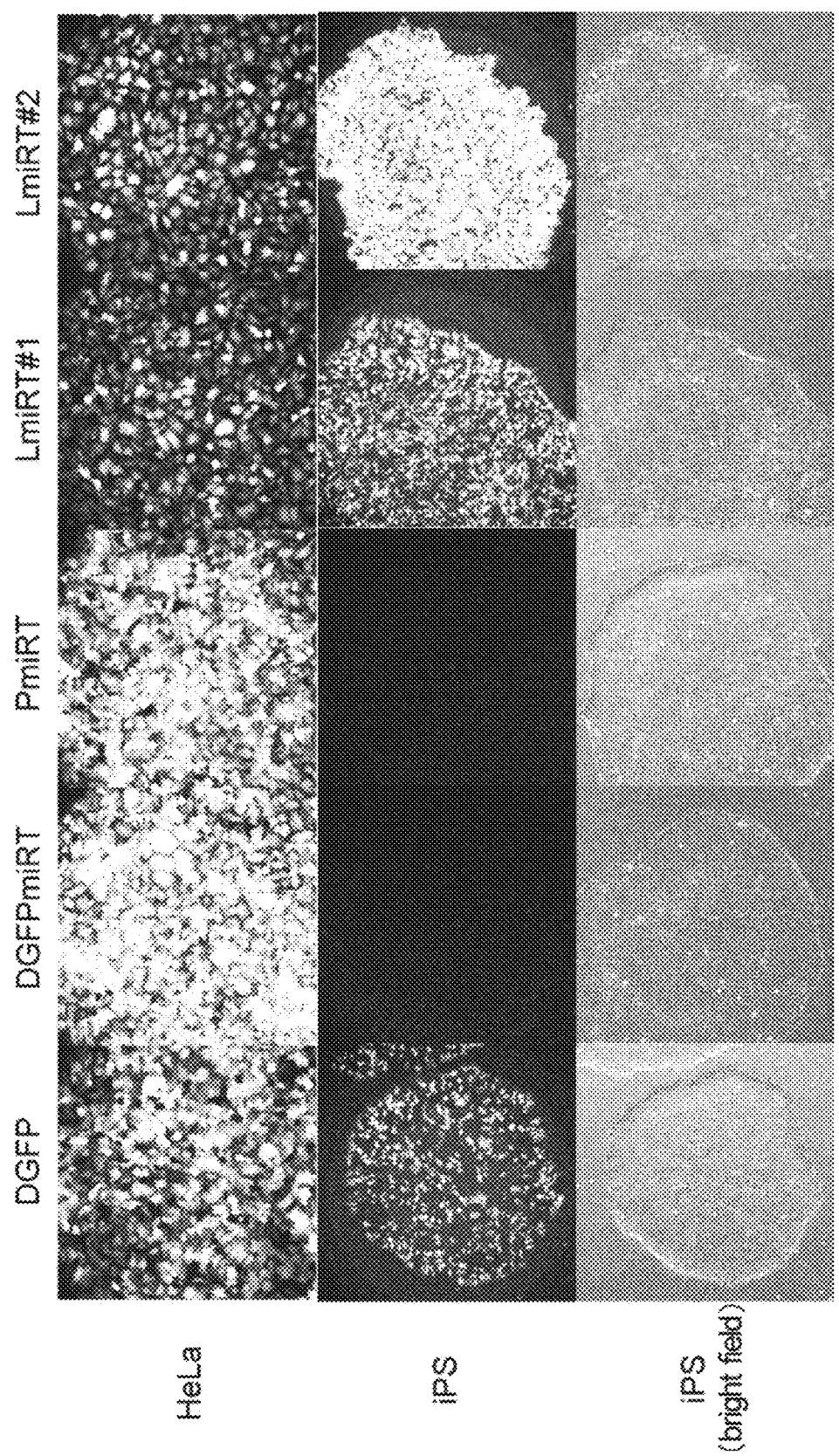
FIG. 2A is a set of pictures showing that gene expression of vectors can be controlled by adding microRNA target sequences. When HeLa cells were infected with DGFPmiRT or PmiRT, which are vectors obtained by adding miR302T4, which is a four-fold repeat of a target sequence of miR-302 cluster, to DGFP and P gene, respectively, fluorescence of DGFP was observed; however, in iPS cells expressing miR-302, fluorescence was hardly observed. On the other hand, in regard to LmiRT #1 vector in which miR-302T4 has been added to the L gene, an increase in the fluorescence of DGFP was observed in iPS cells expressing miR-302. The fluorescence intensity of LmiRT #2, in which the loading position of the microRNA target sequence was shifted to the 3'-side compared to that of the L gene was 6.5 times the intensity of DGFP.
Figure 2B:
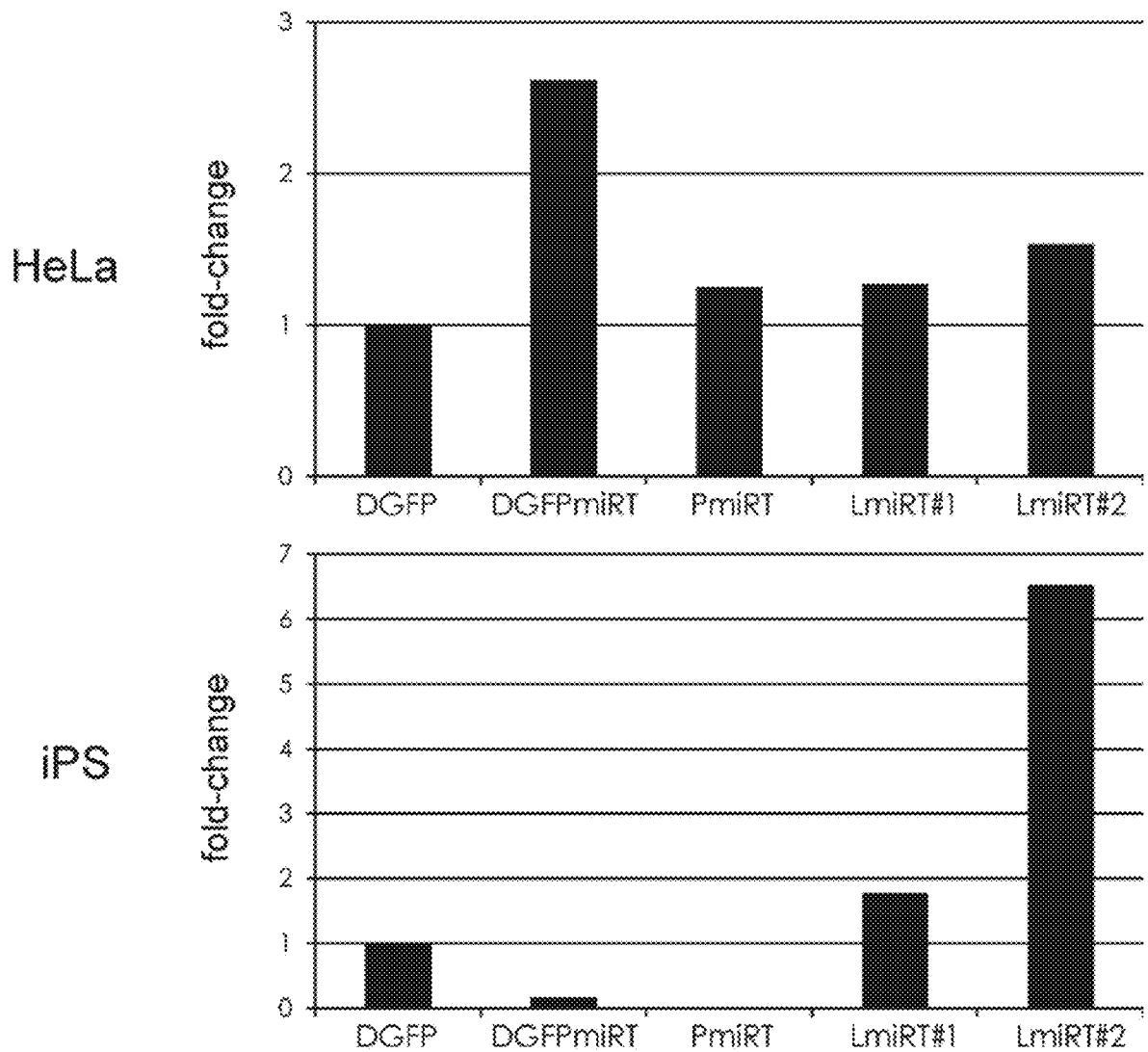
FIG. 2B is a set of diagrams showing a continuation of FIG. 2A.

HeLa cells were inoculated on a 12-well plate at a concentration of $1 \times 10^5$ cells/well, and BJ cell-derived iPS cells were inoculated on a 12-well plate. The HeLa cells and the iPS cells were infected with SeV18+DGFP/TSΔF (DGFP); SeV18+DGFPmiRT/TSΔF(DGFPmiRT), which was a vector having miR302T4 added thereto, while miR302T4 was a four-repeat sequence of a target sequence of the miR-302 cluster; SeV18+DGFP/PmiRT-TSΔF (PmiRT); SeV18+DGFP/LmiRT #1-TSΔF(LmiRT #1); and SeV18+DGFP/LmiRT #2-TSΔF(LmiRT #2) at MOI=5 at 35° C., and an observation with a fluorescence microscope and measurement using a fluorescence plate reader were made on Day 1. As a result, fluorescence of DGFP, DGFPmiRT, PmiRT, LmiRT #1, and LmiRT #2 was observed in the HeLa cells, while quenching of fluorescence of DGFPmiRT and PmiRT was observed in the iPS cells expressing miR-302. Meanwhile, with regard to the LmiRT #1 vector having miR-302T4 added to the L gene, an increase in the fluorescence intensity of DGFP was observed in the iPS cells expressing miR-302. Furthermore, for LmiRT #2 in which the loading position of the microRNA target sequence was shifted to the 3'-side compared to that of the L gene, 6.5 times stronger fluorescence was observed compared to DGFP (FIG. 2).

Figure 3:
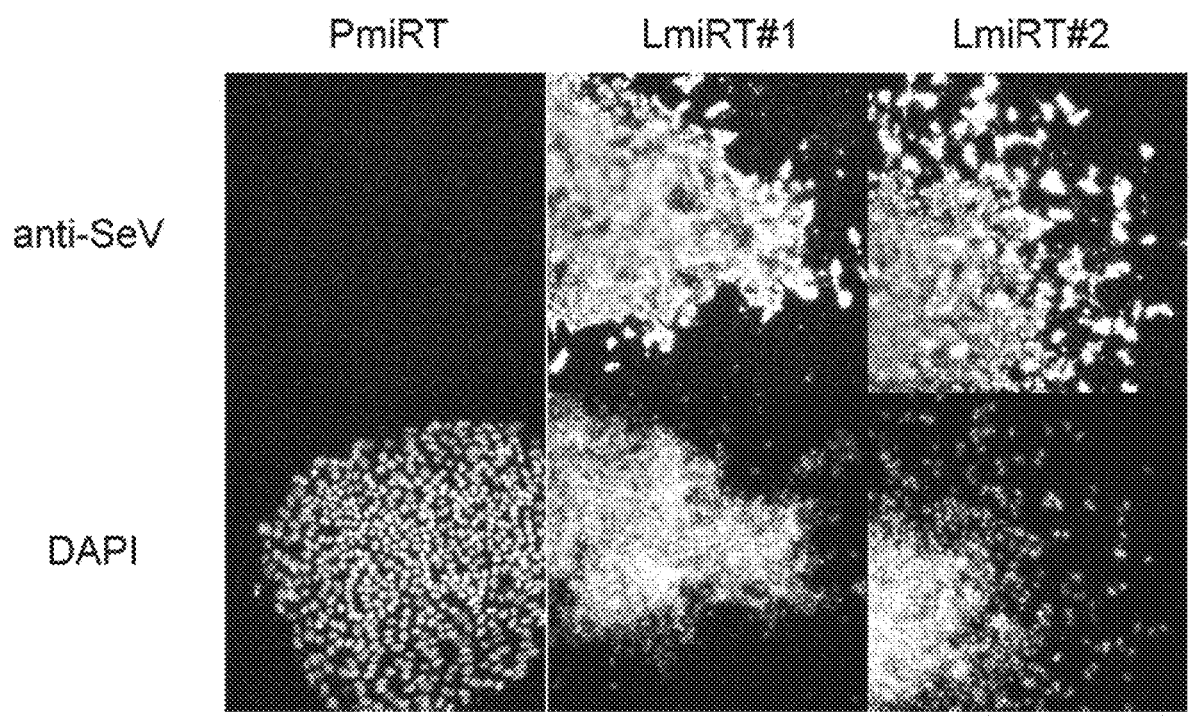
FIG. 3 is a set of pictures showing, by SeV antibody staining, that vectors have been removed by adding microRNA target sequences. SeV antibody staining was performed 22 days after vector infection, and PmiRT was found to be SeV antibody-negative, while LmiRT #1 and LmiRT #2 were found to be SeV antibody-positive.

Example 2 iPS cells were infected with PmiRT, LmiRT #1, and LmiRT #2 at 35° C., and after fluorescence expression was observed on Day 1, the cells were cultured for 22 days at 37° C. SeV antibody staining was carried out on Day 22, and it was found that PmiRT was SeV antibody-negative, while LmiRT #1 and LmiRT #2 were SeV antibody-positive (FIG. 3).

Example 3

Figure 4A:
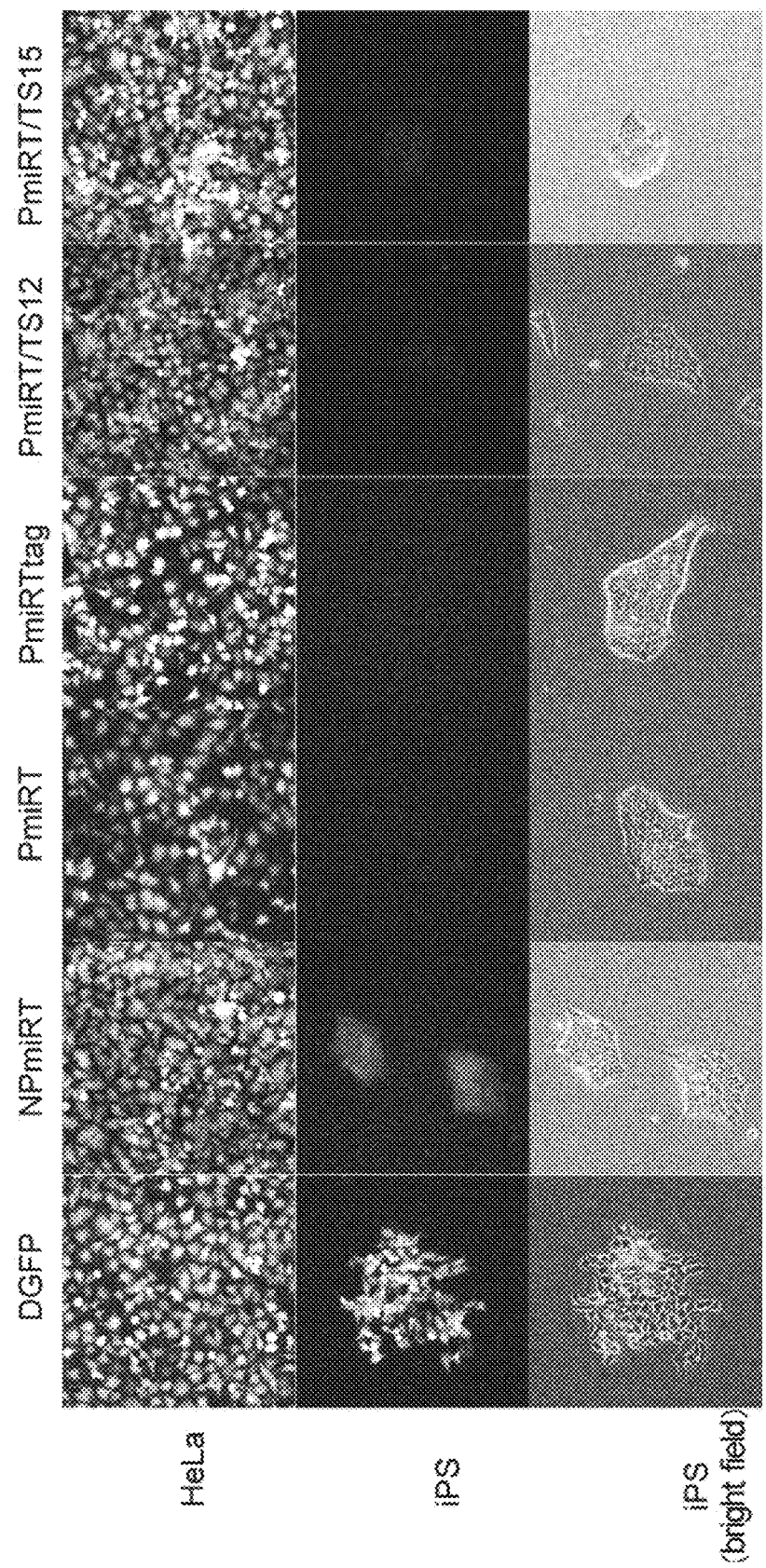
FIG. 4A is a set of pictures showing an investigation of the position at which a microRNA target sequence is added, or the vector skeleton. In regard to NPmiRT in which miR-302T4 was added to the NP gene, expression was suppressed compared to DGFP in which no microRNA target sequence was added; however, the suppression of expression was weak compared to the case in which a microRNA target sequence was added to the P gene. In PmiRTtag in which miR-302T4 was added to the coding region of the P gene, an effect equivalent to that of PmiRT was obtained. Also in PmiRT having the TS12 and TS15 skeletons with intensified temperature sensitivity, a similar expression suppression effect was obtained.
Figure 4B:
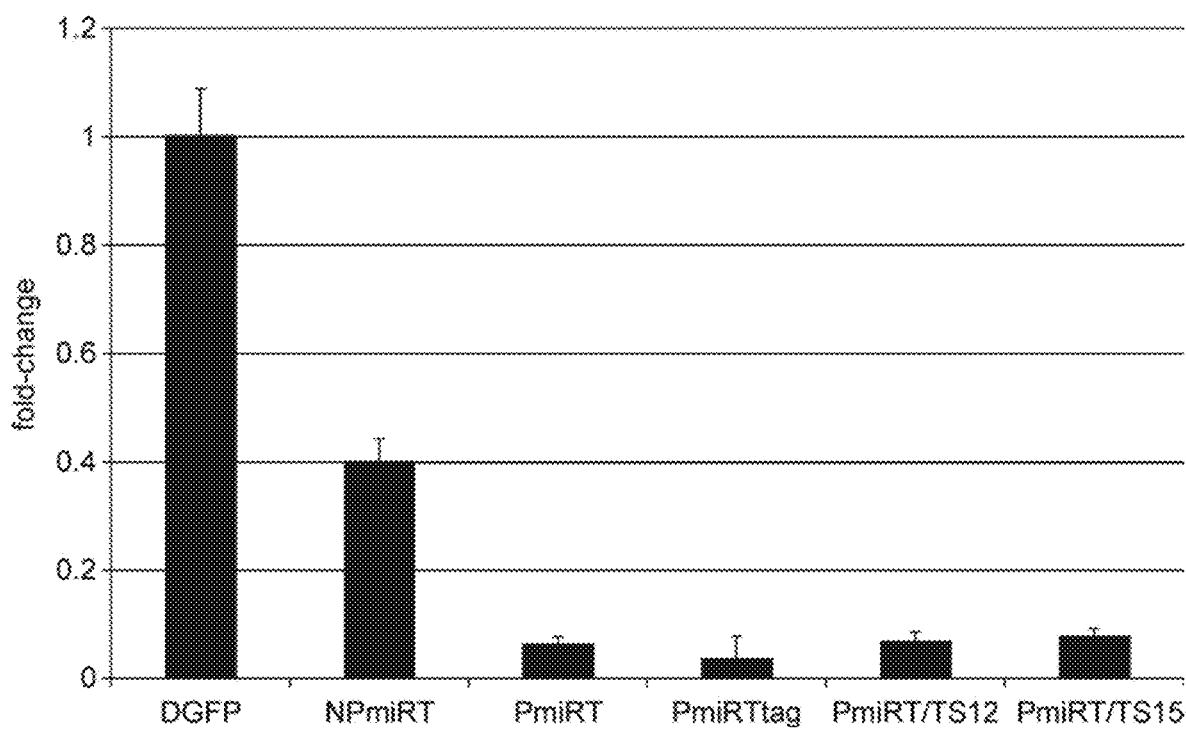
FIG. 4B is a diagram showing a continuation of FIG. 4A.

HeLa cells and iPS cells were infected with DGFP, PmiRT, SeV18+DGFP/NPmiRT-TSΔF (NPmiRT), SeV18+DGFP/PmiRTtag-TSΔF (PmiRTtag), SeV18+DGFP/PmiRT-TS12ΔF (PmiRT/TS12), and SeV18+DGFP/PmiRT-TS15ΔF (PmiRT/TS15) at 35° C., and an observation with a fluorescence microscope and an image analysis by Meta-Morph (Molecular Devices, LLC) were carried out on Day 1. As a result, fluorescence of DGFP, NPmiRT, PmiRT, PmiRTtag, PmiRT/TS12, and PmiRT/TS15 was observed in the HeLa cells, while in the iPS cells, expression of NPmiRT having miR-302T4 added to the NP gene was suppressed to about 40% compared to DGFP that did not have any added microRNA target sequence. However, this was weak suppression of expression compared to the case in which the microRNA target sequence was added to the P gene. The fluorescence intensity of PmiRTtag having miR-302T4 added to the coding region of the P gene was 10% or less compared to the fluorescence intensity of DGFP, and an expression suppression effect equivalent to that of PmiRT was obtained. Also for PmiRT having the TS12 and TS15 skeletons and having intensified temperature sensitivity, an expression suppression effect equivalent to that of PmiRT having the TS skeleton was obtained (FIG. 4).

Example 4

HeLa cells and iPS cells were infected with DGFP, SeV18+DGFP/PmiRTx2-TSΔF (PmiRTx2), and SeV18+DGFP/PmiRTx1-TSΔF (PmiRTx1) at 35° C., and an observation with a fluorescence microscope and an image analysis by MetaMorph were carried out on Day 1 and Day 2. As a result, fluorescence of DGFP, PmiRTx2, and PmiRTx1 was observed in the HeLa cells, while in the iPS cells, the fluorescence intensity of PmiRTx2 decreased to 40% or less compared to that of DGFP on Day 1, and the fluorescence intensity of PmiRTx2 decreased to 10% or less on Day 2. Also for the fluorescence intensity of PmiRTx1, a decrease to 30% or less of the fluorescence intensity of DGFP was observed on Day 2 (FIG. 5). PmiRTx2 obtained by adding miR302T2, which was a two-repeat sequence of a target sequence of miR-302, to the P gene, and PmiRTx1 obtained by adding miR302T1, which was a single target sequence of miR-302, also exhibited an expression suppression effect. PmiRTx2 exhibited an expression suppression effect equivalent to that of PmiRT, in which the number of repetition of the microRNA target sequence was four times, on Day 2, to which the culturing time had been prolonged.

Example 5

Figure 6:
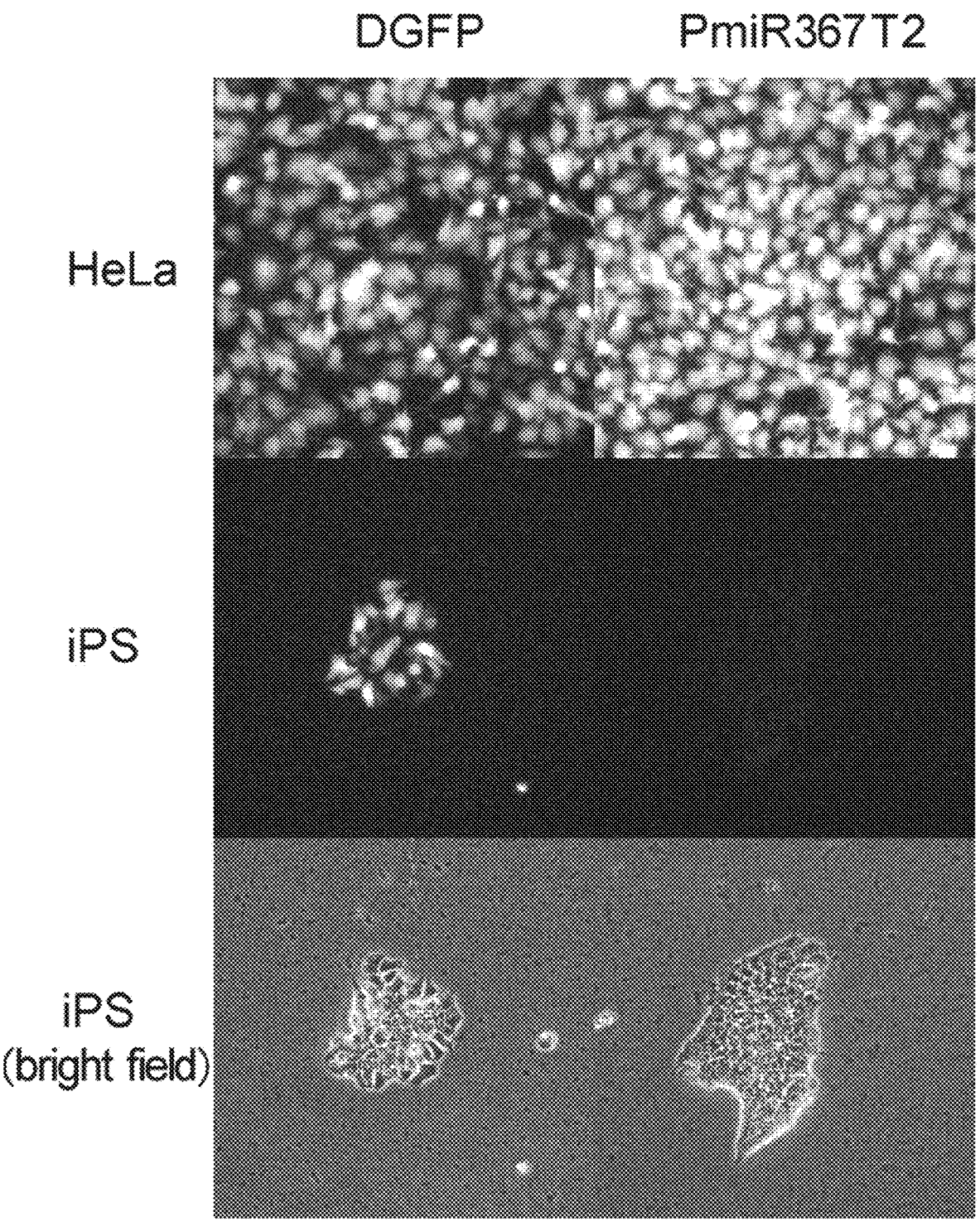
FIG. 6 is a set of pictures showing that the effect is obtained also with other microRNA target sequences that are expressed in iPS cells. PmiR367T2 in which miR367T2, a two-repeat sequence of a target sequence of miR-367, was added to the P gene also exhibited an expression suppression effect.

HeLa cells and iPS cells were infected with DGFP and SeV18+DGFP/PmiR367T2-TSΔF (PmiR367T2) at 35° C., and an observation with a fluorescence microscope was carried out on Day 1. PmiR367T2 was a product obtained by adding miR367T2, which was a two-repeat sequence of a target sequence of miR-367, to the P gene. As a result, in the HeLa cells, fluorescence of DGFP and PmiR367T2 was observed, while in the iPS cells, a decrease in the fluorescence intensity of PmiR367T2 compared to DGFP was observed (FIG. 6). This implies that effects are also obtained with microRNA target sequences other than the miR-302 cluster that is expressed in iPS cells.

Example 6

Figure 7:
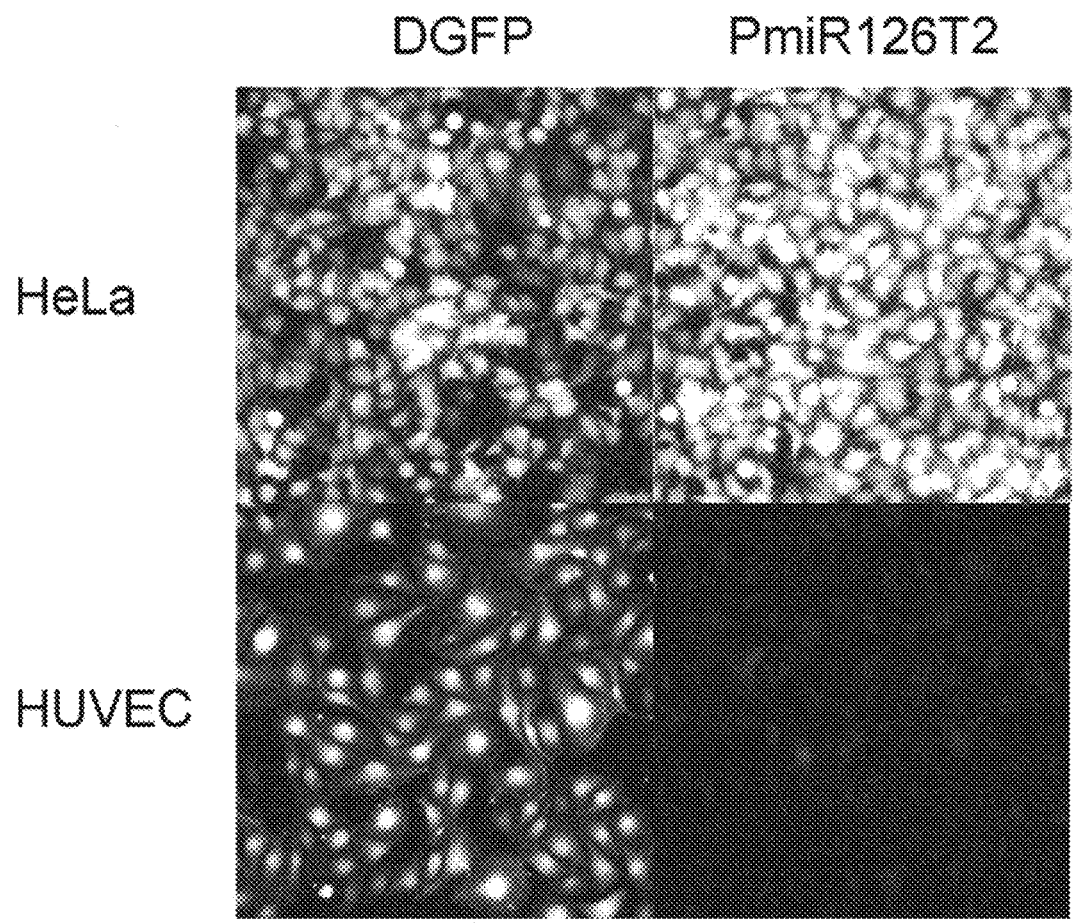
FIG. 7 is a set of pictures showing that the effect is also obtained with other microRNA target sequences that are expressed in differentiated cells. PmiR126T2 in which a target sequence of miR-126 (two-fold repeat) that is known to be expressed in vascular endothelial cells in the mesoderm system was added to the P gene, also exhibited an expression suppression effect.

HeLa cells and vascular endothelia cells HUVEC were infected with DGFP and SeV18+DGFP/PmiR126T2-TSΔF (PmiR126T2) (vector obtained by adding miR126T2, which was a two-repeat sequence of a target sequence of miR-126, to the P gene) at 35° C., and an observation with a fluorescence microscope was carried out on Day 1. As a result, fluorescence of DGFP and PmiR126T2 was observed in the HeLa cells, while in HUVEC, a decrease in the fluorescence intensity of PmiR126T2 compared to that of DGFP was observed (FIG. 7). This implies that PmiR126T2, in which a target sequence of miR-126 that is expressed in the vascular endothelial cells of the mesoderm had been added to the P gene, also exhibited an expression suppression effect, and it is implied that vectors can be controlled by microRNAs that are respectively cell-specifically expressed in differentiated cells.

Example 7

Figure 8:
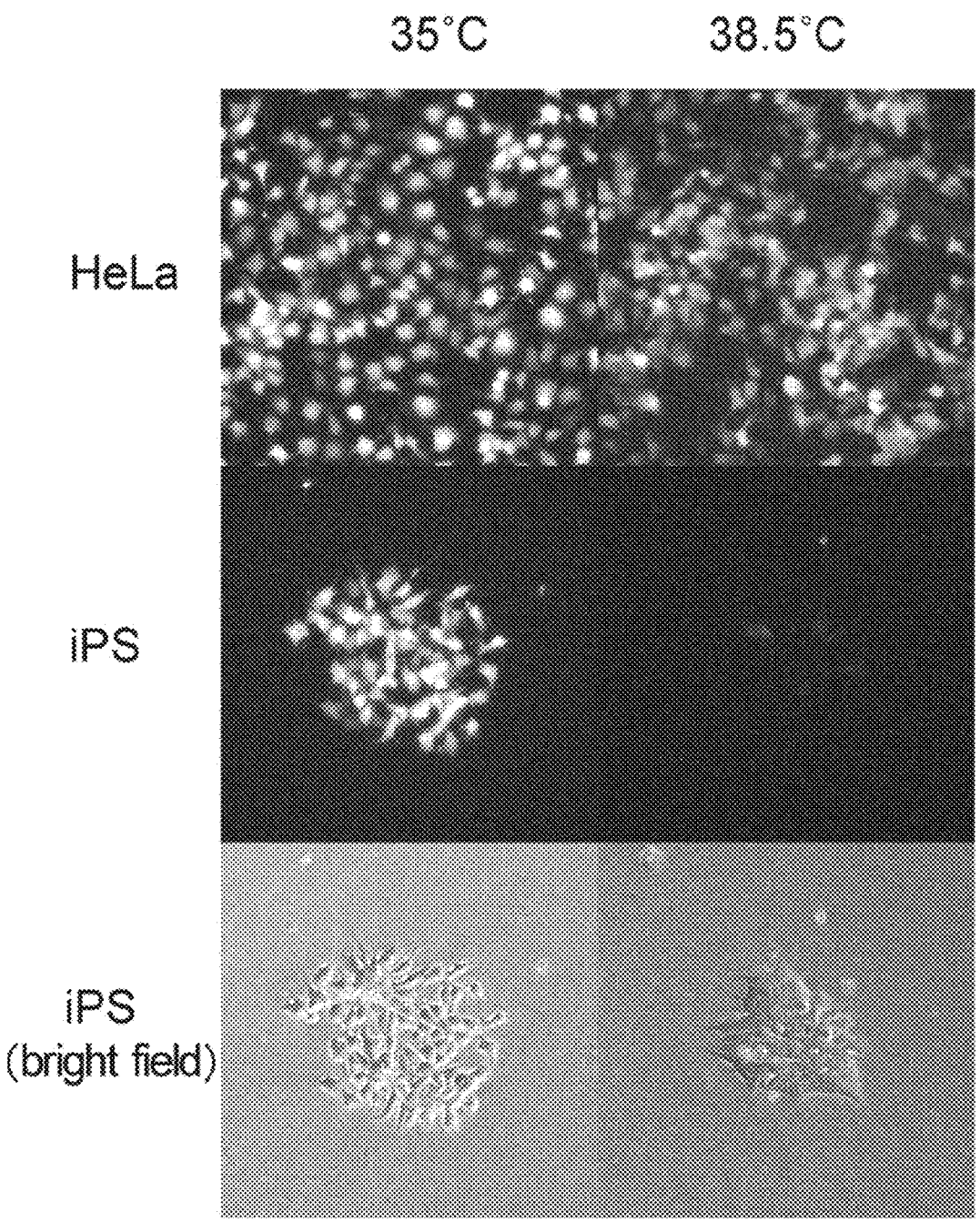
FIG. 8 is a set of diagrams showing that the effect of using a microRNA target sequence is obtained even in a vector that does not include a temperature-sensitive mutation. When miR-302T4 was added to the P gene of a SeV vector that did not include a temperature-sensitive mutation, an expression suppression effect was obtained in a culturing environment at 38.5° C.

HeLa cells and iPS cells were infected with SeV18+DGFP/PmiRT-ΔF (PmiRTdF) at 35° C. and 38.5° C., and an observation with a fluorescence microscope was carried out on Day 1. miR-302T4 was added to the P gene of a SeV vector that did not contain temperature-sensitive mutations. As a result, fluorescence of PmiRTdF was observed in the HeLa cells at 35° C. and 38.5° C., while in the iPS cells, a decrease in the fluorescence intensity of PmiRTdF was observed at 38.5° C. compared to that at 35° C. (FIG. 8). This implies that vectors can be controlled by means of microRNA target sequences even in vectors that do not contain temperature-sensitive mutations.

Example 8

Figure 9:
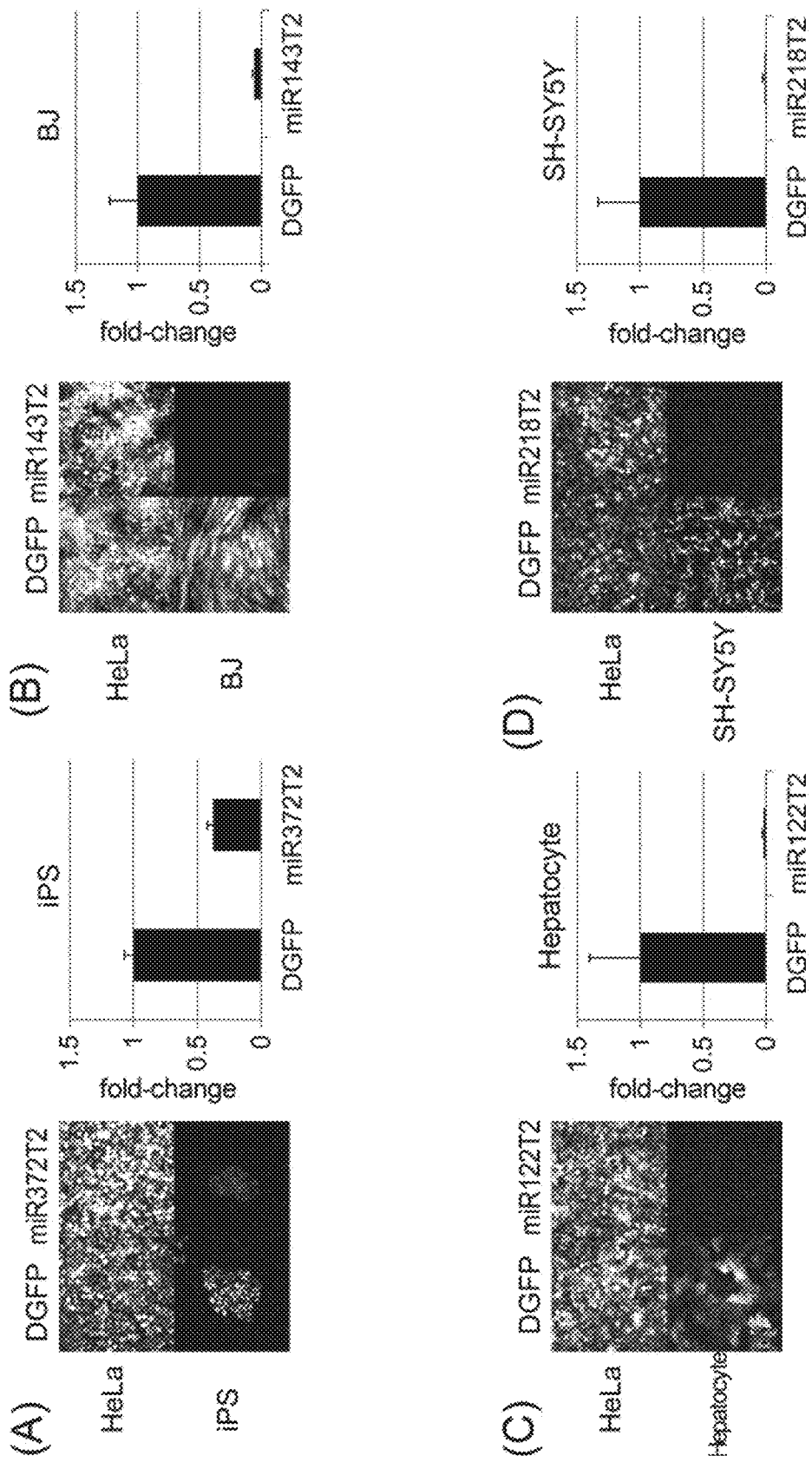
FIG. 9 is a set of diagrams showing an effect of suppressing expression in various cells of vectors carrying target sequences of miR-372, miR-218, miR-122, and miR-143. The expression suppression effects of vectors carrying target sequences (two-fold repeat) of miR-372 (A), which is known to be expressed in iPS cells; miR-143 (B), which is known to be expressed in normal cells; miR-122 (C), which is known to be expressed in the liver cells of the endoderm system; and miR-218 (D), which is known to be expressed in the nerve cells of the ectoderm system.

HeLa cells and iPS cells were infected with DGFP and SeV18+DGFP/PmiR372T2-TSΔF (PmiR372T2) at 35° C., and an observation with a fluorescence microscope was carried out on Day 2. PmiR372T2 was a product obtained by adding miR372T2, which was a two-repeat sequence of a target sequence of miR-372, to the P gene. As a result, fluorescence of DGFP and PmiR372T2 was observed in the HeLa cells, while in the iPS cells, a decrease in the fluorescence intensity of PmiR372T2 compared to that of DGFP was observed (FIG. 9A). This implies that effects are also obtained with microRNA target sequences other than the miR-302 cluster that is expressed in iPS cells.

Example 9

HeLa cells and BJ cells were infected with DGFP and SeV18+DGFP/PmiR143T2-TSΔF (PmiR143T2) at 37° C., and an observation with a fluorescence microscope was carried out on Day 2. PmiR143T2 was a product obtained by adding miR143T2, which was a two-repeat sequence of a target sequence of miR-143, to the P gene. As a result, fluorescence of DGFP and PmiR143T2 was observed in the HeLa cells, while in the BJ cells, a decrease in the fluorescence intensity of PmiR143T2 compared to that of DGFP was observed (FIG. 9B). BJ cells are used as a model of normal cells that have not cancerated, and this implies that PmiR143T2 obtained by adding a target sequence of miR-143 that is expressed in normal cells to the P gene, also exhibited an expression suppression effect, and that vectors can be controlled by microRNAs that show different expression behavior in normal cells and cancer cells.

Example 10

HeLa cells and rat liver cells were infected with DGFP and SeV18+DGFP/PmiR122T2-TSΔF (PmiR122T2) at 37° C., and an observation with a fluorescence microscope was carried out on Day 1. PmiR122T2 was a product obtained by adding miR122T2, which was a two-repeat sequence of a target sequence of miR-122, to the P gene. As a result, fluorescence of DGFP and PmiR122T2 was observed in the HeLa cells, while in the liver cells, a decrease in the fluorescence intensity of PmiR122T2 compared to that of DGFP was observed (FIG. 9C). This implies that PmiR122T2 obtained by adding a target sequence of miR-122 that is expressed in the liver cells of the endoderm to the P gene also exhibited an expression suppression effect, and it is implied that vectors can be controlled by microRNAs that are respectively cell-specifically expressed in differentiated cells.

Example 11

HeLa cells and SH-SY5Y cells were infected with DGFP and SeV18+DGFP/PmiR218T2-TSΔF (PmiR218T2) at 35° C., and an observation with a fluorescence microscope was carried out on Day 1. PmiR218T2 was a product obtained by adding miR218T2, which was a two-repeat sequence of a target sequence of miR-218, to the P gene. As a result, fluorescence of DGFP and PmiR218T2 was observed in the HeLa cells, while in the SH-SY5Y cells, a decrease in the fluorescence intensity of PmiR218T2 compared to that of DGFP was observed (FIG. 9D). SH-SY5Y cells derived from neuroblastoma are used as a nerve cell model, and this implies that PmiR218T2 obtained by adding a target sequence of miR-218 that is expressed in the nerve cells of the ectoderm to the P gene also exhibited an expression suppression effect, and that vectors can be controlled by microRNAs that are respectively cell-specifically expressed in differentiated cells.

Example 12

Figure 10:
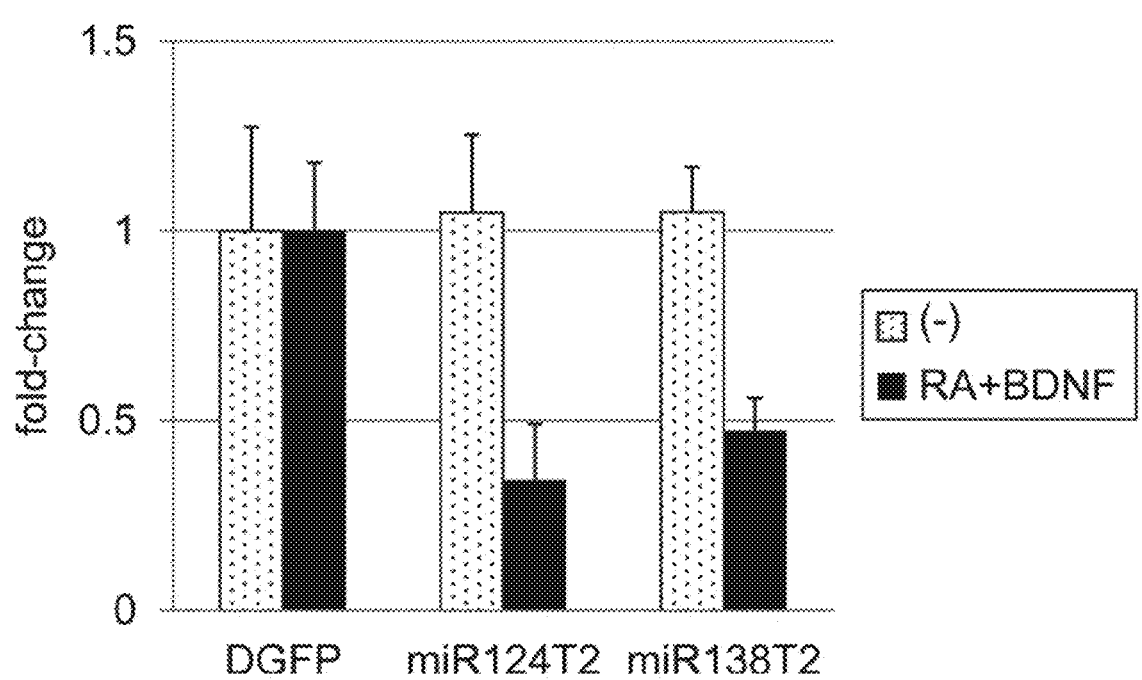
FIG. 10 is a diagram showing a specific expression suppression effect of vectors carrying target sequences of miR-124 and miR-138 in the differentiation stage of nerve cells.

SH-SY5Y cells and SH-SY5Y cells that had been subjected to neuronal differentiation for 3 days with 10 μM retinoic acid (RA), 10% FBS, and DMEM/F12, were infected with DGFP, SeV18+DGFP/PmiR124T2-TSΔF (PmiR124T2), and SeV18+DGFP/PmiR138T2-TSΔF (PmiR138T2) at 35° C., and an observation with a fluorescence microscope was carried out on Day 3. For the neurodifferentiated cells, the medium was replaced with 10 μM RA, 2% FBS, and DMEM/F12 at the same time with infection, and the next day, the medium was replaced with 10 ng/mL BDNF and serum-free DMEM/F12. PmiR124T2 and PmiR138T2 were obtained by adding miR124T2 and miR138T2, which were two-repeat sequences of target sequences of miR-124 and miR-138, respectively, to the P gene. As a result, in the SH-SY5Y cells that were not differentiated, fluorescence of DGFP, PmiR124T2, and PmiR138T2 was observed, while in the neurodifferentiated SH-SY5Y cells, decreases in the fluorescence intensities of PmiR124T2 and PmiR138T2 were observed compared to DGFP (FIG. 10). This implies that PmiR124T2 and PmiR138T2 obtained by adding target sequences of miR-124 and miR-138, respectively, which are expressed in differentiated nerve cells, also exhibit an expression suppression effect, and that vectors can be controlled by microRNAs that are respectively cell-specifically expressed in cells in different differentiation stages. PmiR218T2 exhibited an expression suppression effect in an undifferentiated nerve cell model, and PmiR124T2 and PmiR138T2 exhibited an expression suppression effect in a differentiated nerve cells model.

Example 3

Figure 11:
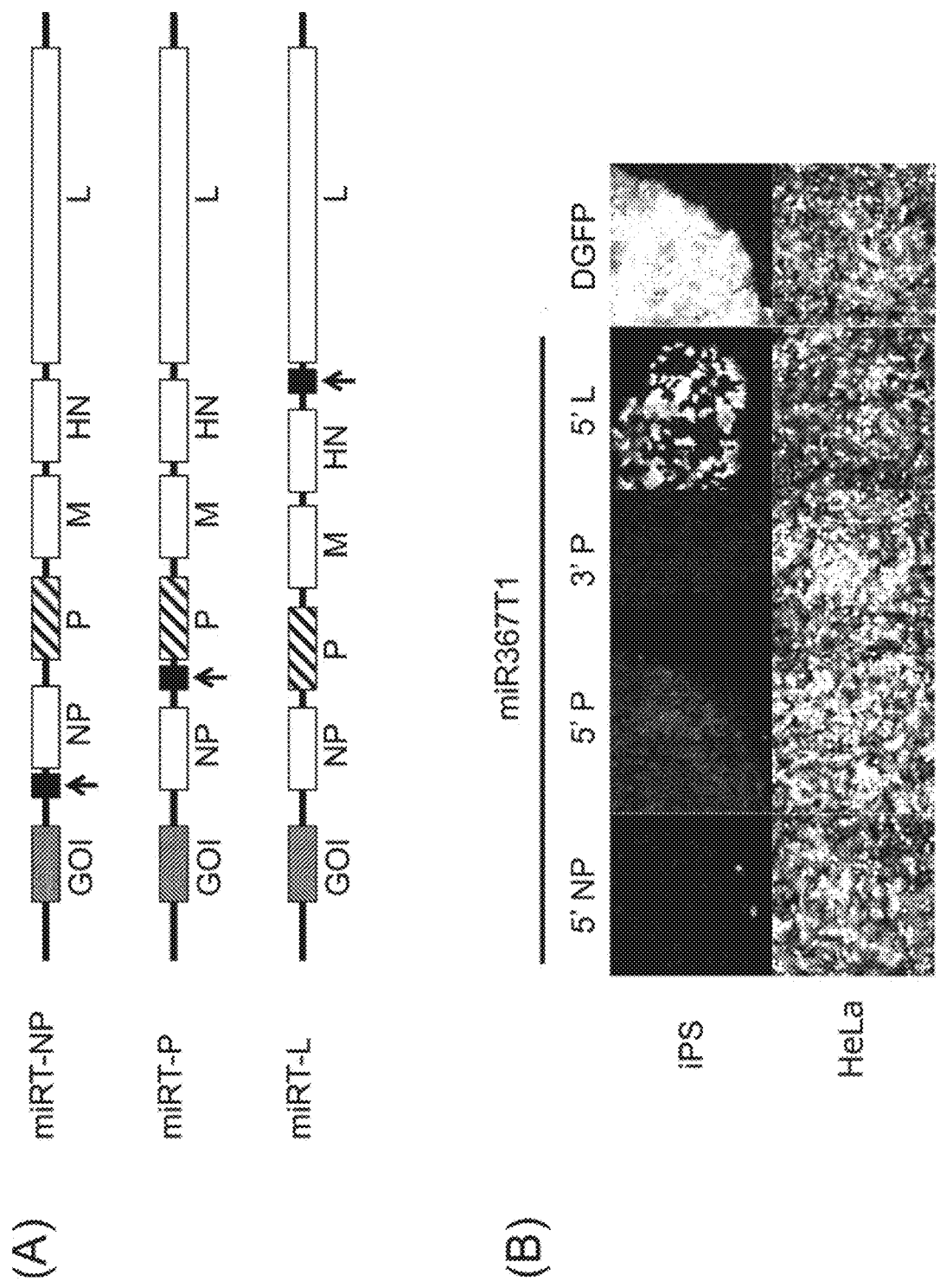
FIG. 11 is a set of diagrams showing the effect in a case where a microRNA target sequence was added to the 5'-side of each viral gene (3'-side in the genome). When the microRNA target sequence was applied to the 5'-side of NP and P, the function as a microRNA target sequence (expression suppression effect) was exhibited; however, when the microRNA target sequence was applied to the 5'-side of L, the cell-specific effect as a microRNA target sequence was not exhibited.

HeLa cells and iPS cells were infected with DGFP, SeV18+DGFP/PmiR367T1-TSΔF (PmiR367T1), SeV18+DGFP/miR367T1-P-TSΔF (miR367T1-P), SeV18+DGFP/miR367T1-NP-TSΔF (miR367T1-NP), and SeV18+DGFP/miR367T1-L-TSΔF (miR367T1-L) at 37° C., and an observation with a fluorescence microscope was carried out on Day 5. As a result, miR367T1-L did not exhibit a cell-specific expression suppression effect. In the HeLa cells, equal degrees of fluorescence of DGFP, miR367T1-NP, miR367T1-P, and PmiR367T1 was observed, while in the iPS cells, expression of miR367T1-NP, miR367T1-P, and PmiR367T1 was expressed (FIG. 11). There were occasions in which the addition of a microRNA target sequence on the 5'-side of the L gene in the iPS cells did not exhibit a cell-specific expression suppression effect, unlike the case of the P gene. The addition of the miR-367 target sequence on the 5'-side of the P gene exhibited a weak expression suppression effect compared to the effect provided by the addition on the 3'-side.

Example 14

Figure 12:
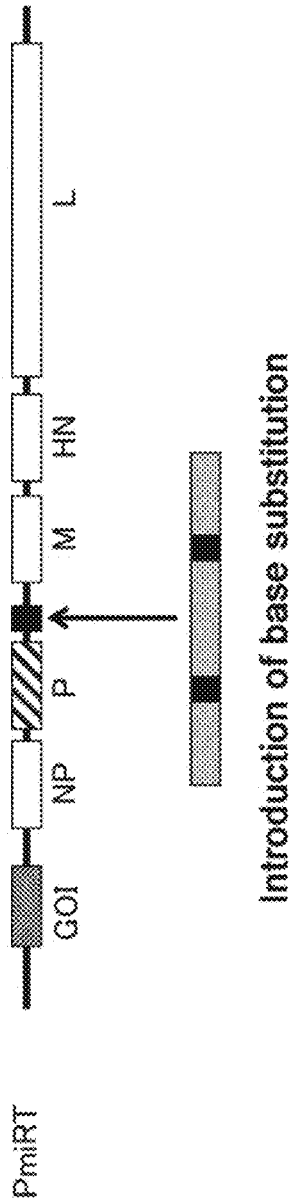
FIG. 12 is a diagram showing mutations introduced into microRNA target sequences.

HeLa cells and iPS cells were infected with DGFP, PmiR367T1, PmiR367T2, SeV18+DGFP/PmiR367T2 m1-TSΔF (PmiR367T2 m1), SeV18+DGFP/PmiR367T2m2-TSΔF (PmiR367T2m2), SeV18+DGFP/PmiR367T2m3-TSΔF (PmiR367T2m3), and SeV18+DGFP/PmiR367T2m4-TSΔF (PmiR367T2m4) at 37° C., and an observation with a fluorescence microscope was carried out on Days 1 to 5 (FIG. 12). As a result, in the HeLa cells on Day 5, equal degrees of fluorescence was expressed, while in the iPS cells, cell-specific expression suppression effects were obtained in the order of PmiR367T2>PmiR367T2 m1>PmiR367T1>PmiR367T2m2>PmiR367T2m3>PmiR367T2m4 (FIGS. 13 and 14). In the iPS cells, PmiR367T2 m1 having a single-base mutation incorporated therein exhibited a slightly decreased expression suppression effect compared to PmiR367T2. PmiR367T2m2, PmiR367T2m3, and PmiR367T2m4, which had mutations of two or more bases incorporated therein, exhibited an increase in expression on Day 2 in the iPS cells, and then exhibited an expression suppression effect on Day 5. This implies that the extent of the expression suppression can be controlled by incorporating one or more mutations into the microRNA target sequence, in addition to the number of repetitions of the target sequence.

Figure 15:
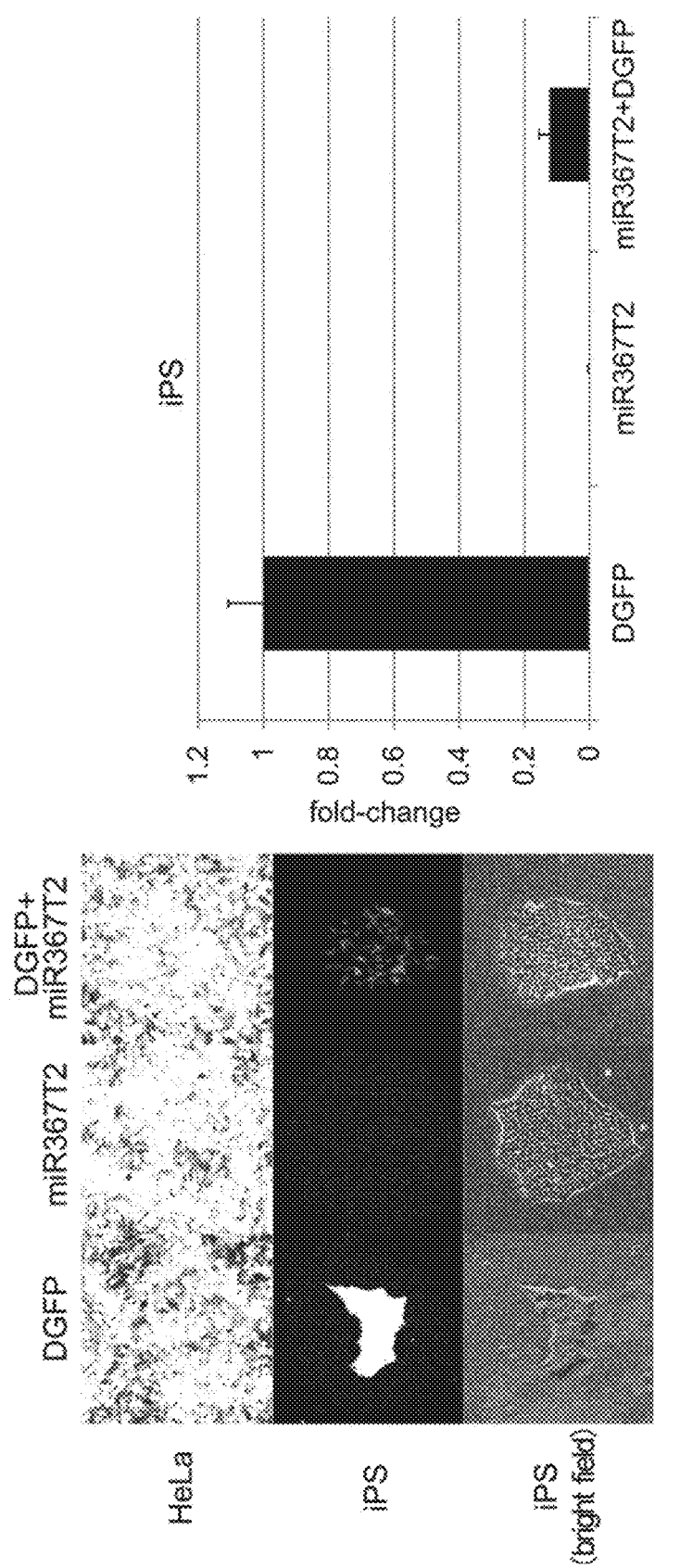
FIG. 15 is a set of diagrams showing an effect of co-infection of microRNA target sequence-carrying vectors. When a miR367 target sequence-carrying vector was co-infected, attenuation of fluorescence of DGFP was observed. The results of Day 3 are presented.

Example 15 iPS cells were infected with DGFP, PmiR367T2, or DGFP and PmiR367T2 (co-infection) at 37° C., and an observation with a fluorescence microscope was carried out on Day 3. As a result, equal degrees of fluorescence expression was observed in the HeLa cells, while in the iPS cells, expression suppression by PmiR367T2 that was co-infected with DGFP was observed (FIG. 15). This implies that expression of a vector that is co-infected with a microRNA target sequence-carrying vector can also be controlled.

Example 16

Figure 16:
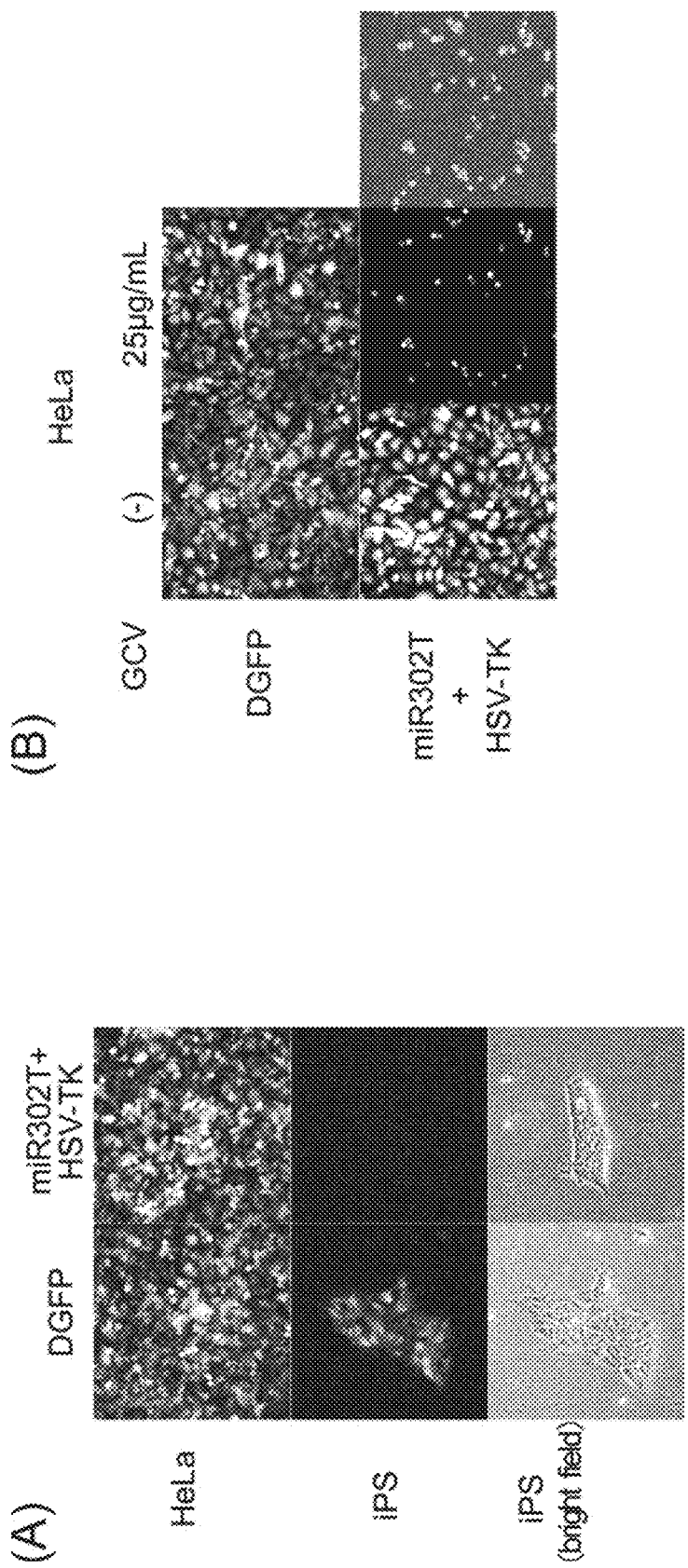
FIG. 16 is a set of diagrams showing an evaluation of microRNA target sequence+HSV-TK. A four-fold repeat sequence of the miR302 target sequence was added to the 3'-UTR of the P gene, and a suppression effect was obtained on Day 1 (Panel A). The state of cells after the addition of ganciclovir (GCV) is shown in Panel B (SeV infection on Day 5, and GCV addition on Day 3). GCV was examined at a concentration of 25 to 100 mg/mL. As shown in the pictures, when GCV was added to cells expressing HSV-TK, cell death was induced. These results show that it is possible to remove cells having residual vectors. For example, a suicide gene can be loaded into a vector for the purpose of exclusion of cells in which removal of the vector by microRNA has been insufficiently achieved.

HeLa cells and iPS cells were infected with DGFP and SeV18+DGFP(HNL)HSV-TK/PmiR302T4-TSΔF (HSV-TK/PmiR302T4) at 37° C., and an observation with a fluorescence microscope was carried out on Day 1. Next, ganciclovir (GCV) was added at 25 to 100 g/mL to these cells on Day 2, and an observation with a fluorescence microscope was carried out on Day 5. As a result, cell-specific expression suppression of HSV-TK/PmiR302T4 in the iPS cells was observed on Day 1 (FIG. 16A). In regard to the HeLa cells on Day 5, to which GCV had been added, no influence was observed even with 100 μg/mL GCV in the DGFP-infected cells, while the cells infected with HSV-TK/PmiR302T4 were annihilated with 25 μg/mL GCV (FIG. 16B). This implies that cells in which vectors have not been removed by microRNAs can also be removed when a suicide gene is used in combination.

Example 17

Figure 17:
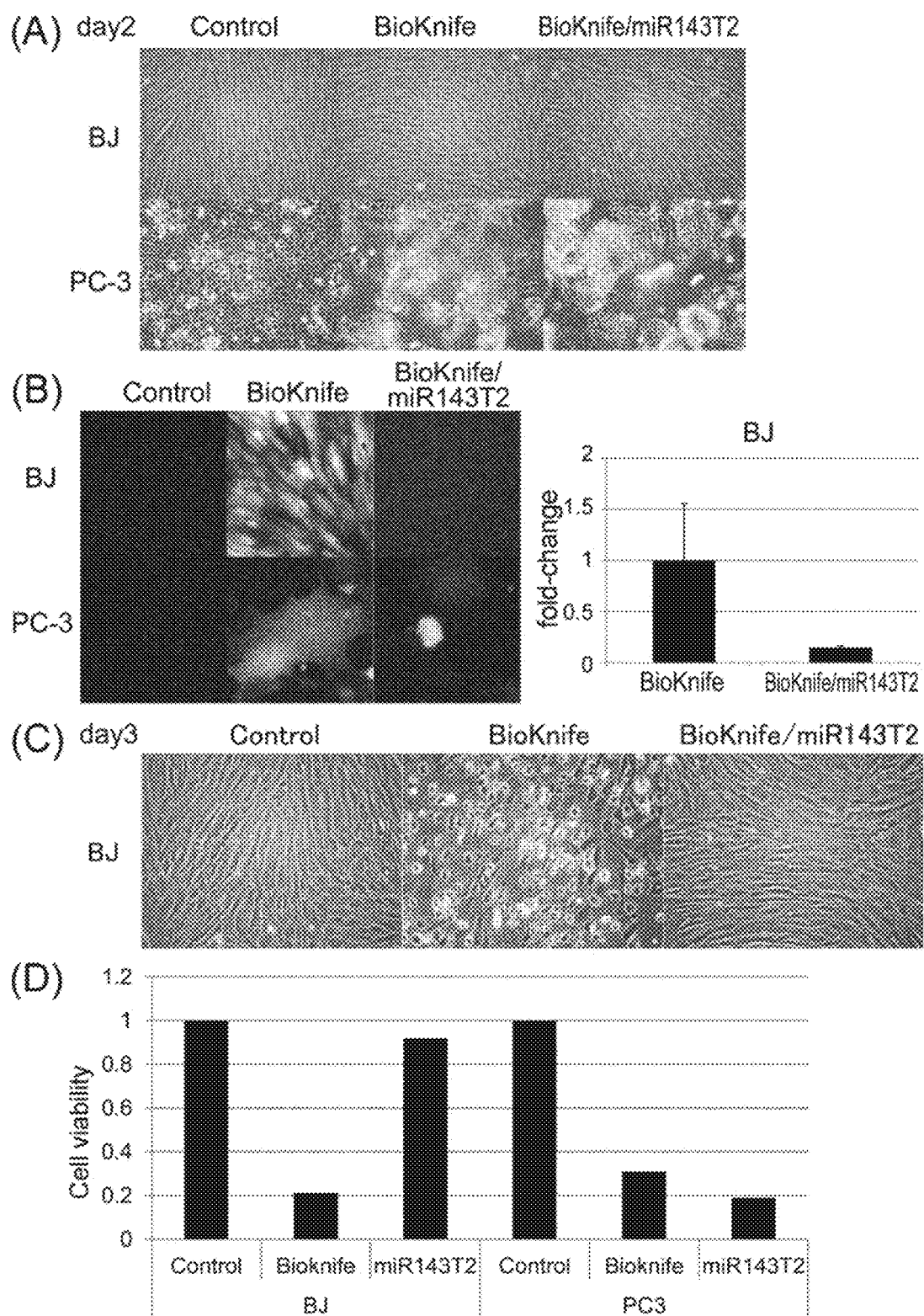
FIG. 17 is a set of diagrams showing the effect of microRNA target sequences loaded into M gene-deficient type vectors. A target sequence of miR-143 that is expressed in normal cells was loaded into the 3'-side of the P gene of a BioKnife type vector (vector carrying an F gene encoding an F protein in which the cleavage site has been modified into the uPA type), which induces cell fusion in a metastatic cancer cell-specific manner, among the M gene-deficient type vectors. Both a microRNA target sequence-carrying vector and a non-microRNA target sequence-carrying vector can induce cell fusion of cancer cells (PC-3); however, in the case of the vector carrying a microRNA target sequence (BioKnife/miR143T2), expression in normal cells (BJ) is noticeably suppressed (A and B). BJ cells exhibit cytotoxicity due to the infection with a vector that does not carry a microRNA target sequence (BioKnife); however, cytotoxicity is suppressed by loading a microRNA target sequence (miR143T2). Since expression is suppressed by the microRNA that is expressed in normal cells, it was confirmed that cytotoxicity for normal cells is not exhibited (C and D).

BJ cells and PC-3 cells were infected with SeV(PF) DGFP/TSΔM-Fct14 (uPA #2) (BioKnife) and SeV(PF) DGFP/TS4M-PmiR143T2Fct14 (uPA #2) (BioKnife/PmiR143T2) at 37° C., and an observation with a microscope and a fluorescence microscope was carried out on Day 2. Next, cytotoxicity was measured on Day 3 by using a Cell Counting Kit-8 (Dojindo Laboratories Co., Ltd.). As a result, cell fusion and cytolysis were observed in the PC-3 cells infected with BioKnife and BioKnife/PmiR143T2 (FIGS. 17A and 17B). In the BJ cells, cytotoxicity caused by infection with BioKnife was observed on Day 3. In contrast, in the BJ cells infected with BioKnife/PmiR143T2, not only fluorescence expression but also cytotoxicity was suppressed (FIGS. 17B to 17D). This implies that expression selectivity for cancer cells can be increased by microRNA target sequences, and cancer cells can be destroyed while the influence on normal cells is suppressed.

Example 18

Figure 18:
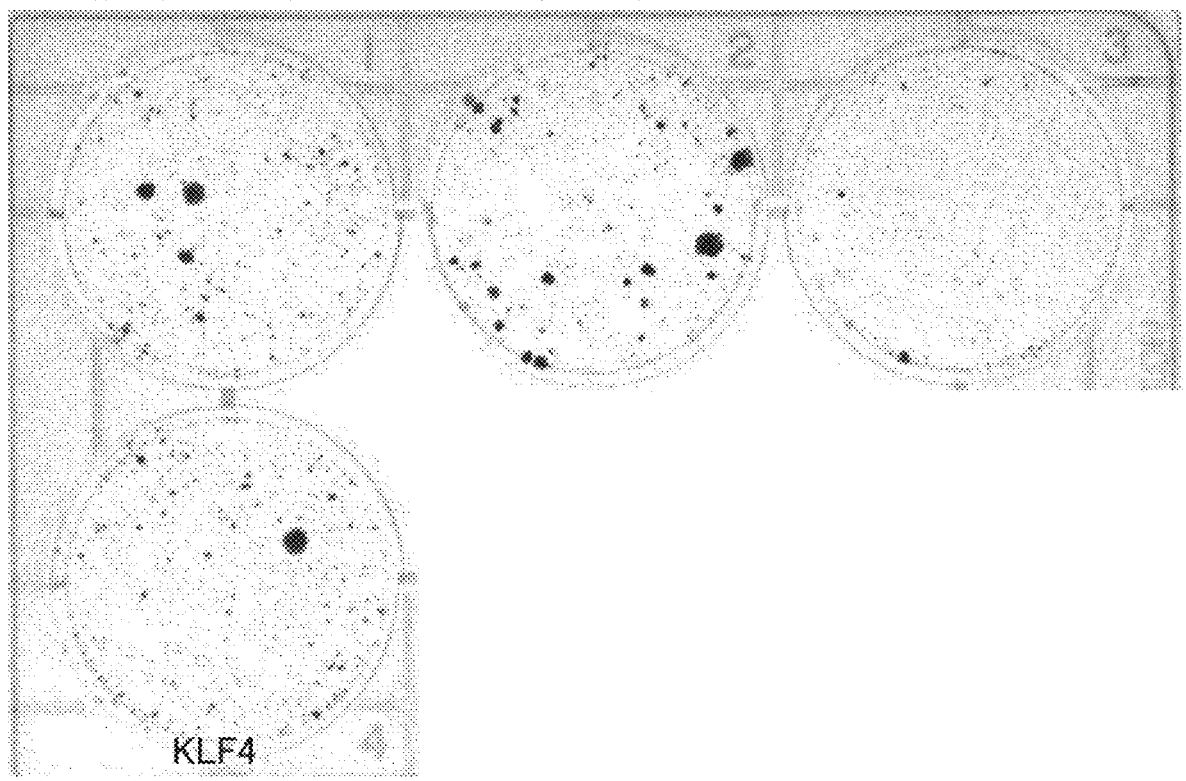
FIG. 18 is a set of diagrams showing the production of iPS cells (ALP staining) using miR367T2 vector.
Figure 18:
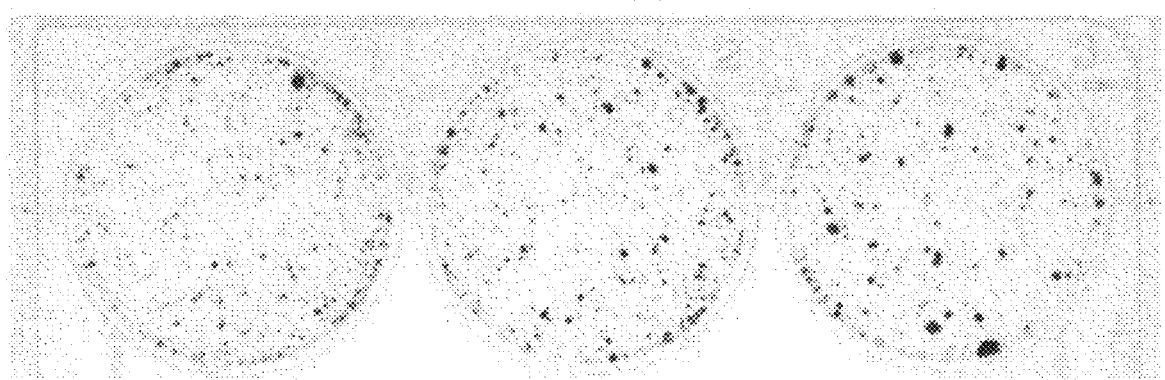
Figure 19:
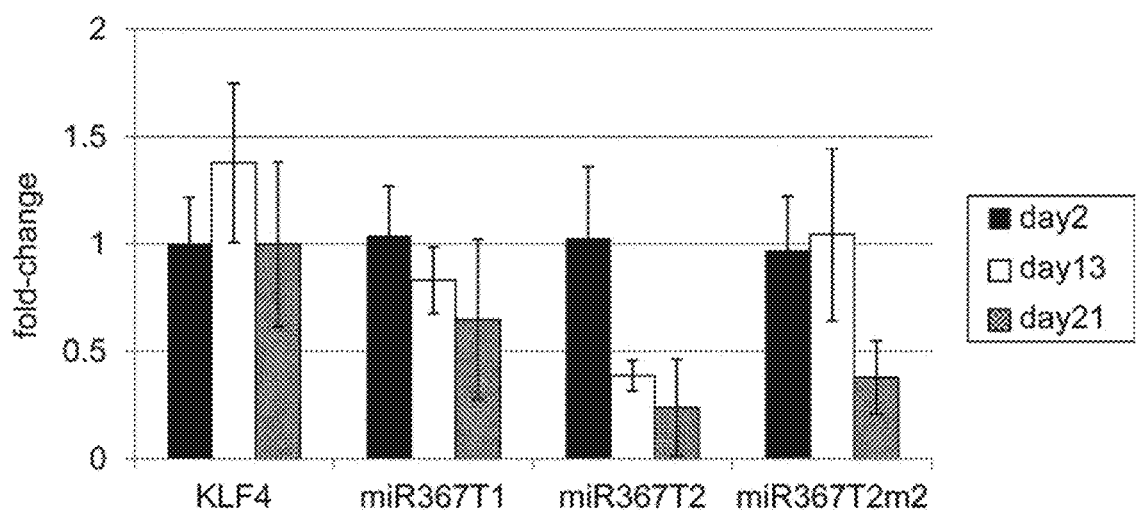
FIG. 19 is a set of diagrams showing the changes in vector expression (DGFP) in the process for producing iPS cells. A decrease in the level of DGFP expression of miR367T2 was observed (analysis by MetaMorph). It was confirmed that a decrease of 24% in the expression of conventional vector TS occurred on Day 21, and the vector was rapidly removed (A). Similar results were also observed in the case of using miR302T2 (B).
Figure 19:
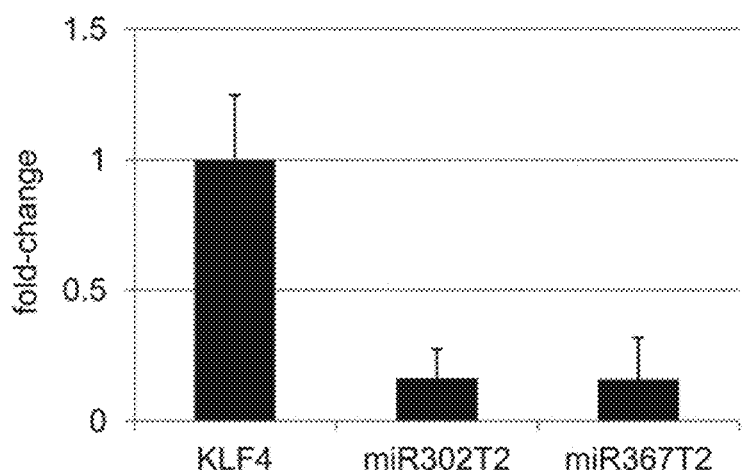

Production of iPS cells was carried out by co-infecting BJ cells with a combination of SeV18+KLF4/TSΔF (KLF4), SeV(PM) KOS/TS12ΔF (KOS), and SeV18+DGFP(HNL) cMYC/TS15ΔF (cMYC) (WO 2015/046229), or with one of SeV18+KLF4/PmiR367T1-TSΔF (KLF4-PmiR367T1), SeV18+KLF4/PmiR367T2-TSΔF (KLF4-PmiR367T2), SeV18+KLF4/PmiR367T2m2-TSΔF (KLF4-PmiR367T2 m2), and SeV18+KLF4/PmiR302T2-TSΔF (KLF4-PmiR302T2), instead of KLF4, at 37° C. The cells were inoculated on Matrigel on Day 6, and alkaline phosphatase (ALP) staining and an observation with a fluorescence microscope were carried out over time on Day 21. As a result, ALP-positive iPS cells were obtained on Day 21 (FIG. 18). When a comparison was made between KLF4, KLF4-PmiR367T1, KLF4-PmiR367T2, and KLF4-PmiR367T2m2, fluorescence expression occurred to the same extent on Day 2; however, KLF4-PmiR367T2 exhibited the largest decrease in fluorescence expression on Day 21 (FIG. 19A). When a comparison was made between KLF4, KLF4-PmiR367T2, and KLF4-PmiR302T2, the fluorescence intensities of KLF4-PmiR367T2 and KLF4-PmiR302T2 were 20% or less compared to that of KLF4 on Day 21 (FIG. 19B). When a comparison was made between KLF4 and KLF4-PmiR302T2 on Day 35, the fluorescence signal of KLF4-PmiR302T2 was 1/84 of that of KLF4. This implies that when microRNA target sequences are loaded into vectors for iPS cell production, vector removal is promoted by the microRNAs that are expressed during cell reprogramming.

Example 19

Figure 20:
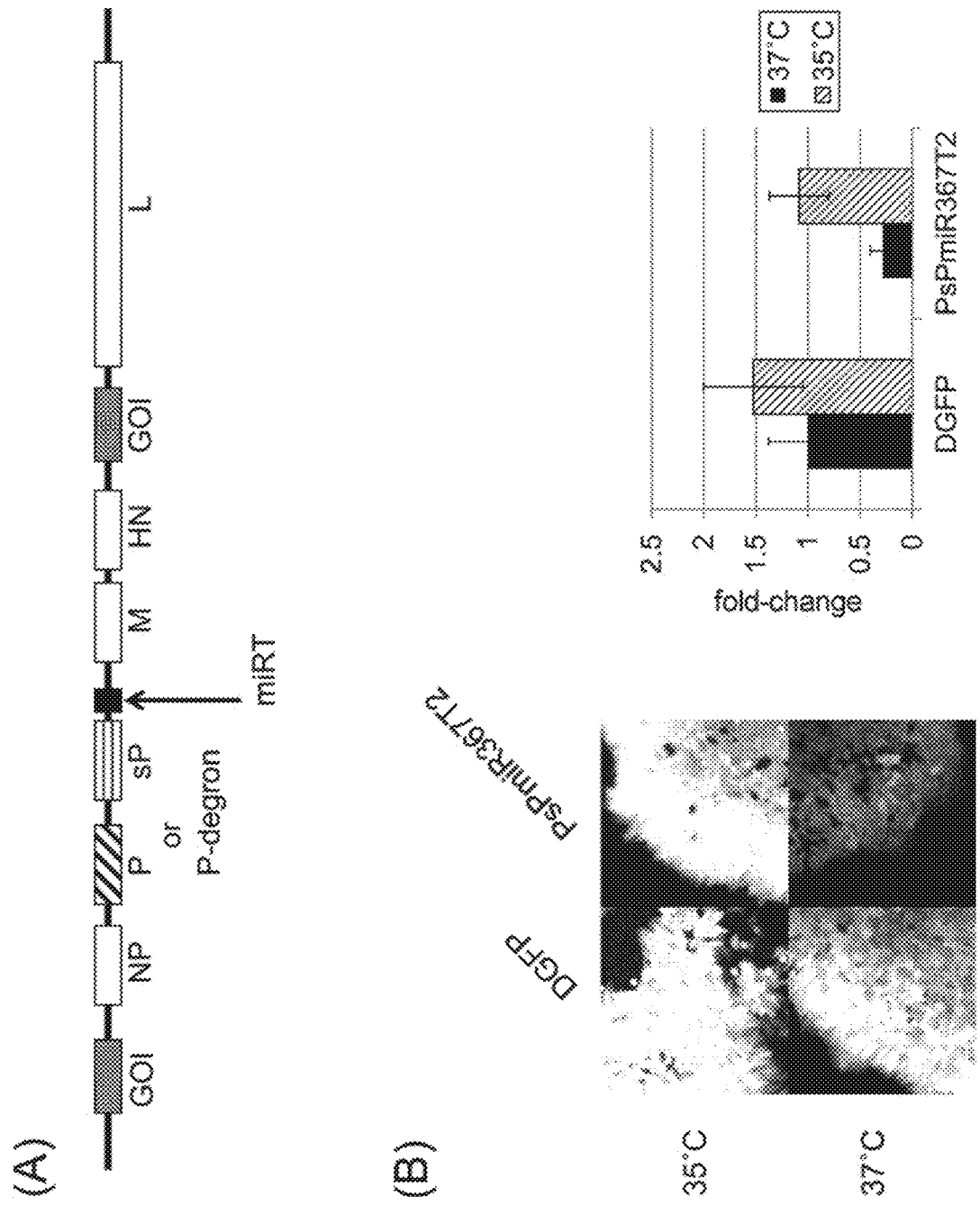
FIG. 20 is a set of diagrams showing the effect provided by a vector carrying a plurality of P genes. An example (A) of the loading positions of a second P gene and a microRNA target sequence. PsPmiR367T2 in which one of the P genes is derived from temperature-sensitive TS15 and miR367T2 has been added to the other P gene, is sufficiently expressed at 35° C.; however, as the temperature sensitivity also functions together with the microRNA target sequence at 37° C., expression is suppressed (B).
Figure 21:
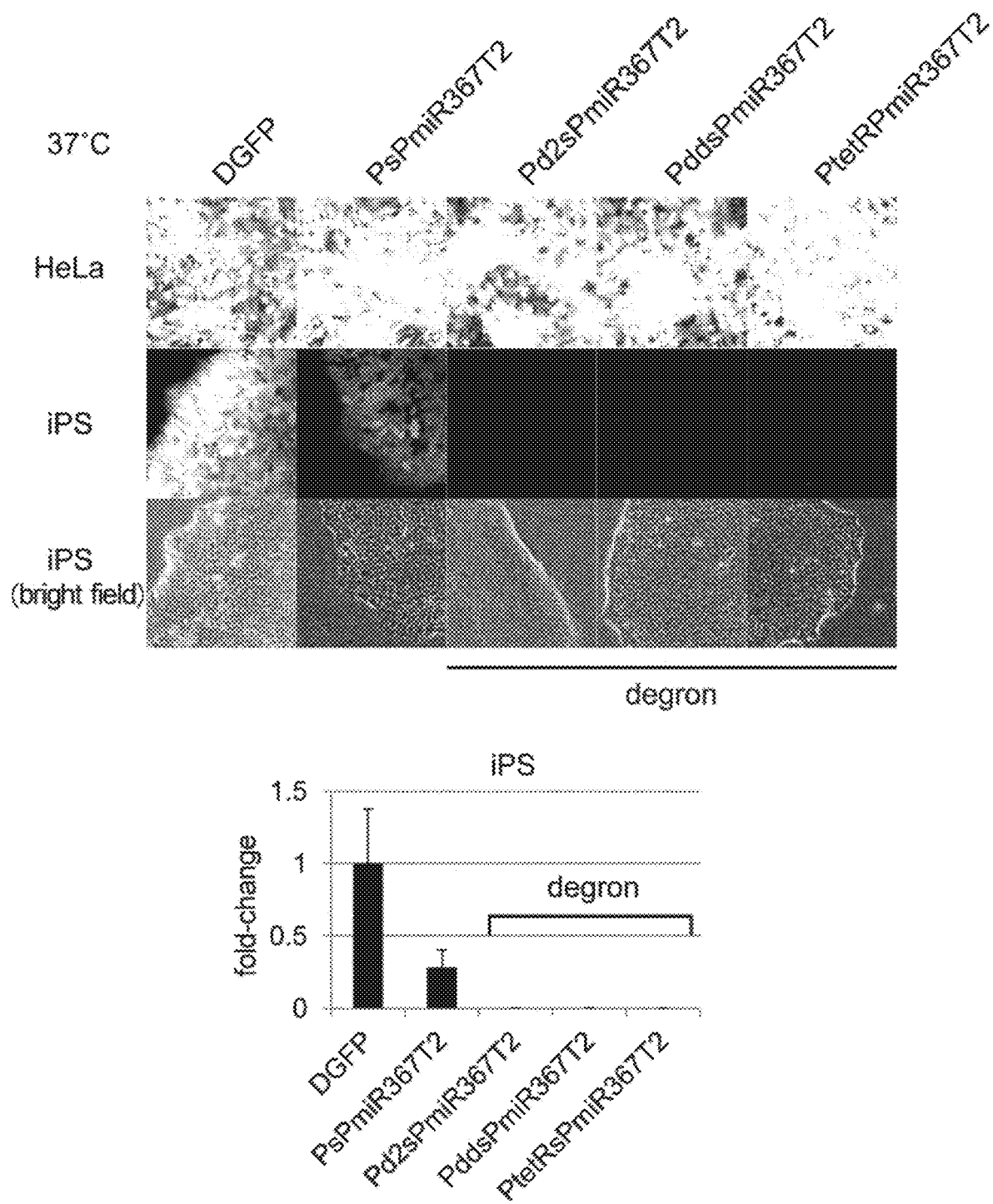
FIG. 21 is a set of pictures showing the effect provided by a vector carrying a plurality of P genes and having a degron added thereto. Regarding vectors in which a degron was added to one of the P genes and a microRNA target sequence was added to the other P gene (Pd2sPmiR367T2, PddsPmiR367T2, and PtetRsPmiR367T2), sufficient expression was achieved in cells that do not express the microRNA, and the vectors were removed in cells that express the microRNA. The effect of removing the vector carrying a degron was promoted compared to PsPmiR367T2 that did not carry a degron.

HeLa cells and iPS cells were infected with DGFP, SeV18+DGFP(HNL)cMYC/PsPmiR367T2-TS15ΔF (cMYC/PsPmiR367T2), SeV18+DGFP(HNL)cMYC/Pd2sPmiR367T2-TS15ΔF (cMYC/Pd2sPmiR367T2), SeV18+DGFP(HNL)cMYC/PddsPmiR367T2-TS15ΔF (cMYC/PddsPmiR367T2), or SeV18+DGFP(HNL)cMYC/PtetRsPmiR367T2-TS15ΔF (cMYC/PtetRsPmiR367T2) at 35° C. or 37° C. (the vector structures are shown in FIG. 20A), and an observation with a fluorescence microscope was carried out on Days 1 to 3. As a result, cMYC/PsPmiR367T2 infected at 35° C. exhibited sufficient expression in the iPS cells on Day 3, while the expression of cMYC/PsPmiR367T2 infected at 35° C. was suppressed (FIG. 20B). When the cells were infected at 37° C. with cMYC/Pd2sPmiR367T2, cMYC/PddsPmiR367T2, or cMYC/PtetRsPmiR367T2, to all of which degrons had been added, sufficient expression was observed in the HeLa cells in which microRNAs were not specifically expressed; however, rapid removal was observed in the iPS cells that specifically expressed microRNAs (FIG. 21). This implies that the vectors are vectors each carrying two P genes, in which one of the P genes could be temperature-controlled or degron-controlled, while the other P gene could be controlled by means of microRNA target sequence. Usually, when vectors having the TS15 skeleton are to infect cells at 37° C., sufficient expression cannot be obtained; however, when the vectors are produced to have a sequence in which simultaneously loaded P genes can be expressed at 37° C. (P protein having the TS skeleton), a system that is infective at 37° C., in which the P gene having the TS skeleton is deactivated by a microRNA whose expression is increased along with cell modification after infection, while the vector is removed by the other P protein having a degron added thereto, is obtained.

Example 20

Figure 22:
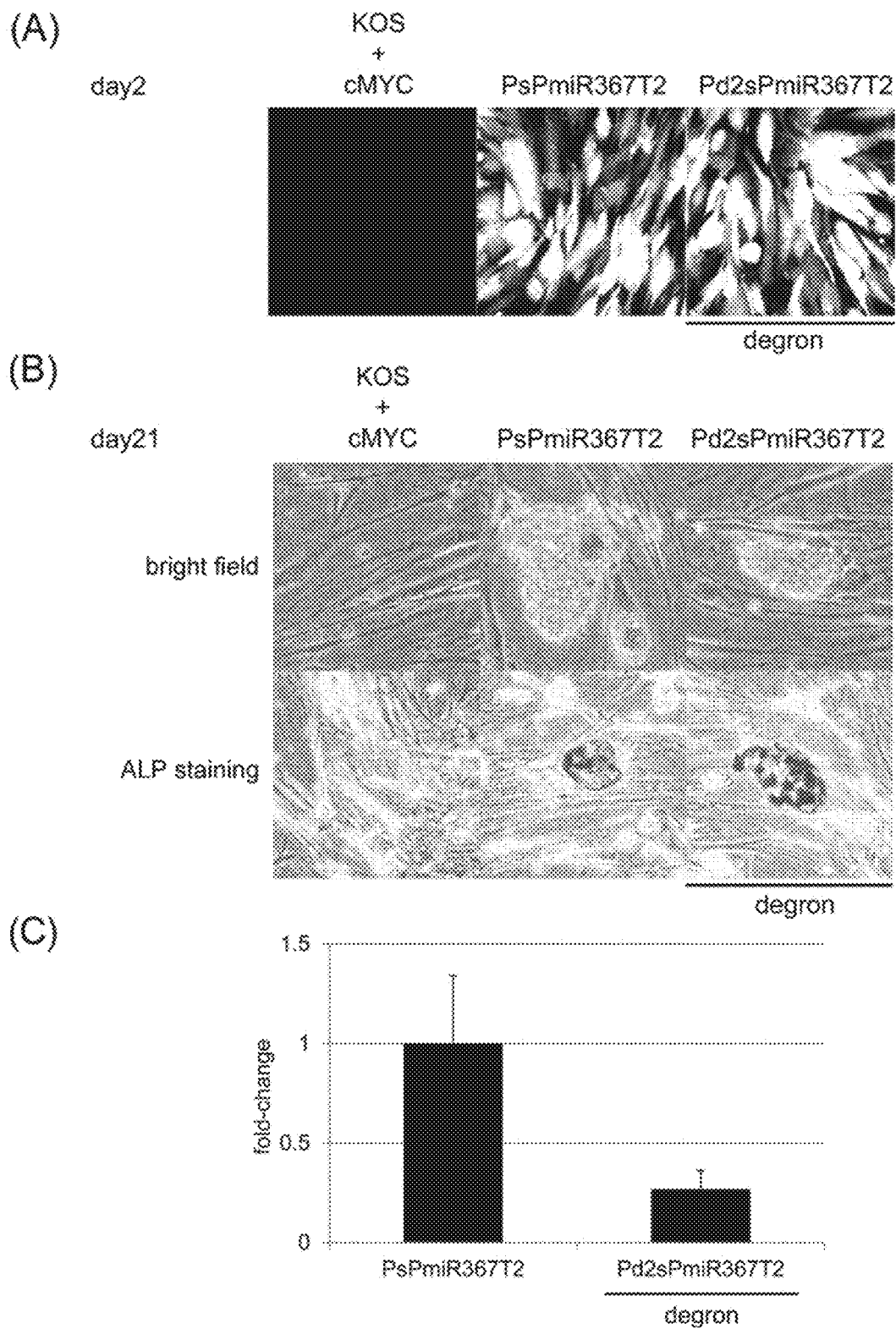
FIG. 22 is a set of diagrams showing the production of iPS cells using a vector carrying a plurality of P genes. With a combination of two vectors having the TS12 skeleton and the TS15 skeleton at 37° C., gene expression was hardly obtained; however, with the vector carrying a plurality of P genes, strong gene expression was obtained by using two vectors (A). With the vector carrying a plurality of P genes, ALP-positive iPS cells were obtained by using two vectors (B). Changes in vector expression (DGFP) in the process for producing iPS cells using a vector carrying a plurality of P genes are shown in (C). The effect of removing the vector carrying a degron was promoted compared to PsPmiR367T2 that did not carry a degron.

Production of iPS cells was carried out by infecting BJ cells with a combination of KOS and cMYC, or with any one of cMYC/PsPmiR367T2 and cMYC/Pd2sPmiR367T2 instead of cMYC, at 37° C. The cells were inoculated on feeder cells (mouse fibroblasts) on Day 6, and ALP staining and an observation with a fluorescence microscope were carried out over time on Day 21. As a result, fluorescence expression of the combination of KOS and cMYC was not observed on Day 2, while fluorescence expression of cMYC/PsPmiR367T2 or cMYC/Pd2sPmiR367T2 was observed (FIG. 22A). ALP-positive iPS cells were obtained on Day 21 (FIG. 22B). iPS cells were not obtained with the combination of KOS and cMYC; however, iPS cells were obtained with the vectors each carrying two P genes. On Day 21, a decrease in fluorescence expression of cMYC/Pd2sPmiR367T2 having a degron added thereto was observed, compared to the fluorescence expression of cMYC/PsPmiR367T2 (FIG. 22C). This implies that by using a vector carrying two P genes, a system that is infective at 37° C., in which the vector is removed after intended cells are obtained, is obtained.

INDUSTRIAL APPLICABILITY

According to the present invention, expression or removal of a vector can be controlled dependently on the expression of a microRNA. The vector of the present invention is useful, during the induction of cell differentiation or production of iPS cells, for rapidly decreasing the expression of the vector after the purpose is achieved, and removing the vector. Furthermore, when a vector whose expression is increased by a tumor cell-specific microRNA is used, upon introduction of a tumor-targeted vector, the vector can be expressed and proliferated more specifically in tumors.

The invention claimed is:

1. A modified Sendai virus vector, which comprises two P genes, wherein
a first P gene encodes a first P protein which comprises D433A, R434A, K437A, and L511F substitutions and is temperature sensitive, and further has a degron, and
a second P gene has a target sequence of a microRNA in its coding region or 5'- or 3'-noncoding region, and a P protein encoded by the second P gene does not contain a temperature sensitive mutation and is functionally expressed at 37° C.

2. The modified Sendai virus vector according to claim 1, wherein the microRNA is miR143 and the degron is a mODC PEST degron.

* * * * *